US008486974B2

(12) United States Patent
Gilmer et al.

(10) Patent No.: US 8,486,974 B2
(45) Date of Patent: Jul. 16, 2013

(54) EFFICIENT ASPIRIN PRODRUGS

(75) Inventors: John Francis Gilmer, Kingswood Heights (IE); Louise Clune-Moriarty, Quin (IE); Maeve Lally, Ballsbridge (IE)

(73) Assignee: The Provost, Fellows and Scholars of The College of The Holy and Undivided Trinity of Queen Elizabeth (IE)

( * ) Notice: Subject to any disclaimer, the term of this patent is extended or adjusted under 35 U.S.C. 154(b) by 130 days.

(21) Appl. No.: 12/808,693

(22) PCT Filed: Dec. 19, 2008

(86) PCT No.: PCT/EP2008/068114
§ 371 (c)(1),
(2), (4) Date: Nov. 1, 2010

(87) PCT Pub. No.: WO2009/080795
PCT Pub. Date: Jul. 2, 2009

(65) Prior Publication Data
US 2011/0046182 A1    Feb. 24, 2011

(30) Foreign Application Priority Data
Dec. 21, 2007   (IE) .................................... 2007/0934

(51) Int. Cl.
*A61K 31/4406*   (2006.01)
*C07D 405/12*    (2006.01)
(52) U.S. Cl.
USPC ....................... 514/338; 546/284.1
(58) Field of Classification Search
USPC ....................... 514/338; 546/284.1
See application file for complete search history.

(56) References Cited

U.S. PATENT DOCUMENTS
2012/0082634 A1   4/2012   Ledwidge

FOREIGN PATENT DOCUMENTS
| CN | 1618798 | 5/2005 |
| EP | 1 120 419 B1 | 4/2006 |
| WO | WO 98/17673 | 4/1998 |
| WO | WO 2005/037842 | 4/2005 |
| WO | WO 2012/017321 | 2/2012 |

OTHER PUBLICATIONS

Akre, K., A. Ekstrom, et al. (2001). "Aspirin and risk for gastric cancer: a population-based case-control study in Sweden." British Journal of Cancer 84(7): 965-968.
Antithrombotic Trialists (ATT) Collaboration (2002). "Colloborative meta-analysis of randomised trials of antiplatelet therapy for prevention of death, myocardial infarction, and stroke in high risk patients." British Medical Journal 324: 71.
Antithrombotic Trialists (ATT) Collaboration (2009). "Aspirin in the primary and secondary prevention of vascular disease: collaborative meta-analysis of individual participant data from randomised trials." Lancet 373: 1849-1860.
Asano, T. K. and R. S. McLeod (2004). "Non steroidal anti-inflammatory drugs (NSAID) and aspirin for preventing colorectal adenomas and carcinomas." Cochrane Database of Systematic Reviews (1): Art. No. CD004079.
Bachert, C., A. G. Chuchalin, et al. (2005). "Aspirin Compared with Acetaminophen in the Treatment of Feverand OtherSymptoms of Upper Respiratory Tract Infection in Adults: A Multicenter, Randomized, Double-Blind, Double-Dummy, Placebo-Controlled, Parallel-Group, Single-Dose, 6-Hour Dose-Ranging Study." Clinical Therapeutics 27(7): 993-1003.
Bellavance, A. (1993). "Efficacy of ticlopidine and aspirin for prevention of reversible cerebrovascular ischemic events. The Ticlopidine Aspirin Stroke Study." Stroke 24(10): 1452-1457.
Bhatt, D. L., K. A. A. Fox, et al. (2006). "Clopidogrel and Aspirin versus Aspirin Alone for the Prevention of Atherothrombotic Events." N. Engl J Med 354(16): 1706-1717.
Bosetti, C., S. Gallus, et al. (2009). "Aspirin and cancer risk: a summary review to 2007." Recent Results Cancer Res 181(231-251).
Brune, K., W. S. Beck, et al. (1991). "Aspirin-like drugs may block pain independently of prostaglandin synthesis inhibition." Experientia 47(3): 257-261.
Chan At, G. E. L. M. J. A. S. E. S. C. G. C. F. C. S. (2005). "LOng-term use of aspirin and nonsteroidal anti-inflammatory drugs and risk of colorectal cancer." JAMA 294(8): 914-923.

(Continued)

*Primary Examiner* — Taofiq A Solola
(74) *Attorney, Agent, or Firm* — Choate, Hall & Stewart LLP; Andrea L. C. Robidoux; Kristen C. Buteau

(57) ABSTRACT

Aspirin is one of the most widely used drugs in the treatment of inflammation, pain and fever. It has more recently found application in the prevention of heart attacks and stroke and is being studied as a cancer chemopreventative agent. Despite its value aspirin continues to be underutilized because it causes gastric bleeding. The technology under development potentially removes this problem. It is designed to reduce contact between the drug and the intestinal lining. An isosorbide aspirinate prodrug compound is thus provided. The compound has the general structure as shown in general formula (I) wherein Y is a $C_1$-$C_8$ alkyl ester, a $C_1$-$C_8$ alkoxy ester, a $C_3$-$C_{10}$ cycloalkyl ester, an arylester, a $C_1$-$C_8$ alkylaryl ester or —C(O)OR$_{ring}$, wherein R$_{ring}$ is a 5-membered aromatic or nonaromatic 5-member ring having at least one heteroatom substituted for a carbon of the ring system, which can be unsubstituted or substituted with at least one nitric oxide releasing group.

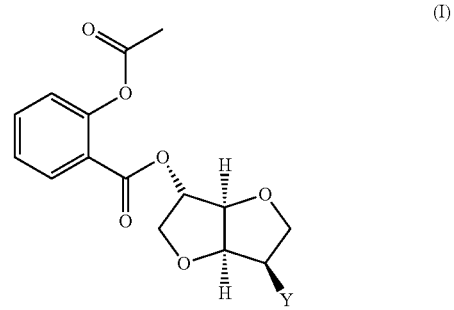

(I)

17 Claims, 16 Drawing Sheets

OTHER PUBLICATIONS

Castelao, J., J. Yuan, et al. (2000). "Non-steroidal anti-inflammatory drugs and bladder cancer prevention." British Journal of Cancer 82(7): 1364-1369.

Cook Nr, L. I. G. J. and et al. (2005). "Low-dose aspirin in the primary prevention of cancer: The women's health study: a randomized controlled trial." JAMA 294(1): 47-55.

Corley, D., K. Kerlikowske, et al. (2003). "Protective association of aspirin/NSAIDs and esophageal cancer: a systematic review and meta-analysis." Gastroenterology 124(1): 47-56.

Diener, H. C., L. Cunha, et al. (1996). "European Stroke Prevention Study 2. Dipyridamole and acetylsalicylic acid in the secondary prevention of stroke." Journal of the Neurological Sciences 143(1-2): 1-13.

Eccles, R. (2003). "Effects of acetylsalicylic acid on sore throat pain and other pain symptoms associated with acute upper respiratory tract infection." Pain Med. 4(2): 118-124.

Edwards, J. E., A. D. Oldman, et al. (1999). "Oral aspirin in postoperative pain: a quantitative systematic review." Pain 81(3): 289-297.

Eidelman, R., P. Hebert, et al. (2003). "An update on aspirin in the primary prevention of cardiovascular disease." Arch Intern Med 163(17): 2006-2010.

Elwood, P. C., A. M. Gallagher, et al. (2009). "Aspirin, salicylates, and cancer." Lancet 373(9671): 1301-1309.

Etminan, M., S. Gill, et al. (2003). "Effect of non-steroidal anti-inflammatory drugs on risk of Alzheimer's disease: systematic review and meta-analysis of observational studies." BMJ 327(7407): 128.

Farrow, D., T. Vaughan, et al. (1998). "Use of aspirin and other nonsteroidal anti-inflammatory drugs and risk of esophageal and gastric cancer." Cancer Epidemiol Biomarkers Prev 7(2): 97-102.

Flossmann, E. and P. M. Rothwell (2007). "Effect of aspirin on long-term risk of colorectal cancer: consistent evidence from randomised and observational studies." The Lancet 369(9573): 1603-1613.

Funkhouser, E. and G. Sharp (1995). "Aspirin and reduced risk of esophageal carcinoma." Cancer 76(7): 1116-1119.

Gann, P. H., J. E. Manson, et al. (1993). "Low-Dose Aspirin and Incidence of Colorectal Tumors in a Randomized Trial." Journal of the National Cancer Institute 85(15): 1220-1224.

Gilroy, D. W., A. Tomlinson, et al. (1998). "Differential effects of inhibitors of cyclooxygenase (cyclooxygenase 1 and cyclooxygenase 2) in acute inflammation." European journal of pharmacology 355(2-3): 211-217.

Giovannucci, E., K. M. Egan, et al. (1995). "Aspirin and the Risk of Colorectal Cancer in Women." New England Journal of Medicine 333(10): 609-614.

Gonzalez-Perez, A., L. Garcia Rodriguez, et al. (2003). "Effects of non-steroidal anti-inflammatory drugs on cancer sites other than the colon and rectum: a meta-analysis." BMC Cancer 3(1): 28.

Harris, R. E., J. Beebe-Donk, et al. (2005). "Aspirin, ibuprofen, and other non-steroidal anti-inflammatory drugs in cancer prevention: a critical review of non-selective COX-2 blockade (review)." Oncology Reports 13(4): 559-583. (Abstract).

Hayden, M., M. Pignone, et al. (2002). "Aspirin for the primary prevention of cardiovascular events: a summary of the evidence." Stroke 3: 14-21.

Hennekens, C. H., J. E. Buring, et al. (1989). "Aspirin and other antiplatelet agents in the secondary and primary prevention of cardiovascular disease." Circulation 80(4): 749-756.

Holick, C. N. (2003). "Aspirin use and lung cancer in men." Br J Cancer 89(9): 1705-1708.

Holmes, M. D., W. Y. Chen, et al. (2010). "Aspirin Intake and Survival After Breast Cancer." Journal of Clinical Oncology 28(9): 1467-1472.

Jacobs, E. J., C. Rodriguez, et al. (2005). "A Large Cohort Study of Aspirin and Other Nonsteroidal Anti-inflammatory Drugs and Prostate Cancer Incidence." Journal of the National Cancer Institute 97(13): 975-980.

Johnson, E. S., S. F. Lanes, et al. (1999). "A Metaregression Analysis of the Dose-Response Effect of Aspirin on Stroke." Arch Intern Med 159(11): 1248-1253.

Khuder, S. A. and A. B. Mutgi (2001). "Breast cancer and NSAID use: a meta-analysis." Br J Cancer 84(9): 1188-1192.

Kopp, E. and S. Ghosh (1994). "Inhibition of NF-kappa B by sodium salicylate and aspirin." Science 265(5174): 956-959.

Kune, G. A., S. Kune, et al. (1988). "Colorectal Cancer Risk, Chronic Illnesses, Operations, and Medications: Case Control Results from the Melbourne Colorectal Cancer Study." Cancer Research 48(15): 4399-4404.

Leitzmann, M., M. Stampfer, et al. (2002). "Aspirin use in relation to risk of prostate cancer." Cancer Epidemiol Biomarkers Prev 11(10): 1108-1111.

Lip, G. Y. and S. J. Edwards (2006). "Stroke prevention with aspirin, warfarin and ximelagatran in patients with non-valvular atrial fibrillation: a systematic review and meta-analysis." Thrombosis research 118(3): 321-334.

Lipton, R. B., W. F. Stewart, et al. (1998). "Efficacy and safety of acetaminophen, aspirin, and caffeine in alleviating migraine headache pain: three double-blind, randomized, placebo-controlled trials." Archives of neurology 55(2): 210.

Mahmud, S., E. Franco, et al. (2004). "Prostate cancer and use of nonsteroidal anti-inflammatory drugs: systematic review and meta-analysis." Br J Cancer 90(1): 93-99.

Moncada, S., S. H. Ferreira, et al. (1973). "Prostaglandins, Aspirin-like Drugs and the Oedema of Inflammation." Nature 246(5430): 217-219.

Moore, N., E. Vanganse, et al. (1999). "The PAIN Study: Paracetamol, Aspirin and Ibuprofen New Tolerability Study: A Large-Scale, Randomised Clinical Trial Comparing the Tolerability of Aspirin, Ibuprofen and Paracetamol for Short-Term Analgesia." Clinical Drug Investigation 18(2): 89-98.

Nilsson, S., B. Johansson, et al. (2003). "Does aspirin protect against Alzheimer's dementia? A study in a Swedish population-based sample aged $\geq 80$ years." European Journal of Clinical Pharmacology 59(4): 313-319.

Peto, R., R. Gray, et al. (1988). "Randomised trial of prophylactic daily aspirin in British male doctors." Br Med J (Clin Res Ed) 296(6618): 313-316.

Rich, J. B., D. X. Rasmusson, et al. (1995). "Nonsteroidal anti-inflammatory drugs in Alzheimer's disease." Neurology 45(1): 51-55.

Ridker, P. M., N. R. Cook, et al. (2005). "A Randomized Trial of Low-Dose Aspirin in the Primary Prevention of Cardiovascular Disease in Women." New England Journal of Medicine 352(13): 1293-1304.

Rothwell, P. M., F. G. R. Fowkes, et al. (2011). "Effect of daily aspirin on long-term risk of death due to cancer: analysis of individual patient data from randomised trials." The Lancet 377(9759): 31-41.

Rothwell, P. M., M. Wilson, et al. (2010). "Long-term effect of aspirin on colorectal cancer incidence and mortality: 20-year follow-up of five randomised trials." The Lancet 376(9754): 1741-1750.

Schreinemachers, D. and R. Everson (1994). "Aspirin use and lung, colon, and breast cancer incidence in a prospective study." Epidemiology 5(2): 138-146.

Smith, J. S. C., J. Allen, et al. (2006). "AHA/ACC Guidelines for Secondary Prevention for Patients With Coronary and Other Atherosclerotic Vascular Disease: 2006 UpdateEndorsed by the National Heart, Lung, and Blood Institute." Journal of the American College of Cardiology 47(10): 2130-2139.

Steele, R. W., F. S. Young, et al. (1972). "Oral antipyretic therapy: evaluation of aspirin-acetaminophen combination." Archives of Pediatrics & Adolescent Medicine 123(3): 204.

Stewart, W. F., C. Kawas, et al. (1997). "Risk of Alzheimer's disease and duration of NSAID use." Neurology 48(3): 626-632.

Thun, M. J., S. J. Henley, et al. (2002). "Nonsteroidal Anti-inflammatory Drugs as Anticancer Agents: Mechanistic, Pharmacologic, and Clinical Issues." Journal of the National Cancer Institute 94(4): 252-266.

Vane, J. R. and R. M. Botting (2003). "The mechanism of action of aspirin." Thrombosis research 110(5-6): 255-258.

Wald, N. J. and M. R. Law (2003). "A strategy to reduce cardiovascular disease by more than 80%." BMJ 326(7404): 1419.

Wang, W. H., J. Q. Huang, et al. (2003). "Non-steroidal Anti-inflammatory Drug Use and the Risk of Gastric Cancer: A Systematic Review and Meta-analysis." Journal of the National Cancer Institute 95(23): 1784-1791.

Zhang, S. M., N. R. Cook, et al. (2008). "Low-dose aspirin and breast cancer risk: results by tumour characteristics from a randomised trial." Br J Cancer 98(5): 989-991.

Yaffe, S. J. (1981). "COmparative efficacy of aspirin and acetaminophen in the reduction of fever in children." Archives of Internal Medicine 141(3): 286-292.

Burn, J., A.-M. Gerdes, et al. (2011). "Long-term effect of aspirin on cancer risk in carriers of hereditary colorectal cancer: an analysis from the CAPP2 randomised controlled trial." The Lancet.

Albert, "Chemical aspects of selective toxicity" Nature 182(4633):421-2 (1958).

Australian Patent Examination Report No. 1 for AU2008339961, mailed Nov. 15, 2012.

Burton et al., "Cleavage of carboxylic acid esters to acid chlorides with dichlorotriphenyphosphorane" J. Org. Chem. 40(21):3026-32 1975.

Carini et al., "In vitro metabolism of a nitroderivative of acetylsalicylic acid (NCX4016) by rat liver: LC and LC-MS studies" J Pharm Biomed Anal. 29(6):1061-71 (2002).

Cena et al., "Antiinflammatory, gastrosparing, and antiplatelet properties of new NO-donor esters of aspirin" J Med Chem. 46(5):747-54 (2003).

Chan et al., "Long-term use of aspirin and nonsteroidal anti-inflammatory drugs and risk of colorectal cancer" JAMA 294(8):914-23 (2005).

Corazzi et al, "Direct and irreversible inhibition of cyclooxygenase-1 by nitroaspirin (NCX 4016)" J Pharmacol Exp Ther. 315(3):1331-7 (2005).

Cryer et al., "Effects of very low dose daily, long-term aspirin therapy on gastric, duodenal, and rectal prostaglandin levels and on mucosal injury in healthy humans" Gastroenterology 117(1):17-25 (1999).

Cryer, "Gastrointestinal safety of low-dose aspirin" Am J Manag Care. 8(22 Suppl):5701-8 (2002).

Ellman et al., "A new and rapid colorimetric determination of acetylcholinesterase activity" Biochem Pharmacol. 7:88-95 (1961).

Etminan et al., "Effect of non-steroidal anti-inflammatory drugs on risk of Alzheimer's disease: systematic review and meta-analysis of observational studies" BMJ 327(7407):128 (2003).

Fiorucci et al., "Gastrointestinal safety of NO-aspirin (NCX-4016) in healthy human volunteers: a proof of concept endoscopic study" Gastroenterology 124(3):600-7 (2003).

Fiorucci et al., "NO-aspirin: mechanism of action and gastrointestinal safety" Dig Liver Dis. 35 Suppl 2:S9-19 (2003).

Gaynor et al., "Synthesis and structure activity relationships (SAR) of a new class of potent and selective butyrylcholinesterase inhibitors" Chem Biol Interact. 157-158:380-1 (2005).

Gilmer et al., "Evaluation of nitrate-substituted pseudocholine esters of aspirin as potential nitro-aspirins" Bioorg Med Chem Lett. 17(11):3217-20 (2007).

Gilmer et al., "Isosorbide-based aspirin prodrugs. II. Hydrolysis kinetics of isosorbide diaspirinate" Eur J Pharm Sci. 16(4-5):297-304 (2002).

Gilmer et al., "Single oral dose study of two isosorbide-based aspirin prodrugs in the dog" J Pharm Pharmacol. Oct;55(10):1351-7 (2003).

Gilmer et al., "Synthesis, hydrolysis kinetics and anti-platelet effects of isosorbide mononitrate derivatives of aspirin" Eur J Pharm Sci. 14(3):221-7 (2001).

International Search Report for PCT/EP08/068114 Filed Dec. 19, 2008, mailed Mar. 30, 2009.

Jones, "Decreased toxicity and adverse reaction via prodrugs" in Bundgaard H., (Ed.) Design of Prodrugs, Elsevier, Amsterdam, 199-241 (1985).

Jurasz et al., "Role of von Willebrand factor in tumour cell-induced platelet aggregation: differential regulation by NO and prostacyclin" Br J Pharmacol. 134(5):1104-12 (2001).

Kelly et al., "Risk of aspirin-associated major upper-gastrointestinal bleeding with enteric-coated or buffered product" Lancet 348(9039):1413-6 (1996).

Laheij et al., "Helicobacter pylori infection as a risk factor for gastrointestinal symptoms in patients using aspirin to prevent ischaemic heart disease" Aliment Pharmacol Ther. 15(7):1055-9 (2001).

Lazzarato et al., "Searching for New NO-Donor Aspirin-like Molecules: A New Class of Nitrooxy-acyl Derivatives of Salicylic Acid" J. Med. Chem., 51:1984-1903 (2008).

Levin, "Theriac found? Nitric oxide-aspirin and the search for the universal cure" J Am Coll Cardiol. 44(3):642-3 (2004).

Li et al., "Butyrylcholinesterase, paraoxonase, and albumin esterase, but not carboxylesterase, are present in human plasma" Biochem Pharmacol. 70(11):1673-84 (2005).

Mashita et al., "Oral but not parenteral aspirin upregulates COX-2 expression in rat stomachs. a relationship between COX-2 expression and PG deficiency" Digestion 73(2-3):124-32 (2006).

Morgan, "A quantitative illustration of the public health potential of aspirin" Med Hypotheses.60(6):900-2 (2003).

Moriarty et al., "Discovery of a "true" aspirin prodrug" J Med Chem. 51(24):7991-9 (2008).

Newton et al., "Review article: the ageing bowel and intolerance to aspirin" Aliment Pharmacol Ther. 19(1):39-45 (2004).

Nielsen et al., "Evaluation of glycolamide esters and various other esters of aspirin as true aspirin prodrugs" J Med Chem. 32(3):727-34 (1989).

Pedersen et al., "Dose-related kinetics of aspirin. Presystemic acetylation of platelet cyclooxygenase" N Engl J Med. 311(19):1206-11 (1984).

Qu et al., "The physiologic disposition and pharmacokinetics of guaiacol acetylsalicylate in rats" Yao Xue Xue Bao. 25(9):664-9 (1990).

Radomski et al., "Pharmacological characteristics of solid-phase von Willebrand factor in human platelets" Br J Pharmacol. 134(5):1013-20 (2001).

Soars et al., "In vitro analysis of human drug glucuronidation and prediction of in vivo metabolic clearance" J Pharmacol Exp Ther. 301(1):382-90 (2002).

St. Pierre et al., "Intramolecular catalysis in the reactions of nucleophilic reagents with aspirin" J Am Chem Soc. 90(14):3817-27 (1968).

Tesei et al., "NCX 4016, a nitric oxide-releasing aspirin derivative, exhibits a significant antiproliferative effect and alters cell cycle progression in human colon adenocarcinoma cell lines" Int J Oncol. 22(6):1297-302 (2003).

Velázquez et al., "Novel nonsteroidal antiinflammatory drugs possessing a nitric oxide donor diazen-1-ium-1,2-diolate moiety: design, synthesis, biological evaluation, and nitric oxide release studies" J Med Chem. 48(12):4061-7 (2005).

Walker et al., "Does enteric-coated aspirin result in a lower incidence of gastrointestinal complications compared to normal aspirin?" Interact Cardiovasc Thorac Surg. 6(4):519-22 (2007).

Williams et al., "Benorylate hydrolysis by human plasma and human liver"Br J Clin Pharmacol. 28(6):703-8 (1989).

Written Opinion of the International Searching Authority for PCT/EP08/068114 Filed Dec. 19, 2008, mailed Mar. 30, 2009.

% of Inhibition of collagen induced aggregation in human PRP

EFFICIENT ASPIRIN PRODRUGS

CROSS-REFERENCE TO RELATED APPLICATIONS

This application claims priority to and is a national phase application under 35 USC §371 of International application number PCT/EP2008/068114, filed Dec. 19, 2008, which claims priority to Irish patent application serial number 2007/0934, filed on Dec. 21, 2007, the entirety of each of which is hereby incorporated by reference.

FIELD OF THE INVENTION

This invention relates to potent aspirin prodrugs which are stable to moisture and towards conditions encountered in the lumen of the GI tract but will break down rapidly during and after absorption to release aspirin and/or nitric oxide (NO).

BACKGROUND TO THE INVENTION

Aspirin is one of the most widely used drugs in the world. Regular use is associated with reduced risk of mortality in all cardiovascular risk groups. It is an anti-inflammatory, analgesic and anti-pyretic agent and is used in the fight against cardiovascular disease and is predicted to have a role in preventing colorectal, oesophageal, gastric and lung cancers (e.g. Chan 2005) as well as stroke, Alzheimer's disease (Etminan et al., 2003) and other forms of dementia. Some models predict that daily aspirin consumption by people over fifty years would double their chances of living until their 90's (Morgan, 2003).

The main side effects associated with aspirin use are gastrointestinal. Aspirin causes dyspepsia in nearly half of all patients and it triples the risk of GI bleeding. Endoscopically controlled studies demonstrate an increased risk of bleeding at all aspirin doses even at the relatively low doses used in the prevention of myocardial infarction (MI). In one study, 10% of patients on low dose aspirin (10-300 mg/day) had endoscopic ulcers after 12 weeks, with one case occurring at 10 mg/day (Cryer & Feldman, 1999, Cryer 2002). Several studies have shown bleeding commences 5 to 30 days after the start of therapy indicating that adaptation does not occur. Significantly, the risk of GI side-effects has limited aspirin use to patient groups with a high probability of a thrombotic event: in a random population the risk of serious GI injury is higher than the risk of aspirin-preventable death. As of yet, there are no reliable dose-related data for the prophylactic use of aspirin in cancer, however, it seems likely to be higher than the optimal dose required for its established role in the prevention of heart attack and so there is likely to be an increased risk of greater GI toxicity. Although the absolute risks are low (1-2%), its widespread and rapidly growing consumption causes aspirin-induced gastrointestinal toxicity to be a public health concern (Morgan, 2003; Laheij 2001; Newton et al., 2004). A number of contributions to aspirin GI toxicity are recognised. The gut wall is protected from the harsh luminal contents by a protective layer. This barrier is partly maintained by the two cyclooxygenase enzymes (COX-1 & COX-2). The cardiovascular protective effects of aspirin stem from its inhibition of platelet cyclooxygenase enzyme COX-1, while its cytoprotective effects have been attributed to its unique ability to acetylate the cyclooxygenase enzyme COX-2 which causes arachidonic acid to be shunted away from $PGE_2$, a cancer promoter, towards HETE, a cancer suppressor. COX-2 also has role in wound healing in the GIT. Aspirin inhibits these enzymes as it passes through the gut during absorption and so attenuates their protective role. The biochemical aspect of toxicity therefore results from local inhibition of COX-1 and COX-2 by aspirin which leads to suppression of the prostaglandins ($PGE_2$, $PGI_2$) that normally regulate gastric acid secretion and blood flow. There is also a clear chemical aspect to aspirin's toxicity. Aspirin is a hydrophobic acid (pKa 3.5). It is lipid soluble at low pH values and it is able to disrupt the hydrophobic layer covering the epithelium allowing access by luminal contents, causing irritation, eventually leading to ulceration. This may be a more important cause of toxicity than the biochemical component. In one recent study, the administration of oral aspirin to rats caused gastric lesions whereas there was no gastric damage when the drug was given subcutaneously, despite evidence of inhibition of COX from both routes (Mahita, 2006). Drug-induced GI toxicity is very complex and the subject of frequently conflicting findings but this particular study indicates that chemical toxicity is significant.

The problem of GI toxicity has been the focus of pharmaceutical attention for many years, but endoscopic studies demonstrate that conventional solutions such as enteric coatings or buffering are at best inadequate (Kelly et al, 1996, Walker et al., 2007). Thus establishing new ways of delivering aspirin or dealing with its GI effects is a matter of public health importance and a significant commercial opportunity.

A potentially valuable solution to the problem is the design of aspirin derivatives capable of delaying aspirin release from occurring in the GI tract until after absorption into plasma. Such a derivative should properly be termed a prodrug. Prodrugs are therapeutic agents that are themselves inactive but on metabolism form active agents (Albert, 1958). Aspirin prodrugs were investigated for many years as a means of depressing its gastric toxicity (Jones, 1985).

The original aspirin prodrug rationale proposed that blocking the aspirin carboxylic acid, for example with an ester, would effectively abolish the chemical aspect of gastric toxicity which results from direct contact between the aspirin carboxylic acid and the gastric mucosa. Aspirin esters that are activated during the passage through the gastrointestinal epithelium are expected to exhibit greatly reduced gastric toxicity if this model is correct, even if drug release happens within the epithelial cells.

When the biochemical component of aspirin toxicity became more widely appreciated, the prodrug rationale was refined. In contrast to aspirin, its esters do not have the ability to inhibit COX. They would therefore not interrupt the synthesis of protective prostaglandins during passage through the gut wall. Then, following absorption, esterases in the blood would break the ester, releasing aspirin. The drug would later reach the gut through the systemic circulation but at a much lower concentration; aspirin is rapidly metabolised in the body and has a half-life of only 20 minutes. It is suspected that effective blockade of the COX-dependent mucosal defence systems requires a rather high concentration of aspirin. This is because aspirin is a weak inhibitor of one of the COX enzymes (COX-1) and a very weak inhibitor of the other (COX-2). In other words, aspirin inhibits both of the protective enzymes during the absorption phase but it is unlikely to achieve the required concentration to block both enzymes after distribution throughout the body following absorption (a similar kind of pharmacokinetic argument explains aspirin's selective inhibition of platelet thromboxane $A_2$ over endothelial prostacyclin in the heart (Pedersen A. K. & FitzGerald G. A. 1984)).

Aspirin prodrug esters are therefore expected to have lower GI toxicity because they would not cause topical irritancy, the first passage of aspirin through GI at high concentration would be avoided and the second distribution is likely to be at a concentration that would leave COX-2 dependent protective functions intact. The idea of such aspirin ester prodrugs is attractive since the prodrugs are not acidic during passage across the protective barrier and would not disrupt it. They are also expected to have a smaller impact on the biochemical machinery regulating the barrier, whether activated in the epithelium or especially later after entry into the blood stream. This has the advantage that aspirin associated adverse GI effects are avoided. The drug is safer since it is not activated until after it has passed through the GI tract (FIG. 1).

Another problem with aspirin from a clinical point of view is that it is unstable towards moisture and can't therefore be formulated in solutions. Aqueous solutions of aspirin would be especially desirable in paediatric and geriatric medicine. One of the major contributors to aspirin's instability is a form of autocatalysis first described by Jencks and Pierre (1958). Aspirin has a carboxylic acid group and an acetyl group. The carboxylic acid group has the capacity to activate a nearby water molecule generating hydroxide which attacks the acetyl group. By forming an ester of aspirin the carboxylic acid group is masked and cannot engage in autocatalysis. Aspirin esters are usually more stable than aspirin and therefore have the potential to be formulated in a variety of useful ways that can't be applied to aspirin. This second advantage to aspirin esters has been well established experimentally.

On the other hand, the hypothesized theory of obviation of aspirin toxicity has never been tested because there has never been a suitable aspirin ester prodrug candidate. This is because aspirin ester prodrugs are very difficult to design. An aspirin ester of paracetamol—benorylate was on the market for about thirty years until it emerged that its administration dose to humans does not result in aspirin release (Williams et al., 1989).

The problem with aspirin esters and related derivatives is a metabolic one. Aspirin esters are converted in the body to salicylic acid rather than aspirin (Nielsen & Bundgaard, 1989). Aspirin esters are metabolised in human tissue and blood by way of the possible pathways shown in FIG. 2. An effective aspirin prodrug should be cleaved at the carrier group liberating aspirin following absorption. Rapid hydrolysis of aspirin esters happens in blood and plasma ($t_{1/2}$<1 min), but not at the desired aspirin-carrier ester bond (position B in FIG. 2). Instead, the acetyl group is cleaved (A in FIG. 2) and the resultant product is a salicylate ester, and ultimately salicylic acid. This biochemical pathway cannot produce aspirin. The ratio of salicylate to aspirin is usually greater than 99:1, regardless of the identity of the carrier group (the alcohol component of the prodrug used to form the ester with the drug carboxylic acid is known as the carrier in prodrug terminology). If you form an ester from an acid drug the part you are attaching blocks the acid chemistry but it also confers on the new entity some of its own physicochemical characteristics (et FIG. 2). This problem has elicited interest both as a pharmaceutical conundrum and a commercial opportunity. There is a substantial body of academic and patent literature in the area (See Gilmer et al., 2002 and references therein). However the vast majority of compounds referred to as aspirin prodrugs in the literature do not actually function as aspirin prodrugs in vitro or in vivo and they release the corresponding salicylate ester instead (Nielsen & Bundgaard, 1989).

In order for an aspirin ester to function as a prodrug hydrolysis in blood cleavage has to occur at the carrier ester bond. The design challenge is that esterifying aspirin causes the wrong ester group to undergo hydrolysis in the presence of human plasma. The problem was first explained by Bungaard and Nielsen (1989). When aspirin enters the blood stream its acetyl group is hydrolysed by the dominant esterase enzyme in human plasma-butyrylcholinesterase (BuChE), resulting in the formation of salicylic acid. Aspirin is negatively charged at blood pH and butyrylcholinesterase is not actually at its most efficient when processing negatively charged substrates. By esterifying aspirin the negative charge (which suppresses metabolism) is removed and the acetyl group becomes a much better substrate for butyrylcholinsterase. Introduction of the new ester group therefore greatly accelerates the rate of metabolism of the existing acetyl ester. For example, aspirin has a half-life of around one hour in dilute plasma but aspirin esters undergo the same deacetylation process with a half-life of less than one minute: neutral phenylacetates, such as aspirin esters are among the most efficiently hydrolysed substrate types of butyrylcholinesterase. An interpretation of this in terms of basic enzymology is that the aspirin ester fits the enzyme better than aspirin itself. Bundgaard recognised that in order for metabolism to occur at the correct point, the carrier group has to have a structure of competing complementarity to the acetyl group i.e. it has to be at least as attractive a substrate for the BuChE enzyme as the acetyl group. Even better carrier groups can be envisaged that promote their own hydrolysis while at the same time suppressing hydrolysis of the neighbouring acetyl group. The butyrylcholinesterase enzyme takes its name from its efficiency in hydrolysing esters of choline. Neilsen and Bungaard studied glycolamide esters of aspirin where the carrier group was designed to mimic choline so that its detachment might successfully compete with acetyl group hydrolysis. The glycolamides were only partially successful with the most successful example being hydrolysed around 50% in both the desirable and unproductive directions (routes A and B in FIG. 2). Nielsen and Bundgaard's work established the important principle that a successful aspirin prodrug requires a carrier group that fits human plasma esterase in a manner that overrides its preference for the acetyl group. This turns out to be a highly demanding requirement to which their response was only partly adequate. However, apart from the technology described herein, the glycolamides are the only known compounds which can even partly be described as true aspirin prodrugs.

Another strategy that has been adopted from time to time is to design esters where the aspirin-carrier bond is so labile that it breaks before esterases can attack the acetyl group. The problem with this approach is that aspirin is already quite unstable towards hydrolysis by water and other nucleophiles at its acetyl group. Introducing a second chemically active ester has the effect of heightening the reactivity of the acetyl group (as well as adding another point of lability). Aspirin esters deliberately intended to undergo cleavage by chemical stimuli such as water therefore have the obvious flaw that they are likely to encounter such stimuli during storage and are therefore susceptible to degradation on the shelf. This negates one of the advantages of aspirin ester prodrugs in the first place—that they are more stable than aspirin towards moisture. Prodrugs designed to be cleaved in response to generic chemical stimuli tend also to break under conditions found in the GIT, which they would meet before absorption.

Interest in the aspirin prodrug area has intensified with the advent of the so-called nitric oxide (NO)-aspirins, which are a type of aspirin ester but with an NO.-releasing moiety attached to the carrier group. The main rationale for the development of NO-aspirins is that NO. promotes mucosal defence, offsetting the damage caused by aspirin (Fiorucci and Del Soldato, 2003). This concept is now well accepted in the biomedical community. Nitric oxide and aspirin also have complementary and sometimes synergistic pharmacological effects so the combination is expected to show a greater range of pharmacological effects than aspirin alone. NO release protects the stomach from aspirin induced gastric erosion by promoting blood flow and reducing leucocyte adhesion whiles its antithrombotic properties through the GMP pathway potentiate the antiplatelet effects arising from COX-1 inhibition by aspirin. It is thus considered reasonable to link them as an ester in an attempt to produce a mutual prodrug of aspirin and nitric oxide. NCX-4016 (NicOx SA, France) is a prototype compound for NO-aspirin drugs (WO 95/030641, WO 97/16405, WO97/16405, WO0044705). It produces NO in vivo and has anti-platelet effects. NCX-4016 exhibits greater gastric tolerability than aspirin in several animal modes. NCX-4016 began preclinical development in 1996 and since 2002 has been evaluated in the treatment of cardiovascular disorders (e.g. Peripheral Arterial Occlusive Disease (PAOD) (Phase II)), colon cancer prophylaxis (Phase I) and cancer pain.

NCX-4016 was one of the most widely touted pharmaceutical developments of the past decade and was regarded as a significant biomedical advance (see for example Levin, 2004). However, as an NO.-aspirin prodrug, NCX-4016 appears to have a significant design flaw. The key test for an aspirin ester prodrug is whether it hydrolysed to aspirin or its salicylate ester when it is incubated in human plasma or blood. NCX-4016 is an aspirin ester of a substituted phenol. There are no published data on the hydrolysis pattern of NCX-4016 in human plasma but there are for similar esters— the aspirin ester of paracetamol (benorylate—Williams et al, 1989), the aspirin ester of guicaol (Qu et al., 1990), and the aspirin ester of phenol (Nielsen & Bundgaard, 1989; also see Table 8). None of these compounds produced more than 0.5% aspirin when incubated in relevant biological matrices. There is therefore no direct evidence that NCX4016 can or should produce aspirin. In vivo and in vivo metabolic studies on the compound refer only to salicylate metabolites (Carini et al., 2002). Furthermore, COX inhibition with NCX-4016 is less extensive than with aspirin. This is a significant deficiency because platelet COX-inhibition needs to be quite complete to prevent human platelet aggregation. Another recent study suggests that NCX-4016 may act directly on its target without the release of aspirin (Corazzi et al., 2005). There have been a number of other recent efforts to design compounds capable of liberating both aspirin and nitric oxide in human tissue. The results have been disappointing. All reported compounds undergo hydrolysis along the typical salicylate pathway and fail to liberate significant amounts of aspirin though they are potentially capable of releasing nitric oxide (Gilmer et al., 2007; Valezquez et al., 2005; Cena et al., 2003).

International Publication No. WO9403421 describes salicylate esters of the clinically used isosorbide nitrate, ISMN. The compound described is isosorbide-mono-nitrate aspirinate (ISMNA) and its potential use in a transdermal patch is discussed.

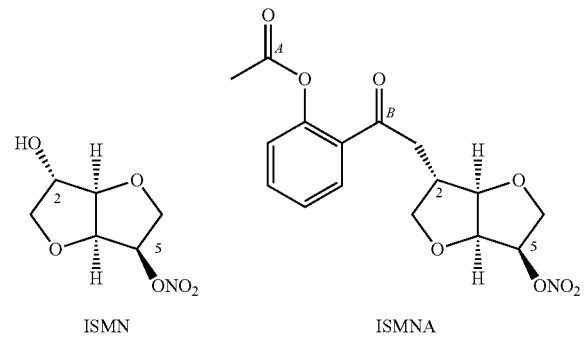

ISMN ISMNA

The compound was said to be useful for its antianginal and platelet washing properties. Chemical hydrolysis studies were reported to show degradation with production of isosorbide-mono-nitrate (ISMN), salicylic acid and aspirin which expressed platelet washing and anti-angina activities. However, it was not expected that ISMNA could act as a viable aspirin prodrug because no other aspirin ester had been shown to act as an aspirin prodrug, apart from the glycolamides, and these were very deliberately designed to be complementary to plasma BuChE. However ISMNA turned out to be a potent inhibitor of platelet aggregation in rabbit tissue in vitro and it was later shown that ISMNA is efficiently converted to aspirin by rabbit plasma esterases. It was tested in an oral study in dogs in which it was compared with aspirin in two of aspirin's pharmacological hallmarks: inhibition of the biosynthesis of thromboxane (a biochemical that stimulates platelets to aggregate) and functional inhibition of platelet aggregation. ISMNA showed weak effects on both markers indicating that it released only small amounts of aspirin in the dog. By incubating ISMNA in dog blood and monitoring its hydrolysis we were able to show that it is not converted effectively to aspirin by dog esterases because of differences between the esterases in dog and rabbit blood. Later it emerged that ISMNA is not hydrolysed productively in human plasma either. In human plasma solution and in human blood in vitro, ISMNA produces >90% salicylate and <10% aspirin. ISMNA is correspondingly much less potent than aspirin as an inhibitor of platelet aggregation in human whole blood and human platelet rich plasma (its IC50 is 85 µM compared with 5 µM for aspirin in human platelet aggregation to arachidonic acid in platelet rich plasma). The results taught that for an ester of aspirin, ability to inhibit platelet aggregation or thromboxane synthesis correlates with ability to produce aspirin: an inefficient prodrug makes for an ineffective inhibitor of platelet aggregation. The low level of aspirin release and lack of potency precluded isosorbide-mono-nitrate aspirinate (ISMNA) from being a viable drug candidate for humans.

International Publication No. WO9817673 discloses the di-aspirinate of isosorbide and two mono-aspirinate esters of isosorbide, namely isosorbide-2-aspirinate and isosorbide-5-aspirinate. Isosorbide-di-aspirinate (ISDA), the principal subject of WO9817673, was not ostensibly any different from the many other earlier ester prodrug candidates that have been tested.

ISDA

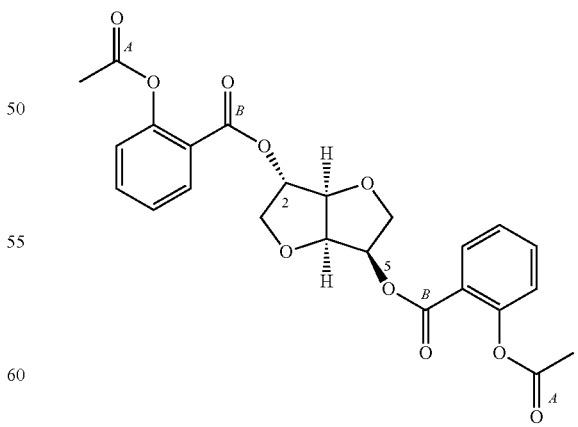

Moreover, the person skilled in the art would not have expected Isosorbide-di-aspirinate (ISDA) to function as a viable aspirin prodrug and would have had no chemical or biochemical reason to believe that hydrolysis would lead to anything other than acetyl group cleavage and so ultimately salicylic acid. It was very surprising therefore when we were able to show in our own laboratory that ISDA inhibits platelet aggregation in rabbit platelet rich plasma. It also had an inhibitory effect on thromboxane synthesis following oral administration to a group of dogs (Gilmer et al., 2003). The aspirin-like properties indicated that the hydrolysis of ISDA in plasma leads to some aspirin. ISDA was shown to undergo rapid hydrolysis when incubated in phosphate buffered human plasma solutions to produce approximately 60% aspirin (Gilmer et al., 2002). The remaining 40% of the compound was hydrolysed along the unproductive salicylate pathway. The study indicated that a specific enzyme present in human plasma catalyses aspirin release from isosorbide diaspirinate (ISDA). It was confirmed that butyrylcholinesterase was the human plasma enzyme involved. Closely related horse plasma butyrylcholinesterase generated only 11% aspirin. Gilmer et al (2001, 2002) further describe the hydrolysis characteristics and biological effects of isosorbide-mono-nitrate aspirinate (ISMNA) and isosorbide-di-aspirinate (ISDA).

The diaspirinate ester ISDA and the glycolamide esters of Nielsen and Bungaard are the only esters in the chemical literature that can to a significant extent act as aspirin prodrugs in human plasma. Compounds not producing aspirin as a hydrolysis product are better classified as salicylic acid prodrugs. For example, in the present context, ISMNA is an aspirin prodrug only in rabbit tissue but it is a salicylic acid prodrug in human blood.

There is a pressing need for better aspirin prodrug compounds because of their intrinsic therapeutic potential and because of the demand for compounds capable of releasing both aspirin and nitric oxide. A nitric-oxide releasing aspirin ester must in the first instance be an ester capable of undergoing conversion to aspirin in the key plasma hydrolysis model. In particular it is desirable to provide aspirin prodrug compounds which resist aqueous hydrolysis and α-chymotrypsin, yet will undergo rapid hydrolysis in the presence of human plasma to liberate aspirin and potentially other pharmacologically active moieties, in particular nitric oxide.

SUMMARY OF THE INVENTION

According to the invention there is provided an isosorbide aspirinate compound having the general structure as shown in general formula (I*)

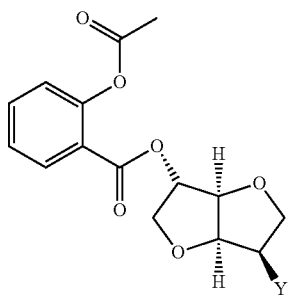

(I*)

wherein Y is a $C_1$-$C_8$ alkyl ester, a $C_1$-$C_8$ alkoxy ester, a $C_3$-$C_{10}$ cycloalkyl ester, an arylester, a $C_1$-$C_8$ alkylaryl ester or —C(O)OR$^{ring}$, wherein R$^{ring}$ is a 5-membered aromatic or nonaromatic 5-member ring having at least one heteroatom substituted for a carbon of the ring system, which can be unsubstituted or substituted with at least one nitric oxide releasing group.

The present invention also relates to pharmaceutically acceptable salts and/or hydrates of the compounds described herein.

Used herein, the term "alkyl" includes any of a series of univalent groups of the general formula RC(O)R, or more specifically —OC(O)$C_nH_{2n+1}$, which is an ester derived from aliphatic hydrocarbons. The alkyl chains of the alkyl ester chains can be straight or branched wherein the methyl group (—$CH_3$) represents a $C_1$ alkyl group, ethyl (—$C_2H_5$) represents a $C_2$ alkyl group, propyl (—$C_3H_7$) represents a $C_3$ alkyl group, butyl (—$C_4H_9$) represents a $C_4$ alkyl group and pentyl (—$C_5H_7$) represents a $C_5$ alkyl group.

The term "alkoxy ester" includes a group having the general formula RC(O)OR, or more specifically —OC(O)O$C_nH_{2n+1}$, wherein $C_nH_{2n+1}$ is an alkyl chain which can be straight or branched wherein the methyl group (—$CH_3$) represents a $C_1$ alkyl group, ethyl (—$C_2H_5$) represents a $C_2$ alkyl group, propyl (—$C_3H_7$) represents a $C_3$ alkyl group, butyl (—$C_4H_9$) represents a $C_4$ alkyl group and pentyl (—$C_5H_7$) represents a $C_5$ alkyl group.

The term "cycloalkyl ester" means that the $C_nH_{2n+1}$ group of the above formula is a cyclic alkyl group such as cyclopropane, cyclobutane, cyclopentane etc.

The term "aryl ester" is taken to mean RC(O)Ar, wherein Ar represents any functional group or substituent derived from a simple aromatic ring for example a benzene ring, toluene, xylene, benzoic acid, benzoate, nicotinate, chlorobenzene or other halobenzene groups.

The term "esters of 5 membered heterocyclic rings", represents any ester functionality represented by —C(O)OR$^{ring}$ wherein, R$^{ring}$ is a 5-membered aromatic or nonaromatic 5-member ring having at least one heteroatom substituted for a carbon of the ring system. Suitably R$^{ring}$ groups may be selected from the group consisting of: thiophenes, thiadiazolines, pyrroles, imidazoles, thiazoles, pyrazoles, 4,5-dihydropyrroles, imidazolidin-2-ones, pyrazines, 4,5-dihydrothiophenes and imidazolidin-2-thiones. Preferred R$^{ring}$ are heterocyclic rings

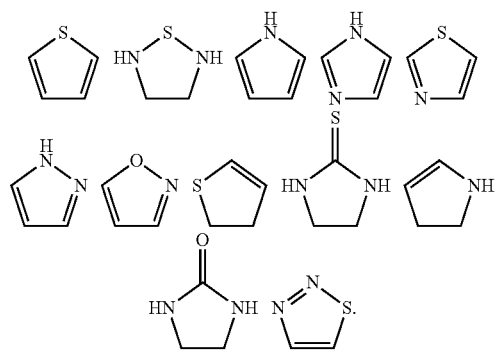

The preferred —C(O)OR$^{ring}$ groups of the invention are iso-oxazoleoate, oxazoleoate or thiadiazoleoate.

Suitably, all of these compounds actively release aspirin in human plasma to a degree. Some of the compounds have been shown to have better activity than other compounds whereas some compounds have a lesser activity depending on the nature of the substituent chosen as Y. Some of the compound release NO in addition to aspirin.

Suitably, the preferred compounds of the invention have activity of great or equal to 15% aspirin released in human plasma.

The nitric oxide releasing group of the compounds of the invention may comprise a nitrate ester, a $C_1$ to $C_8$ alkyl nitrate ester, a $C_3$-$C_{10}$ cycloalkyl nitrate ester or a $C_1$-$C_8$ alkyl nitrate ester.

In one embodiment, the isosorbide aspirinate compound has the general structure as shown in general formula (I)

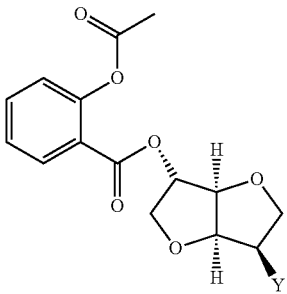

(I)

wherein Y is a $C_1$-$C_8$ alkyl ester, a $C_1$-$C_8$ alkoxy ester, a $C_3$-$C_{10}$ cycloalkyl ester, a $C_1$-$C_8$ cycloalkoxy ester, which can be unsubstituted or substituted with $ONO_2$; or an aryl ester or a $C_1$-$C_8$ alkyl aryl ester, which can be unsubstituted or substituted with at least one nitric oxide releasing group.

However, most preferred are compounds having esters comprising 5-membered heterocyclic rings which may be selected from the group consisting of oxazoleoate, isoxazoleate and thiadiazoleoate.

In a preferred embodiment, the isosorbide aspirinate compound has the general structure as shown in general formula (I)

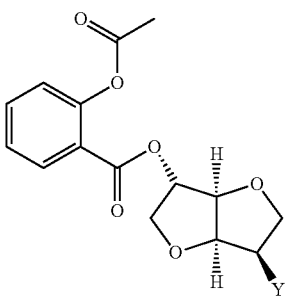

(I)

wherein Y is a $C_1$-$C_8$ alkyl ester or a $C_1$-$C_8$ alkoxy ester, which can be unsubstituted or substituted with $ONO_2$; or a $C_3$-$C_{10}$ cycloalkyl ester or a $C_1$-$C_8$ cycloalkoxy ester, which can be unsubstituted or substituted with $ONO_2$; or an unsubstituted or a substituted arylester, alkylaryl ester, benzoate, a nicotinate, oxazoleoate, isoxazoleate, thiadiazoleoate group, which may be substituted by at least one of the group comprising hydroxide, —Cl, —Br, a $C_1$-$C_8$ alkyl, benzyl, a $C_1$-$C_8$ alkoxy, benzyloxy, —NHC(O)R, —NH$_2$, —NO$_2$, —ONO$_2$, —(CH$_2$)$_n$ONO$_2$, —OC(O)[(CH$_2$)$_m$]$_{cyclic}$ONO$_2$, —OCOArONO$_2$, —OCOAr (CH$_2$)$_n$ONO$_2$ or a $C_1$-$C_5$ haloalkyl ester, wherein R is a $C_1$-$C_8$ alkyl or a $C_1$-$C_8$ alkoxy group, n=1-8, m=3-10.

According to the invention there is provided anisosorbide aspirinate compound having the general structure as shown in general formula (I*)

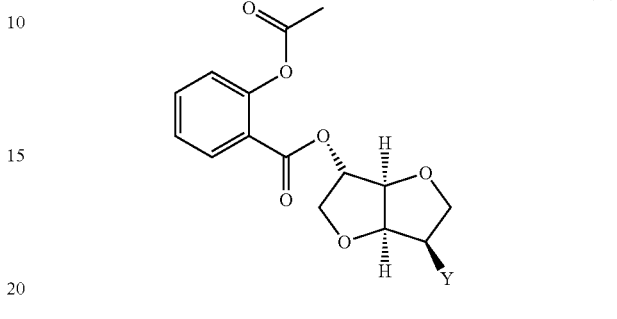

(I*)

wherein Y is

—C(O)OR$^{ring}$, wherein R$^{ring}$ is a 5-membered aromatic or nonaromatic 5-member ring having at least one heteroatom substituted for a carbon of the ring system, which can be unsubstituted or substituted with at least one nitric oxide releasing group.

In a preferred embodiment, the nitric oxide releasing group may be selected from the group consisting of: —NO$_2$, —ONO$_2$, —(CH$_2$)$_n$ONO$_2$, —OC(O)[(CH$_2$)$_m$]$_{cyclic}$ONO$_2$, —OCOArONO$_2$, —OCOAr (CH$_2$)$_n$ONO$_2$.

Particularly, preferred compounds include an isosorbide aspirinate compound having the general structure as shown in general formula (I*)

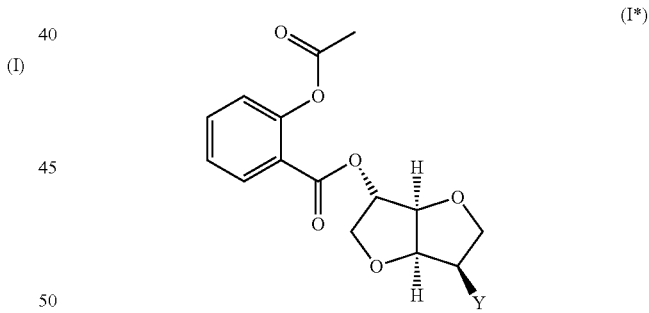

(I*)

wherein Y is

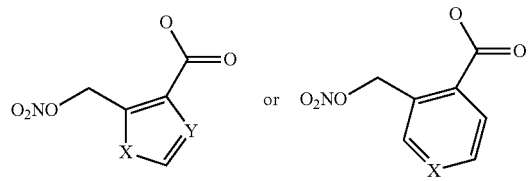

wherein X and Y are independent selected from O, S and N.

In another embodiment, there is provided a compound which has a general structure as shown in general formula (I)

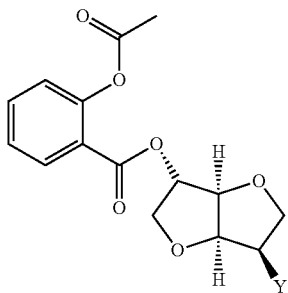

(I)

wherein Y is a $C_1$-$C_8$ alkyl ester or a $C_1$-$C_8$ alkoxy ester, which can be unsubstituted or substituted with $ONO_2$; or an unsubstituted or a substituted arylester, alkylaryl ester, benzoate, nicotinate, oxazoleoate, isoxazoleate, thiadiazoleoate group, which may be substituted by at least one of the group comprising hydroxide, —Cl, —Br, a $C_1$-$C_8$ alkyl, benzyl, a $C_1$-$C_8$ alkoxy, o-benzyloxy, —NHC(O)R, —$NH_2$, —$NO_2$, —$ONO_2$, —$(CH_2)_nONO_2$, —$OC(O)[(CH_2)_m]_{cyclic}ONO_2$, —$OCOArONO_2$, —$OCOAr(CH_2)_nONO_2$ or a $C_1$-$C_5$ haloalkyl ester, wherein R is a $C_1$-$C_8$ alkyl or a $C_1$-$C_8$ alkoxy group, n=1-8, m=3-10.

Other preferred compounds are illustrated by the general structure as shown in general formula (I)

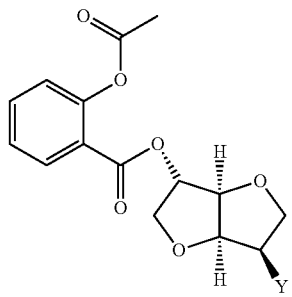

(I)

wherein Y is a $C_1$-$C_8$ alkoxy ester, which can be unsubstituted or substituted with $ONO_2$; or a $C_3$-$C_{10}$ cycloalkyl ester or a $C_1$-$C_8$ cyclo alkoxy ester, which can be unsubstituted or substituted with $ONO_2$; or an unsubstituted or a substituted benzoate or nicotinate group, which may be substituted by at least one of the group comprising hydroxide, a $C_1$-$C_8$ alkyl, benzyl, a $C_1$-$C_8$ alkoxy, benzyloxy, —NHC(O)R, —$NH_2$, —$NO_2$, —$ONO_2$, —$(CH_2)_nONO_2$, —$OC(O)[(CH_2)_m]_{cyclic}ONO_2$, —$OCOArONO_2$, —$OCOAr(CH_2)_nONO_2$ or a $C_1$-$C_5$ haloalkyl ester, wherein R is a $C_1$-$C_8$ alkyl or a $C_1$-$C_8$ alkoxy group, n=1-8, m=3-10.

Further preferred compounds are illustrated by the general structure as shown in general formula (I)

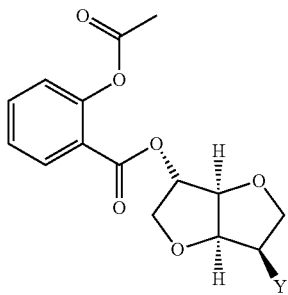

(I)

wherein Y is a $C_1$-$C_8$ alkyl ester or a $C_1$-$C_8$ alkoxy ester, which can be unsubstituted or substituted with $ONO_2$; or a $C_3$-$C_{10}$ cycloalkyl ester or a $C_1$-$C_8$ cyclo alkoxy ester, which can be unsubstituted or substituted with $ONO_2$; or an unsubstituted or a substituted aryl ester, alkyl aryl ester, benzoate or nicotinate group, which may be substituted by at least one of the group comprising hydroxide, a $C_1$-$C_8$ alkyl, benzyl, a $C_1$-$C_8$ alkoxy, benzyloxy, —NHC(O)R, —$NH_2$, —$NO_2$, —$ONO_2$, —$(CH_2)_nONO_2$, —$OC(O)[(CH_2)_m]_{cyclic}ONO_2$, —$OCOArONO_2$, —$OCOAr(CH_2)_nONO_2$ or a $C_1$-$C_5$ haloalkyl ester, wherein R is a $C_1$-$C_8$ alkyl or a $C_1$-$C_8$ alkoxy group, n=1-8, m=3-10.

Other preferred compounds are illustrated by the general structure as shown in general formula (I)

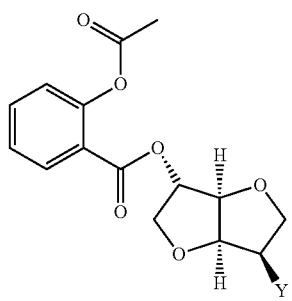

(I)

wherein Y is a $C_1$-$C_8$ alkoxy ester, which can be unsubstituted or substituted with $ONO_2$; or an unsubstituted or a substituted benzoate or nicotinate group, which may be substituted by at least one of the group comprising hydroxide, —Cl, —Br, a $C_1$-$C_8$ alkyl, benzyl, a $C_1$-$C_8$ alkoxy, o-benzyloxy, —NHC(O)R, —$NH_2$, —$NO_2$, —$ONO_2$, —$(CH_2)_nONO_2$, —$OC(O)[(CH_2)_m]_{cyclic}ONO_2$, —$OCOArONO_2$, —$OCOAr(CH_2)_nONO_2$ or a $C_1$-$C_5$ haloalkyl ester, wherein R is a $C_1$-$C_8$ alkyl or a $C_1$-$C_8$ alkoxy group, n=1-8, m=3-10.

In a preferred embodiment, the isosorbide aspirinate compound may have the general structure as shown in general formula (I)

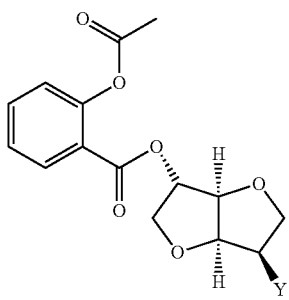

(I)

wherein Y is a $C_1$-$C_8$ alkyl ester or a $C_1$-$C_8$ alkoxy ester, which can be unsubstituted or substituted with $ONO_2$; or an unsubstituted or a substituted aryl ester, alkyl aryl ester, benzoate or nicotinate group, which may be substituted by at least one of the group comprising hydroxide, —Cl, —Br, a $C_1$-$C_8$ alkyl, benzyl, a $C_1$-$C_8$ alkoxy, benzyloxy, —NHC(O)R, —$NH_2$, —$NO_2$, —$ONO_2$, —$(CH_2)_nONO_2$, —OC(O)[$(CH_2)_m]_{cyclic}ONO_2$, —$OCOArONO_2$, —$OCOAr(CH_2)_nONO_2$ or a $C_1$-$C_5$ haloalkyl ester, wherein R is a $C_1$-$C_8$ alkyl or a $C_1$-$C_8$ alkoxy group, n=1-8, m=3-10. Where benzyloxy substituent is used on an aryl ring, it is preferred that it is an o-benzyloxy substituent.

In a particularly preferred embodiment, the compound may have the general structure as shown in general formula (I)

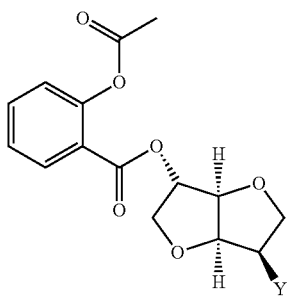

(I)

wherein Y is a $C_1$-$C_8$ alkyl ester, which can be unsubstituted or substituted with $ONO_2$; or an unsubstituted or a substituted benzoate or nicotinate group, which may be substituted by at least one of the group comprising hydroxide, a $C_1$-$C_8$ alkyl, benzyl, a $C_1$-$C_8$ alkoxy, benzyloxy, —NHC(O)R, —$NH_2$, —$NO_2$, —$ONO_2$, —$(CH_2)_nONO_2$, —OC(O)[$(CH_2)_m]_{cyclic}ONO_2$, —$OCOArONO_2$, —$OCOAr(CH_2)_nONO_2$ or a $C_1$-$C_5$ haloalkyl ester, wherein R is a $C_1$-$C_8$ alkyl or a $C_1$-$C_8$ alkoxy group, n=1-8, m=3-10. Where benzyloxy substituent is used on an aryl ring, it is preferred that it is an o-benzyloxy substituent.

In a still further embodiment the compounds may have the general structure as shown in general formula (I)

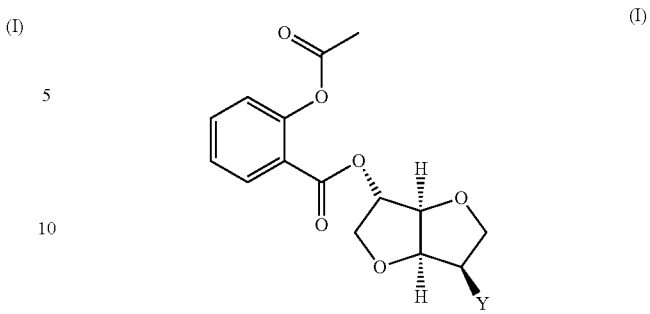

(I)

wherein Y is an unsubstituted or a substituted benzoate or nicotinate group, which may be substituted by at least one of hydroxide, a $C_1$-$C_8$ alkyl, $C_1$-$C_8$ alkyoxy, benzyloxy, —$(CH_2)_nONO_2$ (n=1-8), $C_3$-$C_{10}$ cycloalkyl ester or haloalkyl ester. Where benzyloxy substituent are found on the compound, it is preferred to be o-benzyloxy.

Suitably, the compounds of the invention may have the general structure as shown in general formula (I)

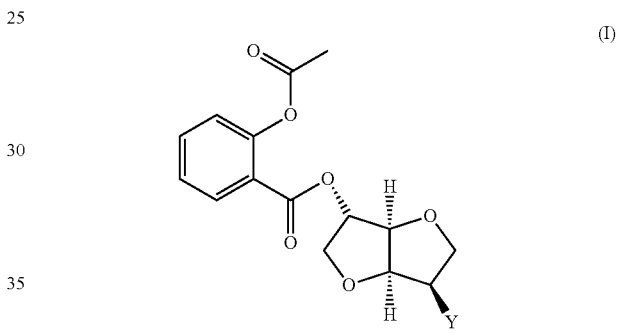

(I)

wherein Y is an unsubstituted or a substituted benzoate or nicotinate group, which may be substituted by at least one of hydroxide, $C_1$-$C_8$ alkyl, $C_1$-$C_8$ alkyoxy, o-benzyloxy, —$(CH_2)_nONO_2$ (n=1-8), $C_3$-$C_{10}$ cycloalkyl ester or haloalkyl ester.

Where a haloalkyl ester group is a feature of the compounds, the halo substituent may be Cl, Br or F.

In an embodiment where the compound comprises a haloalkyl ester, the halo substituent is suitably Cl, Br or F. Chlorine and bromine are the most preferred halo substituents. However, haloalkyl esters having Br substituents are particularly preferred.

Suitably, the compounds of the invention have a high degree of complementarity to the active site of the human carboxylesterases and so steers hydrolysis along the ideal pathway, liberating aspirin.

Advantageously, the compounds can be specifically activated by more than one human enzyme, since if a patient has aberrant enzyme function with respect to one, another is likely to compensate and release aspirin.

Furthermore, the aspirin prodrug compounds are stable under conditions found in the lumen of the GI tract but breaks down rapidly after absorption into the bloodstream to aspirin.

Further advantages arise from these compounds since they are stable towards moisture and so can successfully be used in formulations where moisture may be encountered. A moisture stable aspirin prodrug is advantageous for many reasons including the possibility of formulation in solution and transdermal forms. One of the problems with transdermal delivery of aspirin is that moisture from skin causes hydrolysis of the aspirin depot in the patch. Suitably, the moisture stable compounds will not require protective moisture-proof pharmaceutical packaging for storage.

In a preferred embodiment, the group Y may be selected from the group consisting of:

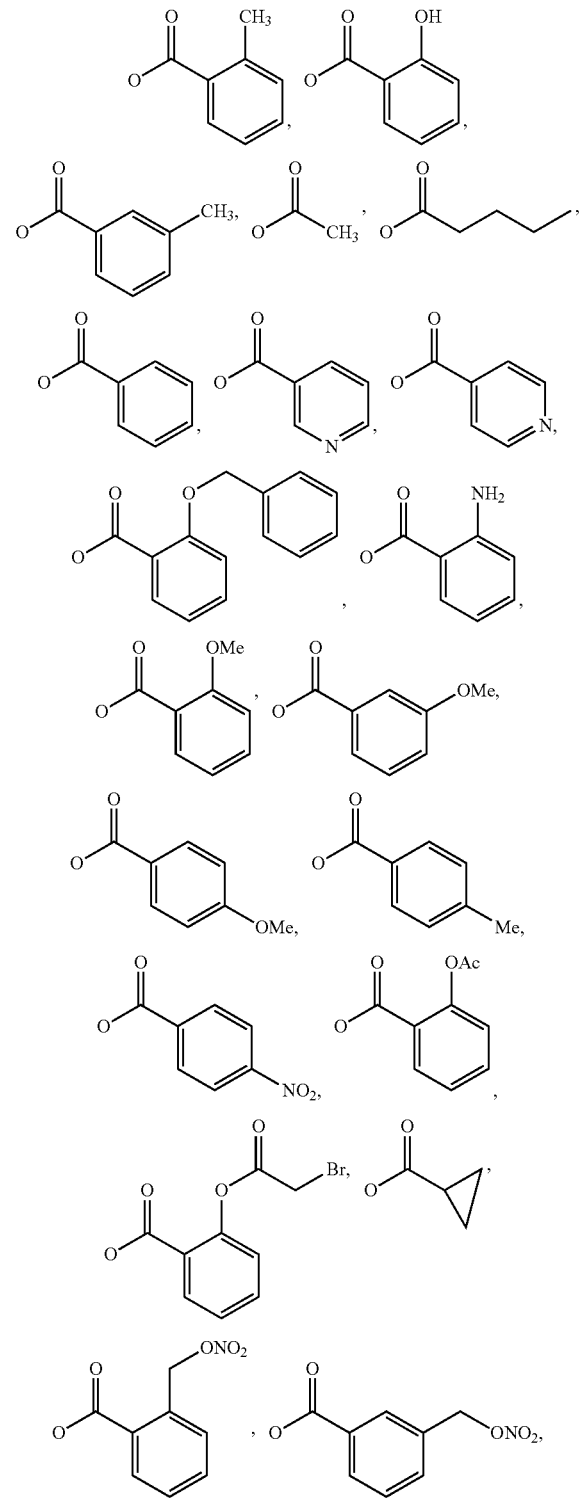

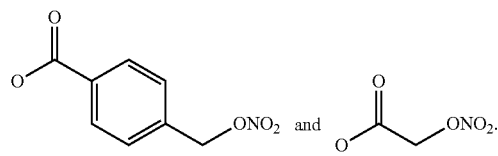

The compounds of the invention, when Y in the general formula (I) is represented by any of the these particular structures, the compounds release aspirin in human plasma to some various degree and thus all are active.

However, the compounds having a Y substituent selected from the group consisting of:

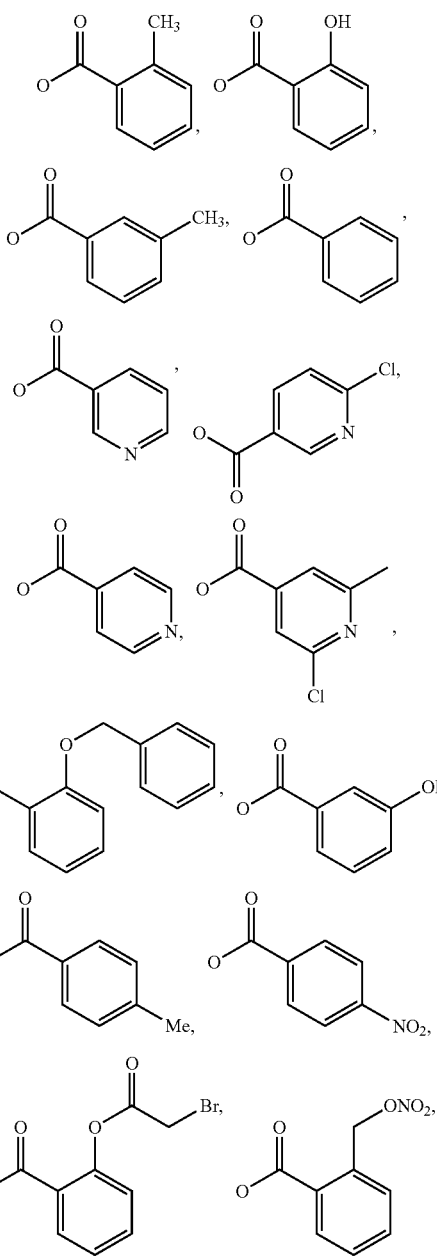

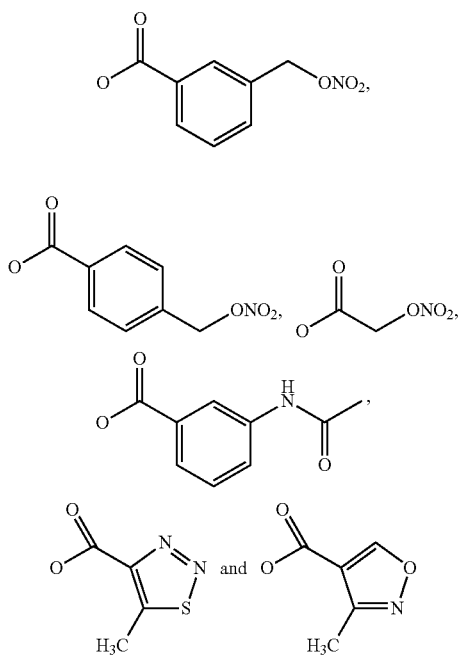

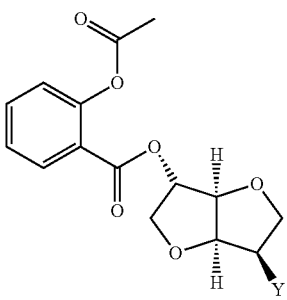

are particularly preferred, since the compounds comprising these any of these groups show activities of greater than or equal to 15% aspirin release in human plasma.

In another preferred embodiment, the compounds of the invention comprise those that have aspirin release activities greater than or equal to the 15% level, based on the amount of aspirin as a percentage of the initial ester concentration in moles measured by HPCL at peak aspirin production following addition of candidate esters to buffered human plasma at 37° C. at pH 7.4 (phosphate buffer).

In specific embodiments, the compounds may have the general structure as shown in general formula (I)

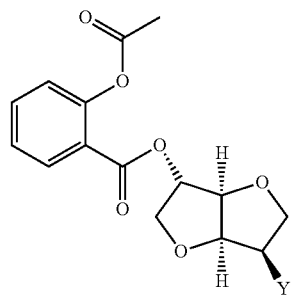
(I)

wherein Y is an unsubstituted or a substituted benzoate or nicotinate group, which may be substituted by at least one of hydroxide, methyl, benzyloxy, methoxy, —NHC(O)CH₃, —OC(O)CH₂Br, —NO₂, —OAc. —CH₂ONO₂. Where benzyloxy substituent is used on an aryl ring, it is preferred that it is an o-benzyloxy substituent.

In a specific embodiment, the compounds may have the general structure as shown in general formula (I)

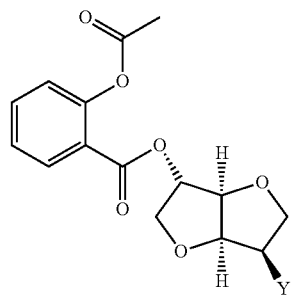
(I)

wherein Y is an unsubstituted or a substituted benzoate or nicotinate group, which may be substituted by at least one of hydroxide, —Cl, methyl, benzyloxy, methoxy, —NHC(O)CH₃, —OC(O)CH₂Br, —NO₂, —CH₂ONO₂. Where benzyloxy substituent is used on an aryl ring, it is preferred that it is an o-benzyloxy substituent.

The most preferred isosorbide aspirinate compounds have one of the following structures

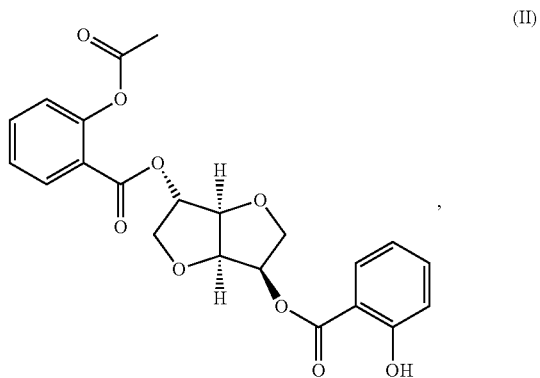
(II)

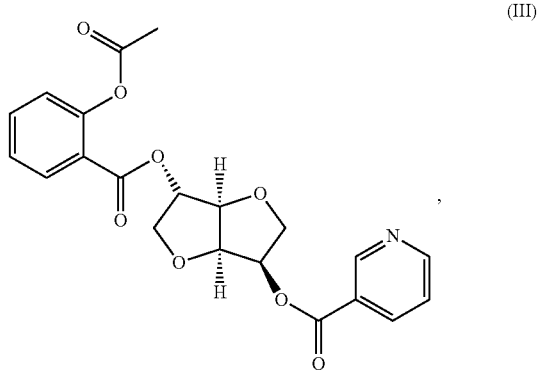
(III)

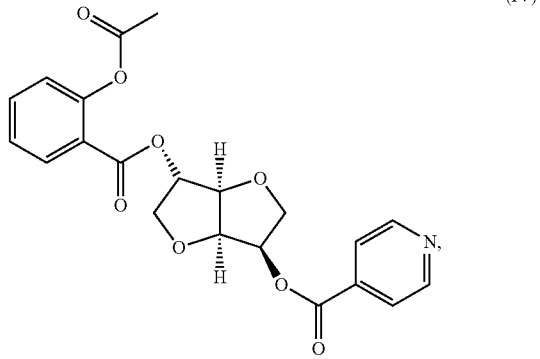
(IV)

-continued (V)

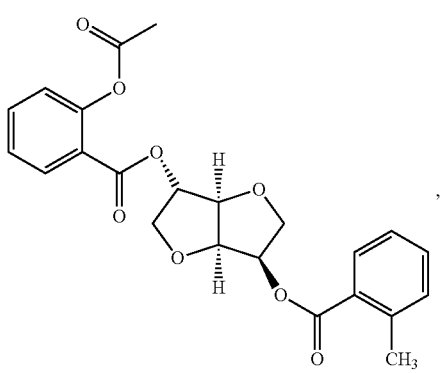

(VI)

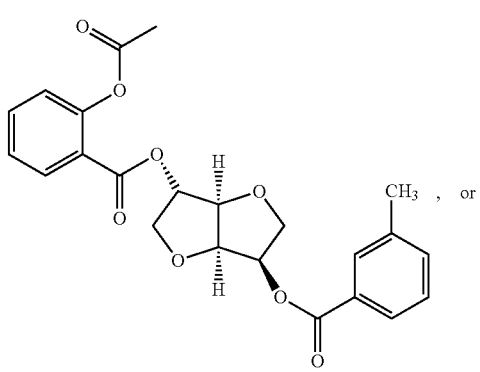, or (VII)

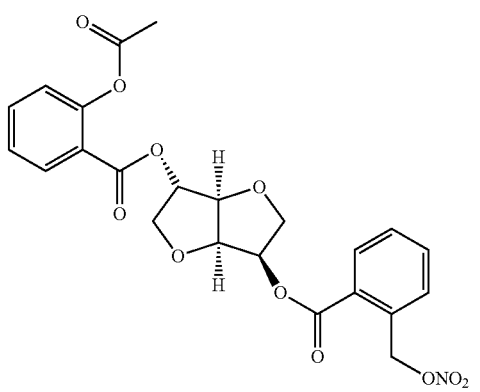

(VIII)

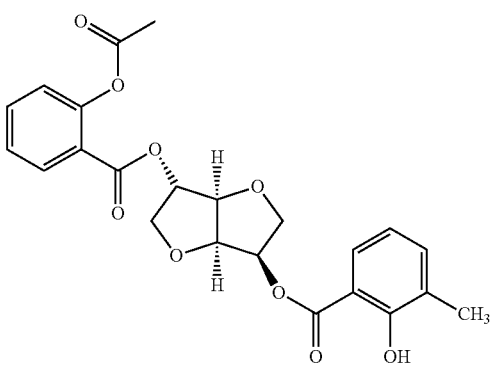

Alternatively, the isosorbide aspirinate compound may have any one of the structures selected from the group consisting of:

-continued (IX)

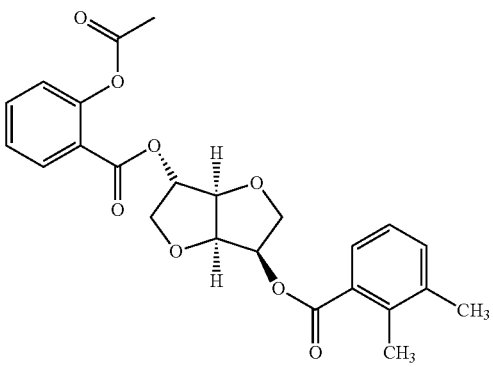

(X)

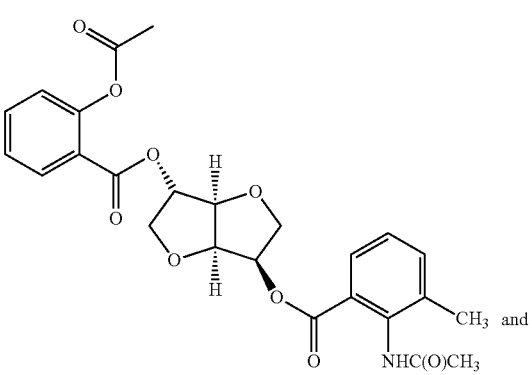 and (XI)

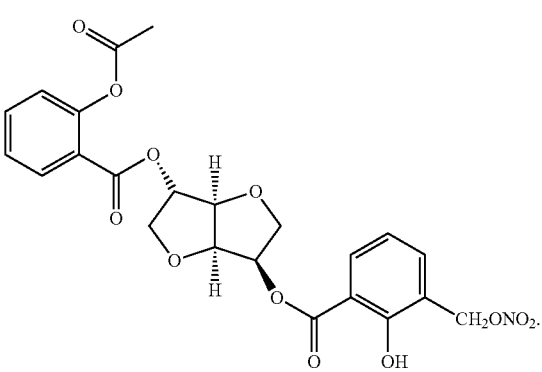

In another aspect of the invention, there is provided a carrier compound for a drug having the general structure as shown in general formula (II)

(II)

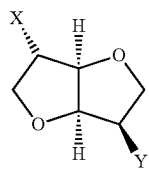

wherein Y is
a $C_1$-$C_8$ alkyl ester, a $C_1$-$C_8$ alkoxy ester, a $C_3$-$C_{10}$ cycloalkyl ester, an arylester, a $C_1$-$C_8$ alkylaryl ester or —C(O)OR$^{ring}$, wherein R$^{ring}$ is a 5-membered aromatic or nonaromatic 5-member ring having at least one heteroatom substituted for a carbon of the ring system, which can be unsubstituted or substituted with at least one nitric oxide releasing group, and X is the drug molecule.

In this aspect, a preferred embodiment provides a carrier compound for a drug having the general structure as shown in general formula (II)

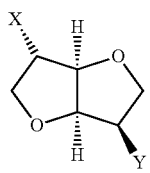

(II)

wherein Y is a $C_1$-$C_8$ alkyl ester, a $C_3$-$C_{10}$ cycloalkyl ester, an arylester or a $C_1$-$C_8$ alkyl aryl ester, which can be unsubstituted or substituted with at least one nitric oxide releasing group, and X is the drug molecule.

Preferred carriers of the invention may have the general structure as shown in general formula (II)

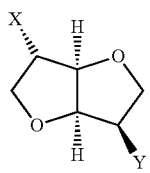

(II)

wherein Y is a $C_1$-$C_8$ alkyl ester, which can be unsubstituted or substituted with $ONO_2$; or a $C_3$-$C_{10}$ cycloalkyl ester, which can be unsubstituted or substituted with $ONO_2$; or an unsubstituted or a substituted aryl ester, alkyl aryl ester, benzoate or nicotinate group, which may be substituted by at least one of the group comprising hydroxide, a $C_1$-$C_8$ alkyl, benzyl, a $C_1$-$C_8$ alkoxy, benzyloxy, —NHC(O)R, —NH$_2$, —NO$_2$, —ONO$_2$, —(CH$_2$)$_n$ONO$_2$, —OC(O)[(CH$_2$)$_m$]$_{cyclic}$ONO$_2$, —OCOArONO$_2$, —OCOAr (CH$_2$)$_n$ONO$_2$ or a $C_1$-$C_5$ haloalkyl ester, wherein R is a $C_1$-$C_8$ alkyl or a $C_1$-$C_8$ alkoxy group, n=1-8, m=3-10.

In other embodiments, the carrier of the invention may have the general structure as shown in general formula (II)

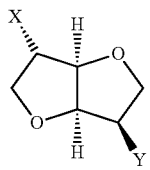

(II)

wherein Y is a $C_3$-$C_{10}$ cycloalkyl ester, which can be unsubstituted or substituted with $ONO_2$; or an unsubstituted or a substituted benzoate or nicotinate group, which may be substituted by at least one of the group comprising hydroxide, a $C_1$-$C_8$ alkyl, benzyl, a $C_1$-$C_8$ alkoxy, benzyloxy, —NHC(O)R, —NH$_2$, —NO$_2$, —ONO$_2$, —(CH$_2$)$_n$ONO$_2$, —OC(O)[(CH$_2$)$_m$]$_{cyclic}$ONO$_2$, —OCOArONO$_2$, —OCOAr (CH$_2$)$_n$ONO$_2$ or a $C_1$-$C_5$ haloalkyl ester, wherein R is a $C_1$-$C_8$ alkyl or a $C_1$-$C_8$ alkoxy group, n=1-8, m=3-10.

In compounds which comprise a haloalkyl ester functional group, the halo substituent may be Cl, Br or F, however Br is more particularly preferred.

Advantageously, the aspirin prodrug compounds of the invention resist aqueous hydrolysis and α-chymotrypsin, yet will undergo rapid hydrolysis in the presence of human plasma to liberate aspirin and potentially other pharmacologically active moieties. The preferred compounds of the invention liberate nitric oxide in addition to aspirin.

Thus in this aspect, the compounds of the invention are advantageous since they provide better aspirin prodrug compounds, in particular a prodrug compound capable of releasing both aspirin and nitric oxide. Prodrug devices capable of releasing both aspirin and nitrous oxide (NO) are particularly advantageous. Such compounds are likely to be less toxic but have a greater spectrum of pharmacological actions and efficacy than their individualized components, because aspirin and nitric oxide have synergistic effects in cardiovascular disease and cancer applications.

A nitric-oxide releasing aspirin ester must in the first instance be an ester capable of undergoing conversion to aspirin in the key plasma hydrolysis model or similar biologically relevant model. The carrier of the invention may have a nitric oxide releasing group which comprises a nitrate ester, a $C_1$ to $C_8$ alkyl nitrate ester, a $C_3$-$C_{10}$ cycloalkyl nitrate ester or a $C_1$-$C_8$ alkyl nitrate ester.

Further advantages result from the fact that the prodrugs of the invention are stable in the presence of typical digestive proteases and towards enzymes found in mucosal CACO-2 cells, but may be hydrolysed to aspirin by human esterases especially BuChE and CE-2. In this aspect, the carrier may have the general structure as shown in general formula (II)

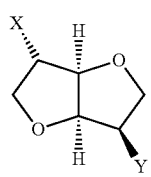

(II)

wherein Y is a $C_1$-$C_8$ alkyl ester, which can be unsubstituted or substituted with $ONO_2$; or a $C_3$-$C_{10}$ cycloalkyl ester, which can be unsubstituted or substituted with $ONO_2$; or an unsubstituted or a substituted arylester, alkylaryl ester, benzoate, a nicotinate, oxazoleoate, isoxazoleate, thiadiazoleoate group, which may be substituted by at least one of the group comprising hydroxide, —Cl, —Br, a $C_1$-$C_8$ alkyl, benzyl, a $C_1$-$C_8$ alkoxy, benzyloxy, —NHC(O)R, —NH$_2$, —NO$_2$, —ONO$_2$, —(CH$_2$)$_n$ONO$_2$, —OC(O)[(CH$_2$)$_m$]$_{cyclic}$ONO$_2$, —OCOArONO$_2$, —OCOAr (CH$_2$)$_n$ONO$_2$ or a $C_1$-$C_5$ haloalkyl ester, wherein R is a $C_1$-$C_8$ alkyl or a $C_1$-$C_8$ alkoxy group, n=1-8, m=3-10 and X is the drug molecule Suitably, the carriers of the invention steer hydrolysis to the correct point because of their complementarity with the active sites of human esterases.

In a particularly preferred embodiment, the carrier of the invention may have the general structure as shown in general formula (II)

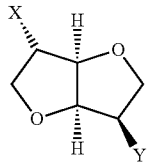

(II)

wherein Y is a $C_3$-$C_{10}$ cycloalkyl ester, which can be unsubstituted or substituted with $ONO_2$; or an unsubstituted or a substituted benzoate or nicotinate group, which may be substituted by at least one of the group comprising hydroxide, —Cl, a $C_1$-$C_8$ alkyl, benzyl, a $C_1$-$C_8$ alkoxy, benzyloxy, —NHC(O)R, —$NH_2$, —$NO_2$, —$ONO_2$, —$(CH_2)_n ONO_2$, —$OC(O)[(CH_2)_m]_{cyclic} ONO_2$, —$OCOArONO_2$, —$OCOAr (CH_2)_n ONO_2$ or a $C_1$-$C_5$ haloalkyl ester, wherein R is a $C_1$-$C_8$ alkyl or a $C_1$-$C_8$ alkoxy group, n=1-8, m=3-10.

In the preferred compounds which comprise a haloalkyl ester functional group, the halo substituent may be Cl, Br or F, however Br is the more particularly preferred substituent In another favorable embodiment, the carrier compound may be selected from the group consisting of:

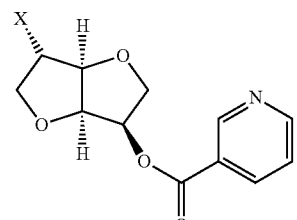

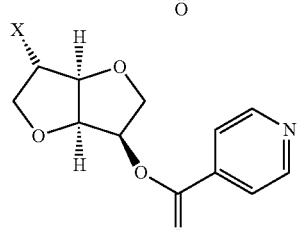

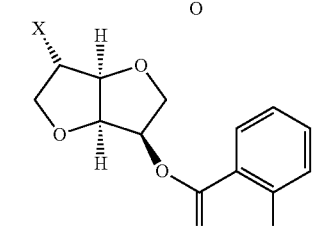

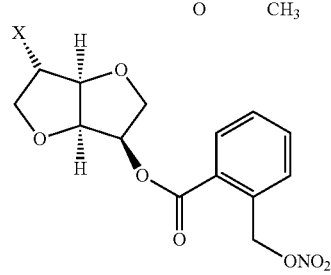

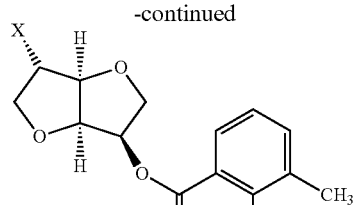

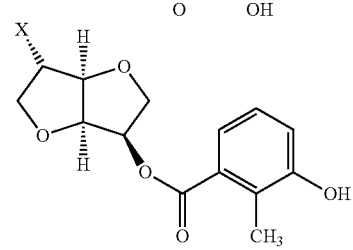

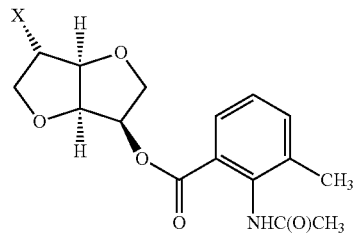

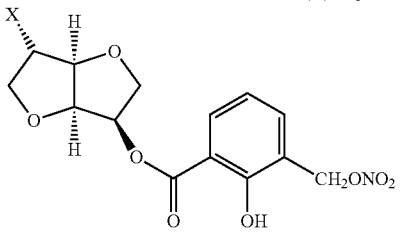

wherein X is the drug molecule to be carried in the prodrug form.

In another aspect of the invention, there is provided a drug compound comprising the carrier compound as described herein.

In another aspect still, the invention provides a pharmaceutical composition comprising a compound as defined above and at least one pharmaceutically acceptable carrier or excipient.

In a particular aspect, the compounds and/or the compositions of the invention may be used in-vivo or in-vitro to reduce constitutive platelet glycol-protein expression at a level where aspirin has no effect.

The compounds and/or the compositions of the invention may also be used in-vivo or in-vitro to induce an aspirin like effect. An aspirin like effect, for example, is a reduction in anti-platelet activity or the inhibition of COX products such as thromboxane A2 or malondialdehyde. Advantageously, the preferred compounds of the invention are more potent than aspirin itself and are greater inhibitors of human platelet aggregation and greater inhibitors of the COX downstream products (such as thromboxane $A_2$ and malondialdehyde) as well as constitutive platelet glyco-protein expression.

In another aspect the compounds of the invention can be used in the manufacture of a medicament for the treatment of diseases or conditions or symptoms including cardiovascular and cerebrovascular disorders, pain, pyretic, inflammation, cancer, Alzheimer's disease or dementia.

Aspirin causes gastric bleeding by chemically irritating the cells of the intestinal wall during absorption and by interfering with the secretion of its protective barrier. The solution to this problem is to render aspirin temporarily inert by chemically attaching a masking group that is removed later in the absorption process, away from the vulnerable surface of the GI tract. The key challenge in developing this technology was to find a masking group that is predictably and accurately removed in blood, an obstacle nobody else had been able to overcome. Essentially the invention provides for an inert form of aspirin that is activated by the body.

In a further refinement to the design, a nitric oxide-precursor was incorporated into the carrier group to provide further compounds that can release NO along with aspirin. Such dual prodrugs therefore potentially interfere with pathological processes at two different levels. The nitro-aspirin approach is becoming widely accepted but the technology described herein is the only technology that verifiably produces both aspirin and NO. in human tissue.

The hydrolysis of isosorbide-di-aspirinate (ISDA, 16 in Table 2) in human blood was investigated in order to find out how it produced aspirin.

Isosorbide-di-aspirinate (ISDA, 16) has four ester groups, one located on each of the two aspirin moieties, and one connecting each of these moieties to the isosorbide core. The straightforward interpretation of its aspirin production data was that one of the two aspirinate esters at positions 2 or 5 is detached by esterases directly from ISDA liberating aspirin. That is partly true but the real mechanism transpired to be more interesting and unexpected. The four ester groups in ISDA are susceptible to hydrolysis by esterases with a potentially complex array of ester metabolites. Ultimately all of these are hydrolysed down to isosorbide and salicylic acid. The hydrolysis cascade can be followed by chromatography, which allows the separation and measurement of each of the metabolites as they evolve and decay. Many experiments were conducted in which ISDA was introduced into biological media, the reaction stopped at successive time points and the metabolite mixture measured by HPLC. The plot of this data over a time course is termed a hydrolysis progress curve. Progress curves for ISDA are presented in FIGS. 3A and 3B. The curves show the disappearance of ISDA and the appearance of aspirin over time. A careful examination of these curves reveals two things: the aspirin concentration continued to rise after the parent ISDA had disappeared and secondly its peak followed the rise and disappearance of another metabolite. This was a surprising and highly significant finding for it indicated that the aspirin that appears after ISDA is added to human plasma might not be released from ISDA itself but rather from a metabolite of ISDA. Thus, all of the potential metabolites of ISDA were independently synthesised and evaluated by HPLC as aspirin prodrugs by incubating them in plasma and following their hydrolysis by HPLC. One of these, isosorbide-2-aspirinate-5-salicylate (ISAS, 2), turned out to be the most effective prodrug know to date in the key human plasma model (FIGS. 4A and B). In human plasma it is converted largely to aspirin along with the carrier isosorbide-5-salicylate. It is hydrolysed almost exclusively along this path in purified BuChE solution (FIG. 4B).

The results overall indicated that isosorbide-di-aspirinate (ISDA, 16) acts as a precursor to a true aspirin prodrug, its metabolite isosorbide-2-aspirinate-5-salicylate (ISAS, 2).

It has been found that human plasma BuChE first selectively removes the acetyl group of the aspirinate of isosorbide-di-aspirinate (ISDA), which is attached at position-5, thus generating isosorbide-2-aspirinate-5-salicylate (ISAS). Human BuChE then efficiently detaches aspirin from isosorbide-2-aspirinate-5-salicylate (ISAS). ISDA undergoes hydrolysis along other parallel routes (FIG. 5A is a simplified version of this for clarity) and it is not as efficiently metabolised to aspirin as isosorbide-2-aspirinate-5-salicylate (ISAS), nor has it been found to be as potent in biological assays. ISAS has an aspirin release rate of 85% in plasma ($t_{1/2}$ 2 min) whereas ISDA is hydrolysed around 60% along the aspirin pathway with the remaining 40% proceeding along unproductive salicylate pathway. Indeed because ISDA has two aspirin molecules attached its overall yield in the strictest sense is 30%. Using specific enzyme inhibitors and purified enzyme solutions we were able to establish unequivocally the enzyme in human plasma responsible for the uniquely accurate activation of ISAS as butyrylcholinesterase (eg FIG. 5A).

Isosorbide-2-aspirinate-5-salicylate (ISAS) is not described in International Publication No. WO9817673. Although it is a potential metabolite no one could have anticipated that it would be a prodrug. Other actual or potential metabolites of ISDA (for example the 5-aspirinate, 2-aspirinate or 2-salicylate-5-aspirinate) were each synthesised and characterised. None of these acted as aspirin prodrugs in human plasma.

Advantageously, ISAS (2) is significantly more potent than aspirin as an inhibitor of human platelet aggregation induced by collagen (FIG. 6), ADP and arachidonic acid and it accordingly inhibits COX downstream products including thromboxane $A_2$ and malondialdehyde. It also dampens constitutive platelet glyco-protein expression at concentrations at which aspirin has no effect. The greater potency of isosorbide-2-aspirinate-5-salicylate (ISAS) than aspirin, though desirable from a drug development point of view, is puzzling and the subject of ongoing investigations. It has also been shown that isosorbide-2-aspirinate-5-salicylate (ISAS) needs to be activated by esterases to exert its pharmacological effects: it doesn't have intrinsic biological activity and is therefore a prodrug. While ISAS undergoes hydrolysis in human blood with a half-life of <2 minutes, it is stable in the presence of typical digestive proteases and towards esterases found in CACO-2 cells. It inhibits platelet aggregation towards arachidonic acid in human whole blood (impedance method) with an $IC_{50}$ of 17 µM. Aspirin's IC50 in this model is 25 µM. ISAS is also effective in preventing the $TXA_2$ synthesis in vivo ($TXB_2$/whole blood) and MDA synthesis by washed platelets.

Enzyme studies show that isosorbide-2-aspirinate-5-salicylate (ISAS) is specifically activated by two human enzymes: BuChE in human plasma, and less rapidly, but with the same pathway A/B ratio by human carboxylesterase-2 (CE-2) present in intestinal epithelial microsomes. The observation that two enzymes can release aspirin from isosorbide-2-aspirinate-5-salicylate (ISAS) is clinically relevant and advantageous: if a patient has aberrant enzyme function with respect to one, the other is likely to compensate and release aspirin. Another advantage to the design is that the compound is stable under conditions found in the lumen of the GI tract but breaks down rapidly after absorption to well-characterised metabolites: salicylic acid, isosorbide, and of course, aspirin. (The similarity of substrate preference in this regard by CE-2 and BuChE is very surprising). A further advantage to the compound is that its carrier is metabolised eventually to salicylic acid and isosorbide, compounds that are either innocuous or pharmaceutically well characterised. While ISAS has significant pharmaceutical merit in itself its discovery points to something more generally valuable. The discovery of ISAS and the kinetic models for its production and aspirin release in plasma are described in our recent paper (Moriarty et al. 2008).

Isosorbide-2-aspirinate-5-salicylate (ISAS) acts as an aspirin prodrug because the isosorbide-5-salicylate portion of the prodrug molecule has a high degree of complementarity to the active site of the human carboxylesterases. It is because of this that it undergoes very rapid hydrolysis. The isosorbide-5-salicylate portion or carrier group of ISAS successfully promotes its own detachment from aspirin while at the same time suppressing hydrolysis of the aspirin acetyl group. It introduces a new and highly effective carrier type for aspirin and potentially for other carboxylic acid drugs. This is an important insight for the invention.

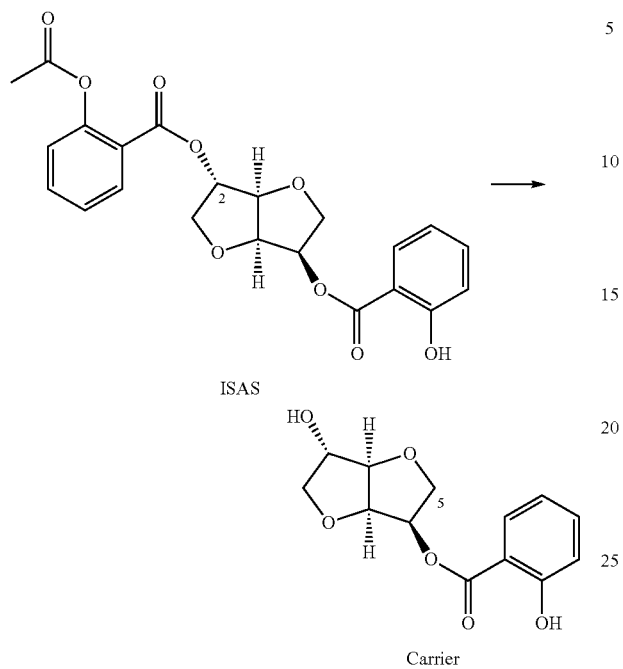

ISAS

Carrier

The question arose as to whether it might be possible to alter the isosorbide-5-salicylate structure for improved pharmaceutical characteristics while conserving its esterase complementarity. Moreover there was evidence that the pattern of substitution at the 5-position is critical for aspirin release because ISMNA (in which the 5-salicylate is replaced with a nitrate) is not an aspirin prodrug in human plasma. The conclusion is that a 5-nitrate is not compatible with productive human esterase binding. Approximately 25 compounds were prepared in which the 5-position was systematically changed in order to test the influence of the 5-group on the aspirin releasing characteristics of the carrier group (FIG. 7 and Table 2). The novel aspirin esters were tested by incubating them in human plasma solution and measuring the amount of aspirin produced relative to the molar amount of compound added to the plasma solution. The esters underwent characteristically rapid hydrolysis to different extents along the A and B routes some with release rates approaching the productivity of ISAS (Table 2 and FIG. 7).

The aspirin release characteristics of a range of 25 esters is shown in Table 2 along with some selected examples as structural formulae with percentage aspirin release in FIG. 7. It has been shown that the group at the 5-position markedly influences the direction of hydrolysis (FIG. 8 and examples in FIG. 9).

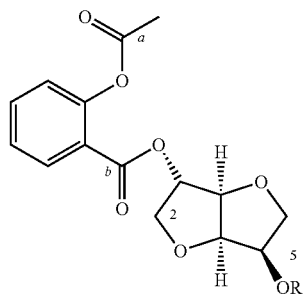

The unsubstituted compound (isosorbide-2-aspirinate, 17) is not an aspirin prodrug indicating that 5-substitution is required for aspirin release. In general it was found that significant aspirin release occurs with 5-benzoate and nicotinate esters. The dominant hydrolysis site in the case of compounds substituted with aliphatic esters was at the usual acetyl ester (cf Compounds 4, 5, 23 in Table 2). It was also found that aryl esters in which the phenyl group was substituted at the 2- and 3-positions were most productive. For example, compound 1 undergoes hydrolysis along the productive aspirin pathway to around 60%.

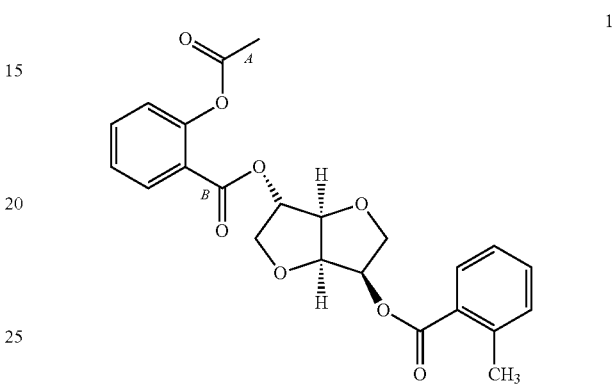

The most efficient compound found is ISAS which undergoes almost complete conversion to aspirin in the presence of purified butyrylcholinesterase and around 80% in human blood.

Isosorbide-2-aspirinate-5-salicylate (ISAS, 2) the metabolite of ISDA belongs to a new family of substituted 5-aromatic esters compounds that act as aspirin prodrugs in the presence of human esterases. It is not known why benzoate compounds further substituted at the ortho or meta position are so successful, but it is likely to be due to a favourable arrangement at the active site of the enzyme. This kind of remote control of the position of enzyme attack is unusual.

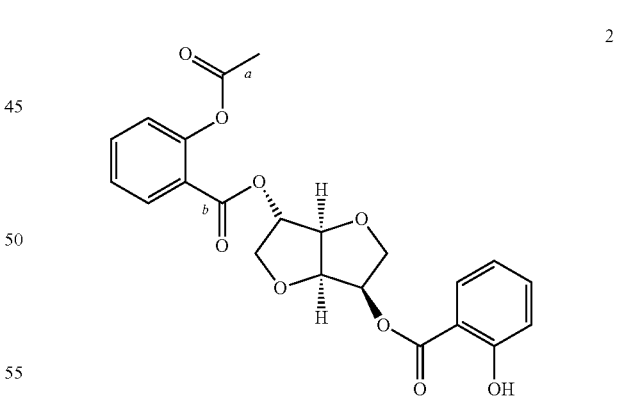

Thus, it has been found that certain isosorbide-based carrier groups promote hydrolysis at the correct point, leading to aspirin liberation in human blood (b above). Certain substituted isosorbide compounds release aspirin in significant quantities when incubated in human blood. The selective hydrolysis is caused by a highly specific interaction between the carrier group and human butyrylcholinesterase present in plasma and with CE-2 in the intestinal epithelium.

Recognition that isosorbide esters of aspirin can act as aspirin prodrugs provided that the 5-position is appropriately substituted is crucial to the invention. The most effective substituents are 5-aryl esters which are further substituted at the −2 or −3 position of the benzene ring. Such groups promote aspirin release at the remote isosorbide-2-position rather than acetyl group hydrolysis. Compound 2 is the most effective and the most studied of the prodrugs and it lead to the identification of a new efficient carrier class for aspirin prodrugs. However the invention includes and anticipates other compounds differently substituted at position 5 but equally efficiently converted to aspirin in the presence of blood plasma enzymes. In particular, there is strong commercial and academic interest in a prodrug device capable of releasing both aspirin and nitric oxide, NO..

Since the structural requirements for productive hydrolysis (or steering within the esterase site) were identified, the challenge of designing a prodrug of both aspirin and nitric oxide was continued. The SAR suggested that an isosorbide-5-benzoate carrier group might tolerate further substitution with a nitrate on the benzene ring without affecting its hydrolysis steering characteristics. Unfortunately aromatic nitrates are unstable—nitrate esters of phenol disproportionate readily to the ortho-nitro phenol. Instead a number of nitroxymethyl derivatives of isosorbide-2-aspirinate-5-benzoate were made which fit the pattern below: These include compounds 20-23 in Table 2.

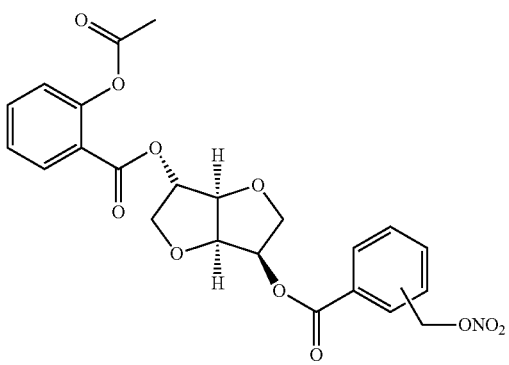

These were tested in the key human plasma hydrolysis model for ability to produce aspirin in human plasma. Consistent with the previous pattern, it was found that the ortho- and meta-substituted nitroxymethyl compound liberated aspirin in human plasma. There was no aspirin release from the para-substituted compound. The successful compounds also release significant amounts of aspirin in the presence of human intestinal microsomes, apparently mediated by the CE-2 enzyme, and following the same pattern as the lead ISAS (FIG. 9). An advantage of this is that where a patient has low BuChE activity, CE-2 could release aspirin along with the nitric oxide-donating moiety. Compound 20 has been tested on collagen-induced platelet aggregation in vitro and found to be more potent than aspirin in inhibition of aggregation. It is also a more potent inhibitor of ADP-induced platelet aggregation in PRP. However, because it also liberates NO. it is expected to inhibit aggregation to pathological stimuli that aspirin has no effect on. Aspirin inhibits only thromboxane-dependent aggregation i.e. platelet aggregation to only one stimulus. It has little effect on high dose collagen aggregation or on aggregation to ADP. Nitric oxide has been shown to attenuate the gastric toxicity of aspirin and to promote ulcer healing. Compounds capable of liberating both aspirin and nitric oxide have significant potential in cancer prevention, therapy and in cardiovascular disease treatment. The activation of glycoprotein integrin receptor GPIIb/IIIa is crucial for platelet aggregation to occur. In addition the translocations of P-selectin from α-granules to the platelet surface membrane underlie platelet adhesion, respectively. We have measured these receptors upon aggregation with different concentration of the compounds. FIG. 32-36 show that pro-asa and nitro-asa significantly decreased the activation of GPIIb/IIIa and translocation of P-selectin. The activation of GPIIb/IIIa is controlled dynamic interplay of pathway that stimulate or inhibit aggregation. Nitric oxide mediate major inhibitor pathway and regulate GPIIb/IIIa function. Aspirin failed to inhibit platelets activation in the same concentration like ISAS (2) or and nitrate compounds 31-32.

The invention also provides for pharmaceutical compositions comprising a compound of the invention which may be adapted for oral administration as a capsule or tablet or for percutaneous administration, for example in the form of a transdermal patch. The composition may also be in the form of a suppository or an aqueous-based formulation.

The invention also provides the use of the compound to achieve anti-platelet activity and/or other aspirin type activities such as anti-pyretic and/or anti-inflammatory activity.

In a particularly preferred embodiment of the invention the composition includes another pharmaceutical entity, especially a therapeutic oil, typically a fish oil such as cod liver oil, or a vegetable oil such as evening primrose oil. In this case the composition may be in the form of a capsule having a retaining shell containing a filling including the active ingredients. The filling may include a suspending agent such as one selected from one or more of colloidal silicon dioxide, hydrogenated vegetable oils (optionally in combination with beeswax), high melting point partial glycerides, and/or lecithins. The filling may also include an antioxidant such as one selected from one or more of D-alpha tocopherol, D-alpha tocopherol acetate, mixed tocopherols and ascorbic acid. The shell may be a gelatin shell.

BRIEF DESCRIPTION OF THE DRAWINGS

FIGS. 7A and 7B illustrate the aspirin release dependence at position 2 on the structure of the ester at the remote position 5.

DETAILED DESCRIPTION OF THE INVENTION

General Experimental Approaches: Materials

5-ISMN was obtained from Sifa Ltd. Purified human serum butyrylcholinesterase (EC 3.1.1.8), rabbit liver carboxylesterase (EC 3.1.1.1), BNPP (bis-4-nitrophenylphosphate), iso-OMPA (tetraisopropylpyrophosphoramide), pooled human liver microsomes, 3-chloromethylbenzoyl chloride, 4-chloromethylbenzoyl chloride, silver nitrate, phthalide, dichlorotriphenylphosphorane and HPLC grade solvents were obtained from Sigma-Aldrich. Collagen and ADP was obtained from Chronolog (Havertown, Pa., U.S.A.). Allophycocyanin (APC)-conjugated monoclonal antibody against high-affinity GPIIb/IIIa (PAC-1-APC) and APC-conjugated monoclonal antibody against human platelet P selectin (CD62P) were purchased from BD Biosciences (Oxford, UK).

All other solvents and reagents were analytical grade. Pooled human intestinal microsomes were obtained from BD Gentest in the UK.

The compounds of the invention are easily prepared from isosorbide-mono-nitrate aspirinate (ISMNA), itself prepared by esterification of isosorbide-mono-nitrate (ISMN) with and acetyl salicoyl chloride according to Gilmer et al 2001. The nitrate is selectively removed by treatment with palladium on carbon under an atmosphere of hydrogen generating the key intermediate isosorbide-2-aspirinate. The compounds may also be obtained by selective 5-esterification of isosorbide followed by attachment of the aspirinate group at position-2 (The 5-position in isosorbide despite being endo is more reactive towards acylation than the 2-exo position because the 5-OH is activated by an intramolecular H-bond)

Figure 10:
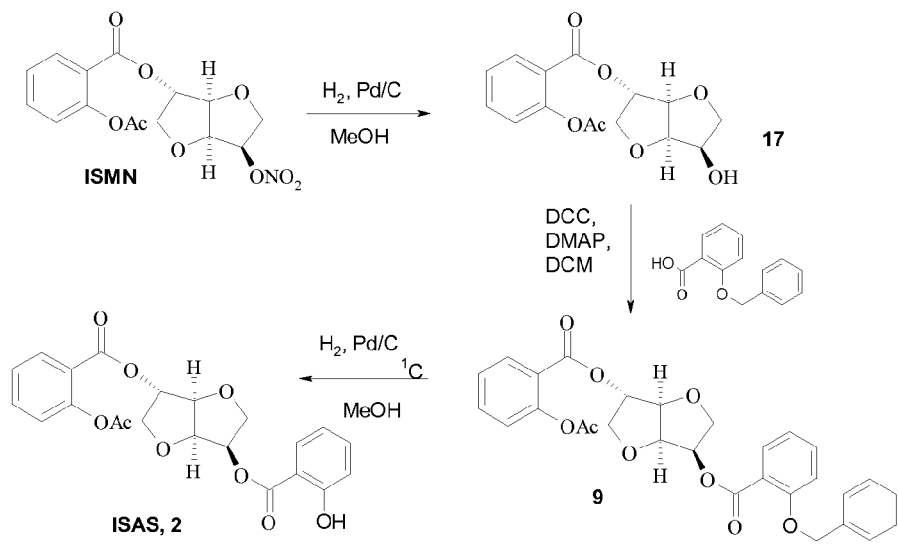
FIG. 10: Synthesis of ISAS 2 from ISMN by coupling to protected salicylic acid followed by de-benzylation.
Figure 11:
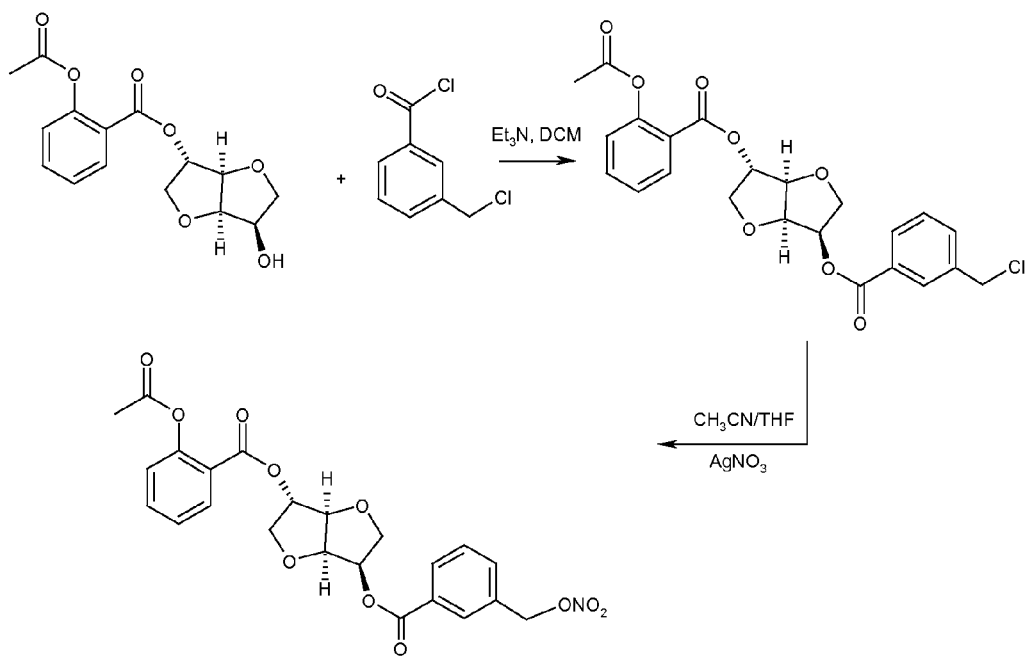
FIG. 11: Synthetic route for the preparation of Is-2-aspirinate-5-(3-nitrooxy-methyl)benzoate 21

In the case of isosorbide-2-aspirinate-5-salicylate (ISAS) direct acylation with salicylic acid would be complicated by competition between the salicylate-OH and the isosorbide-OH. Consequently a benzyl-ether protected salicylic acid is introduced first using standard DCC coupling procedure and the benzyl protection removed under reductive conditions (FIG. 10).

Other ester compounds of the invention can be prepared by directed acylation using DCC coupling or by treatment with the appropriate acid chloride in the presence of a tertiary base such as triethylamine. Nitroxy-substituted esters may be prepared by linking directly to the appropriately substituted acids. Alternatively, nitroxy-substituted compounds may be obtained by first esterifying with an acid bearing a chloride or bromide which can be subsequently displaced by nitrate by treatment with $AgNO_3$ in acetonitrile.

EXPERIMENTAL EXAMPLES

Figure 1:
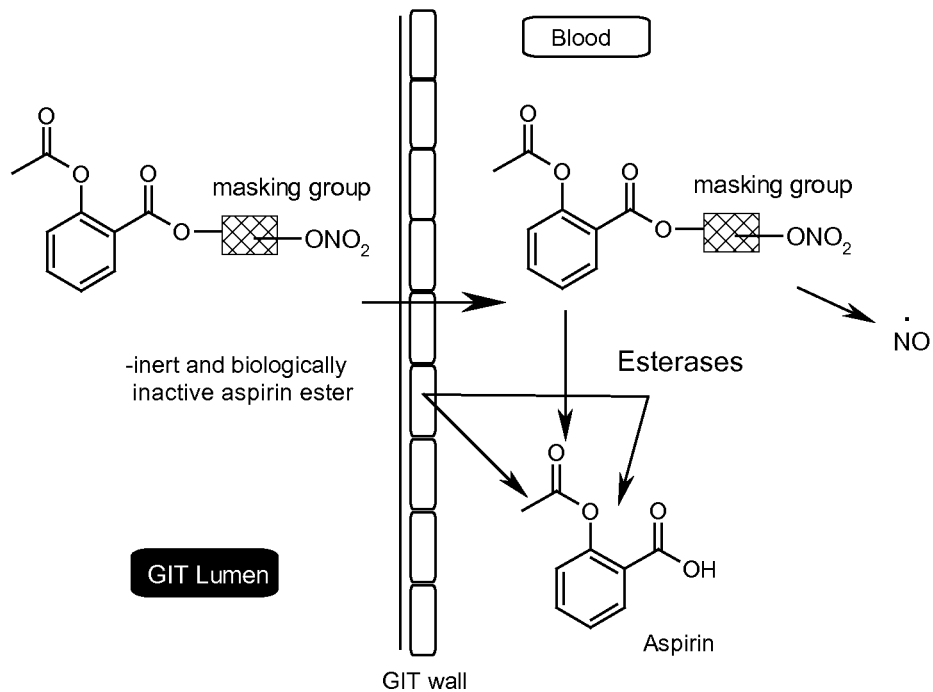
FIG. 1: Aspirin Toxicity Obviation Theory
Figure 2:
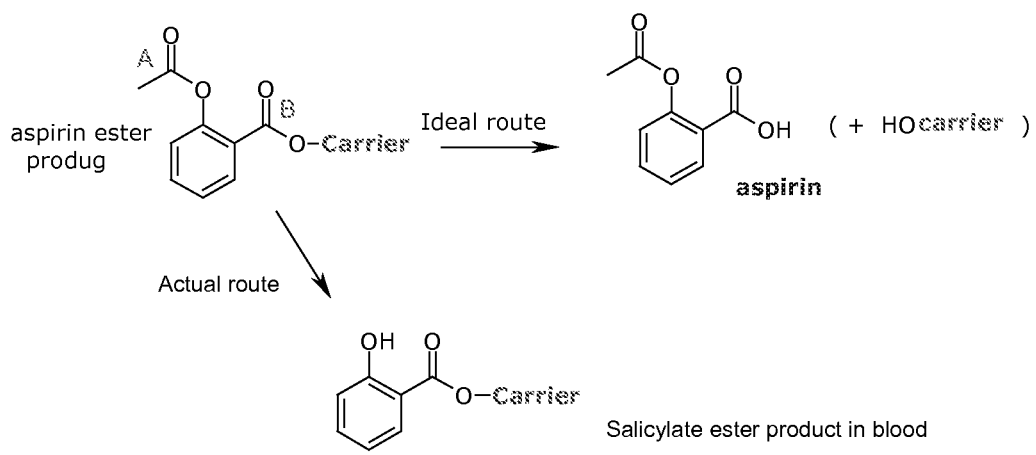
FIG. 2: A successful aspirin prodrug must undergo hydrolysis at the ester B at a greater rate than at the O-acetyl group A.
Figure 3A:
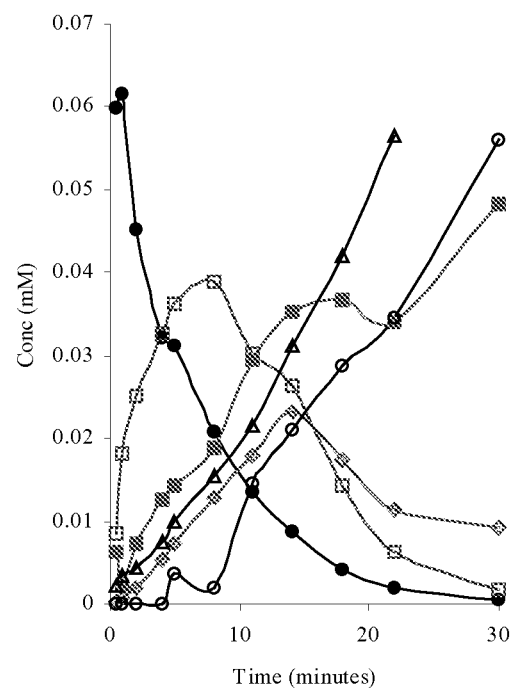
FIGS. 3A and 3B: Progress curve for the hydrolysis of ISDA in 10% human plasma (pH 7.4, 37° C.): showing the concentration of the parent and some of its metabolites as measured by HPLC at successive time point: ISDA (●), aspirin ( ), salicylic acid (o), isosorbide-2/5-aspirinate-2/5-salicylate (□), isosorbide disalicylate (◊) and isosorbide-5-salicylate (Δ). Maximum aspirin is delayed with respect to the disappearance of the parent ISDA indicating that a metabolite is responsible for its production. The plot is redrawn with the ISDA curve omitted.
Figure 3B:
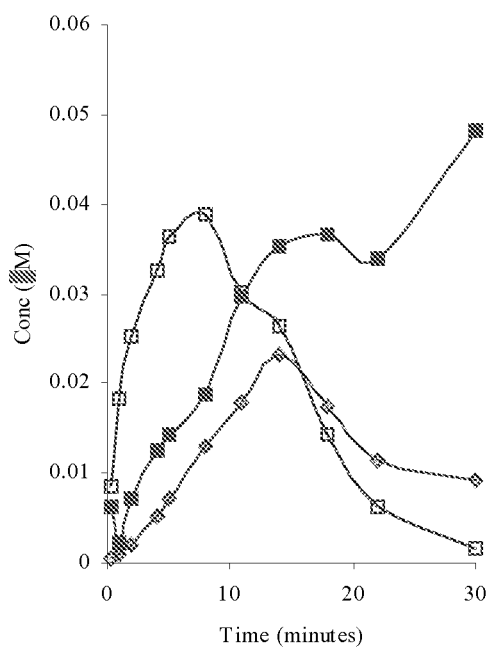
Figure 4A:
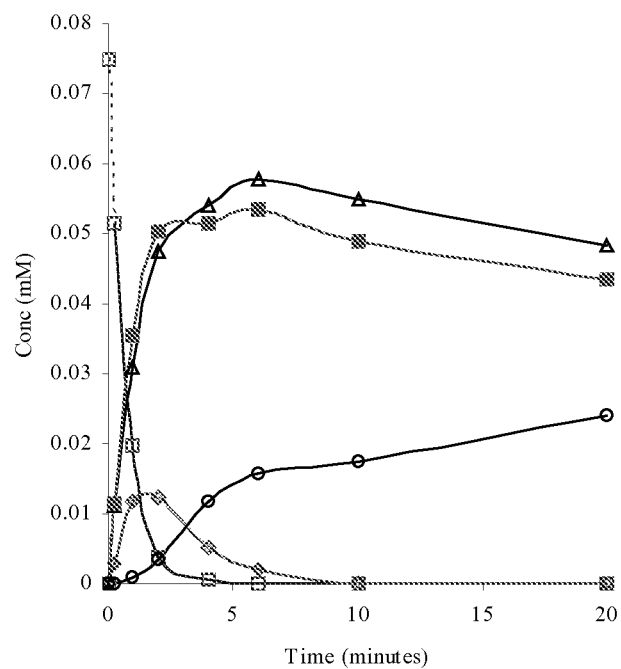
FIG. 4A: progress curve for the hydrolysis of isosorbide-2-aspirinate-5-salicylate ISAS (2) in 50% human plasma (pH 7.4) at 37° C.: ISAS (□), isosorbide disalicylate (◊), isosorbide-5-salicylate (Δ), aspirin ( ) and salicylic acid (o).
Figure 4B:
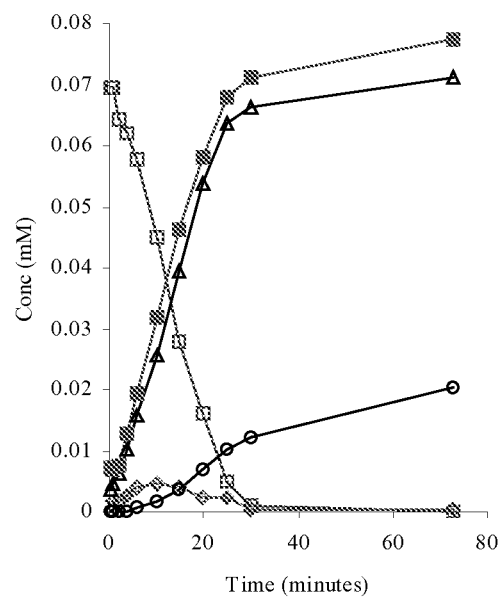
FIG. 4B: Progression curve for the hydrolysis of isosorbide-2-aspirinate-5-salicylate ISAS with purified human serum BuChE at pH 7.4 and 37° C.: Isosorbide-2-aspirinate-5-salicylate (□), isosorbide-5-salicylate (Δ), aspirin ( ), salicylic acid (o) and isosorbide disalicylate (◊).
Figure 5A:
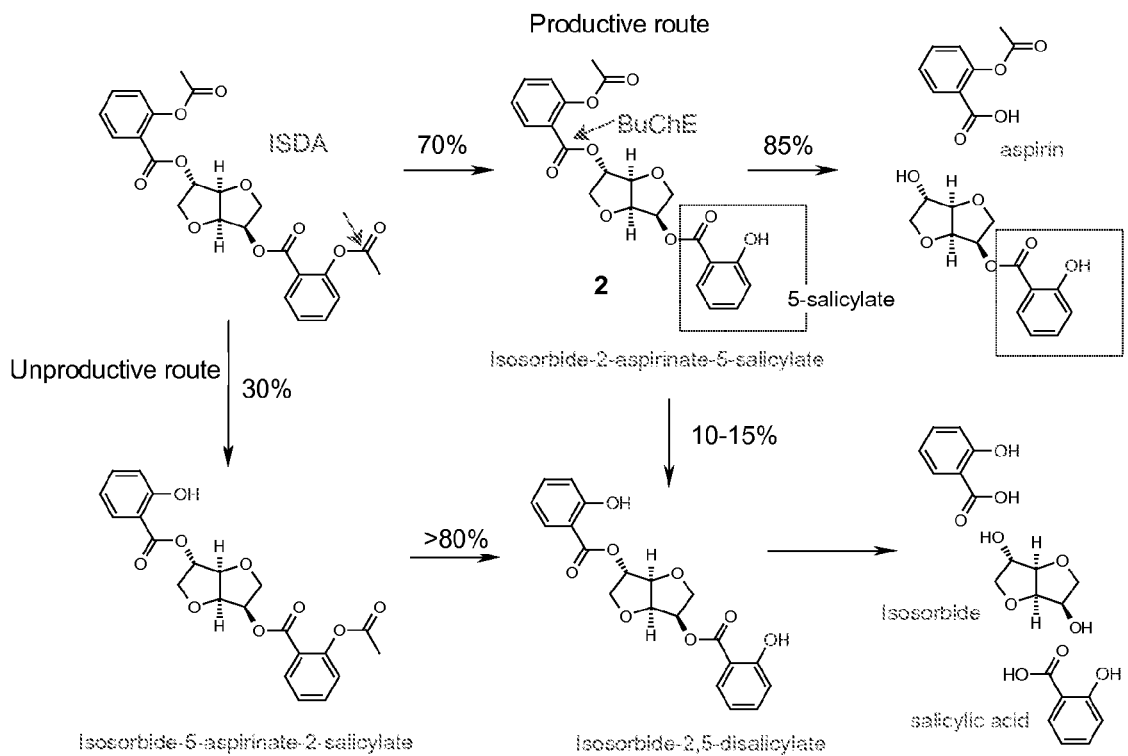
FIG. 5A. ISDA first undergoes hydrolysis at the acetyl group of the 5-aspirinate (70%) releasing ISAS (2) which undergoes hydrolysis predominantly to aspirin and isosorbide-5-salicylate. Major points of productive intervention by plasma cholinesterase (BuChE) are indicated in red. Note that this is relatively stable towards esterases. Hydrolysis of ISDA also proceeds (30%) along a parallel unproductive pathway that does not release aspirin but isosorbide and salicylic acid instead.
Figure 6A:
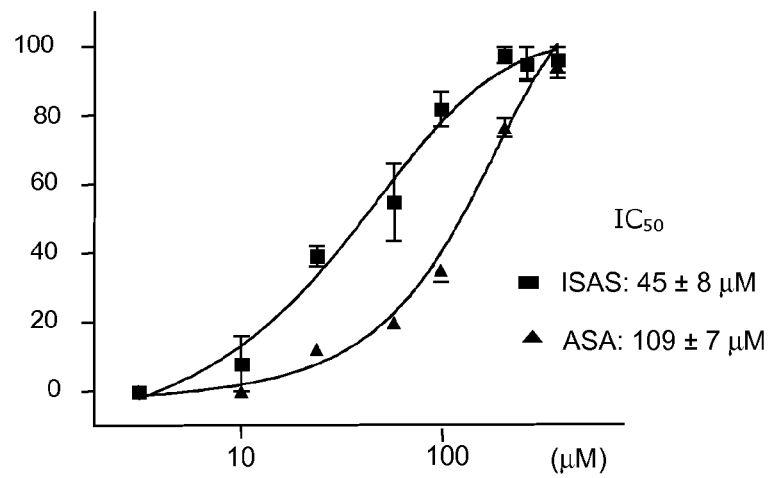
FIG. 6: Concentration-response curves showing inhibition of collagen-induced human platelet aggregation in vitro by ISAS (2) and aspirin (ASA) are shown in FIG. 6A. Concentrations of drugs inhibiting aggregation by 50% ($IC_{50}$) are also shown. ISAS is significantly more potent than ASA on aggregation (data are mean±S, D p<0.01, n=4). 6B shows relative inhibition curves for ISAS (2), nitric oxide releasing prodrugs 31, 32, 33 and aspirin. 6C shows the % aggregation of PRP following incubation with ISAS, compounds 31-33 or aspirin. This figure shows percent aggregation to collagen rather than percent inhibition of aggregation to collagen at three different concentrations for five compounds, aspirin, ISAS and the three isomeric nitrates, 31, 32, 33. (***P<0.05).
Figure 6B:
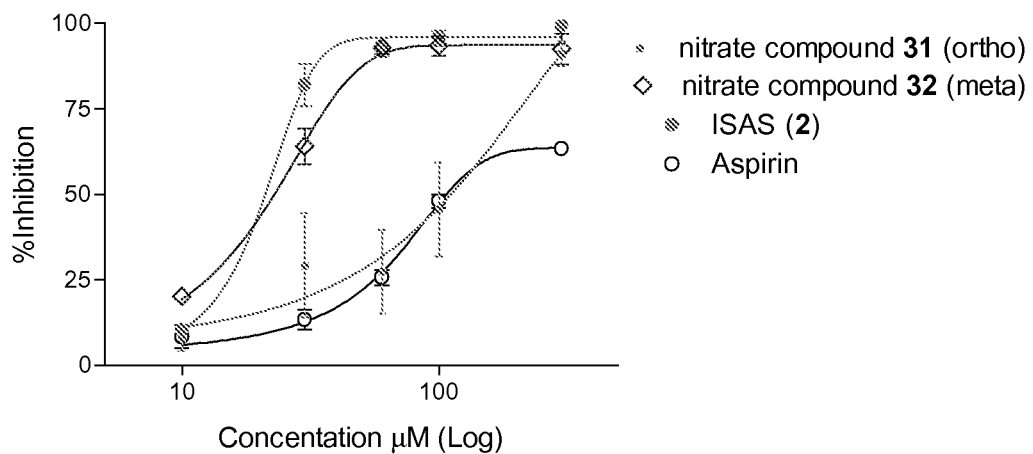
Figure 6C:
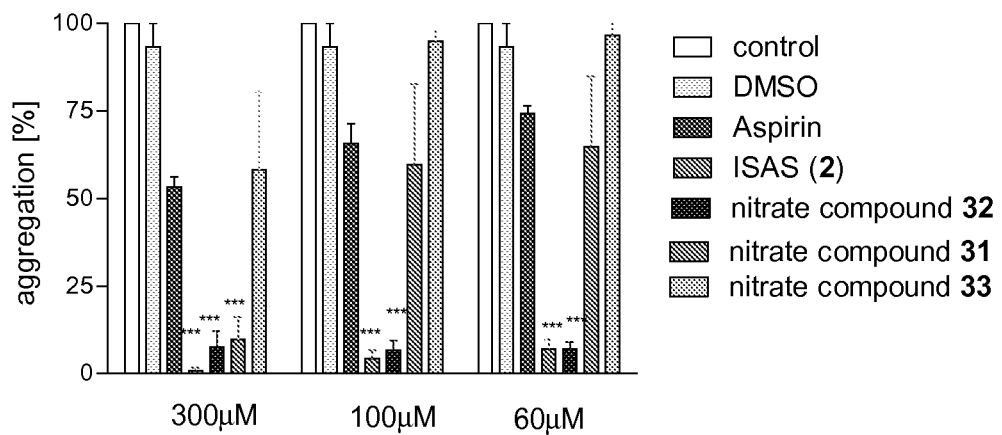
Figure 7A:
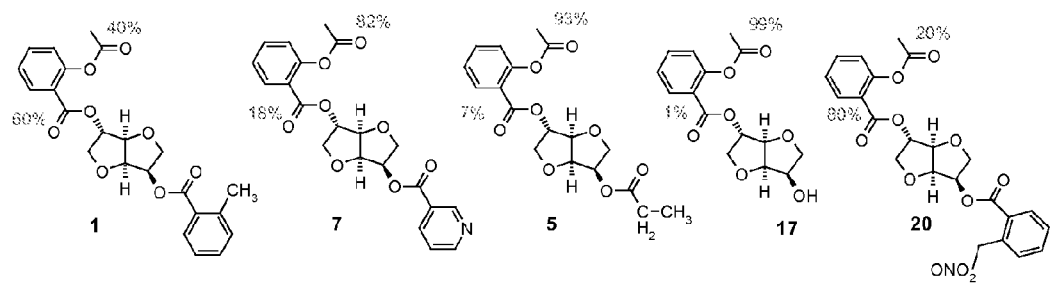
FIGS. 7A and 7B: Examples of alternative 5-esters incubated in human plasma solution from Table 2 (FIG. 7A). The % values in FIG. 7A represent the amount of hydrolysis occurring at sites A (liberating salicylate ester) and B (liberating aspirin) in FIG. 7B.
Figure 7B:
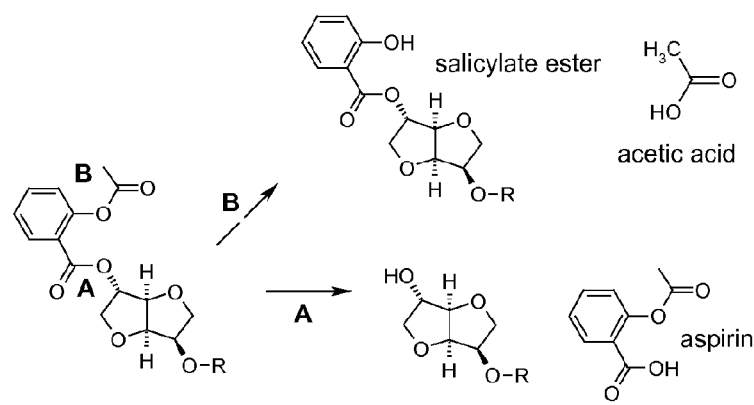
Figure 8:
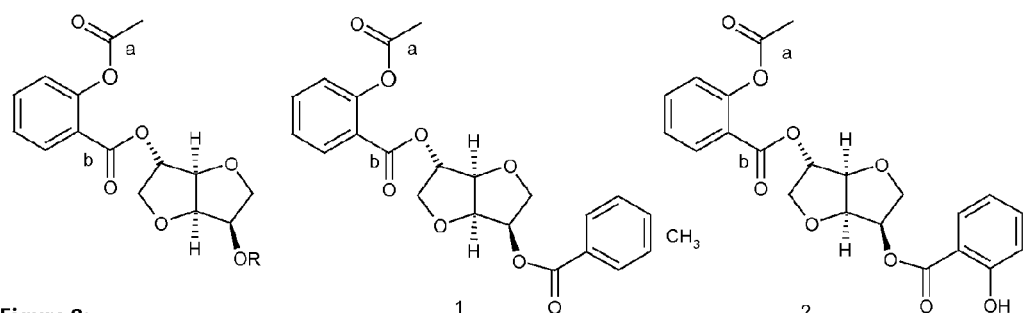
FIG. 8: The 5 substituent 'R' decisively influences the hydrolysis pathway.
Figure 9:
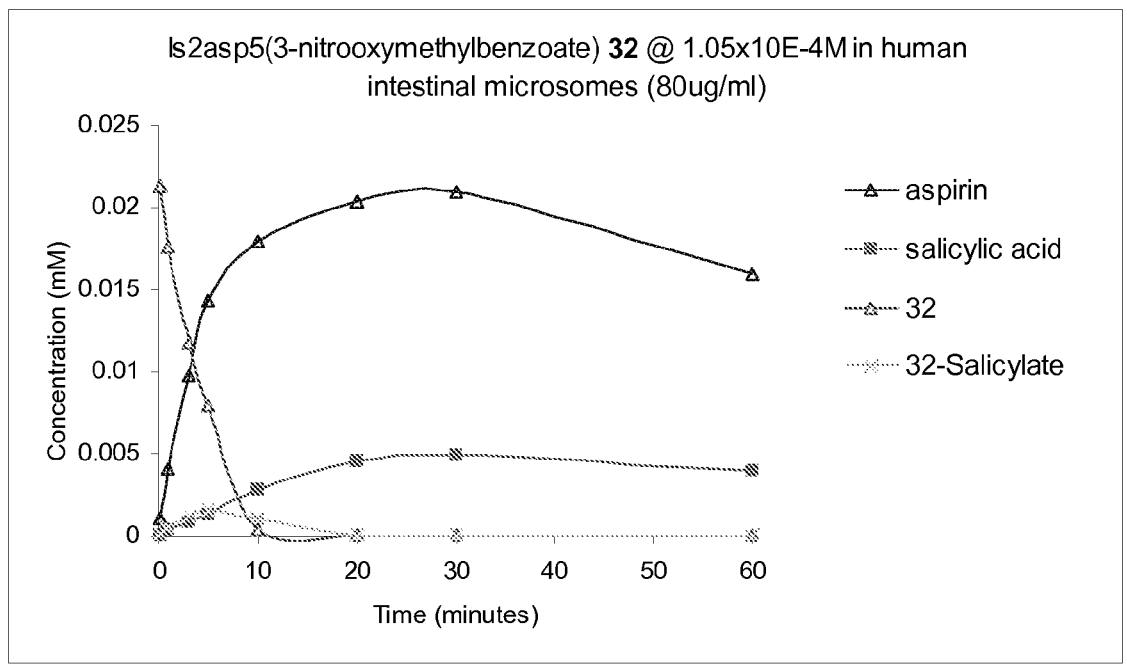
FIG. 9: Showing the disappearance of isosorbide-2-aspirinate-5-(3-nitroxymethyl)-benzoate following incubation in the presence of microsomes from the human intestinal epithelium and the liberation of aspirin, salicylic acid and the nitrate-substituted isosorbide carrier.

Synthesis of Isosorbide-2-aspirinate-5-esters: Molecular Formulae Appear in FIG. 2

Isosorbide-2-aspirinate-5-[2-methylbenzoate] 1

To a solution of isosorbide-2-aspirinate 17 (0.2 g, 0.65 mmol) in dichloromethane (15 ml) was added triethylamine (0.11 ml, 0.98 mmol) and 2-toluoyl chloride (0.09 ml, 0.72 mmol). The reaction mixture was stirred at room temperature for 24 hours and then was washed with water (2×25 ml), HCl (1 m, 25 ml) and saturated aqueous $NaHCO_3$ before drying over anhydrous $MgSO_4$. Solvent was removed in vacuo to give 0.41 g of crude product as brown oil. Purification by column chromatography using hexane and ethyl acetate (2:1) as eluant gave product as yellow oil. This was recrystallised in ethanol to yield compound 1 as a white solid (0.11 g, 39.6%) m pt. 104-106° C. $IR_{vmax}$ (KBr): 2987.1 and 2922.8 (C—H stretching), 1762.0 and 1718.1 (C=O), 1259.5 and 1199.8 (C(O)OR aromatic), 1072.4 (C—O—C) $cm^{-1}$. HRMS: Requires: 449.1212 ($M^+$+23), Found: 449.1238 ($M^+$+23), $^1H$ NMR δ ($CDCl_3$): 2.38 (3H, s, $OCOCH3$), 2.65 (3H, s, $ArCH_3$), 4.01 (1H, dd, J 5.52 and 5.52 Hz, IS6-H [α]), 4.12 (3H, m, IS1H [αβ] and IS6H [β]), 4.66 (1H, d, J 4.52 Hz, ISH-3), 5.04 (1H, t, J 5.04 and 5.0 Hz, ISH-4), 5.41 (1H, q, J 5.52, 5.52 and 5.52 Hz, ISH-5), 5.47 (1H, d, J 2.0 Hz, ISH-2), 7.13 (1H, dd, J 1.0 and 1.0 Hz, ArH-4), 7.33 (1H, t, J 7.0 and 6.52 Hz, ArH-2), 7.59 (1H, t, J 6.52 and 6.52 Hz, ArH-3), 8.02 (1H, dd, J 1.52 and 2.0 Hz, ArH-1). $^{13}C$ NMR ppm ($CDCl_3$): 20.43 (Ar—$CH_3$), 21.12 ($OCOCH_3$), 70.29 (ISC-1), 72.72 (ISC-6), 73.81 (OC(O)Ar), 78.22 (ISC-4), 80.52 (ISC-2), 85.63 (ISC-3), 122.32 ($Ar_1$C-1), 123.38 ($Ar_1$C-4), 125.58 ($Ar_1$C-2 and $Ar_2$C-4), 128.46 ($Ar_2$C-2 and $Ar_2$C-5), 130.19 ($Ar_2$C-3), 133.78 ($Ar_1$C-3), 140.08 ($Ar_2$C-1), 150.26 ($Ar_1$C-5), 163.12 (ArOCOMe), 169.15 (ArCOOR)

Isosorbide-2-aspirinate-5-salicylate, ISAS, 2

2-benzyloxybenzoic acid (364.8 mg=1.6 mmol) was dissolved in dry DCM (20 mls) and stirred. Is-2-asp-5-OH (500 mg=1.6 mmol) and 10% DMAP was added. The flask was cooled to 0° C. and DCC (340 mg, 1.6 mmol) was added. Stirring was continued for five minutes and the temperature was allowed to come to room temperature where it was stirred over night. The reaction was filtered and the filtrate was washed with 0.1M HCl, 5% $NaHCO_3$ and water. Dried over sodium sulfate and evaporated to an oil. This was purified by column chromatography hexane/ethyl acetate (2:1) to give a white product (Rf=0.4, 228 mg). This was dissolved in methanol/ethyl acetate (1:1). Pd/C was added and the reaction was stirred under hydrogen over night. Reaction was filtered and concentrated. Oil was purified by column chromatography using hexane/ethyl acetate (1:1) to yield a white solid (107 mg Rf=0.67)). $^1H$ NMR δ ($CDCl_3$) 400 MHz: 2.38 (3H, s, $OCOCH_3$), 4.02 (4H, m, ISH-1, ISH-1', ISH-6 and ISH-6'), 4.63 (1H, d, ISH-3), 5.03 (1H, t, ISH-4), 5.43 (2H, dd, ISH-2, ISH-5), 6.91 (1H, t, Ar—H), 7.01 (1H, d, Ar—H), 7.1 (1H, d, Ar—H), 7.28 (1H, t, Ar—H), 7.48 (1H, t, Ar—H), 7.53 (1H, t, Ar—H), 7.89 (1H, d, ArH), 8.00 (1H, d, ArH), 10.61 (1H, s, OH). $^{13}C$ NMR ppm ($CDCl_3$) 400 MHz: 20.51 ($OCOCH_3$), 70.46 (ISC-1), 72.78 (ISC-6), 74.31 (ISC-5), 77.91 (ISC-2), 80.69 (ISC-4), 85.70 (ISC-3), 117.30 ($Ar_2$C-1), 118.90, 123.41, 125.65, 129.47, 131.42, 133.94, 135.65, 150.24 ($Ar_1$C-2), 163.12 (ArOCOCH_3), 168.87 (ArC(O)OR).

Isosorbide-2-aspirinate-5-[3-methylbenzoate] 3

Isosorbide-2-aspirinate 17 (0.2 g, 0.65 mmol) was dissolved in toluene (15 ml) at 0° C., to which was added DCC (0.13 g, 0.65 mmol) and DMAP (0.08 g, 0.07 mmol). After 10 mins the reaction vessel was returned to room temperature and 3-toluic acid (0.09 g) was added and allowed to stir for 24 hours. After washing with HCl (30 ml, 1M), saturated aqueous $NaHCO_3$ (30 ml), saturated brine solution (30 ml) and water (3×30 ml) the reaction mixture was dried over anhydrous $Na_2SO_4$ and solvent removed in vacuo to yield crude product as a clear oil. Purification by column chromatography using hexane and ethyl acetate (3:2) as eluant yielded compound 3 as white crystals (0.12 g, 43.2%): m.pt. 96-98° C. $IR_{vmax}$ (KBr): 2987.1 and 2922.8 (C—H stretching), 1762.0 and 1718.1 (C=O), 1259.5 and 1199.8 (C(O)OR, aromatic), 1072.4 (C—O—C) $cm^{-1}$. HRMS: Requires: 449.1212 ($M^+$+ 23), Found: 449.1234 ($M^+$+23), $^1H$ NMR δ ($CDCl_3$): 2.36 (3H, s, $OCOCH_3$), 2.43 3H, s, $ArCH_3$), 4.09 (4H, m, IS1-$H_2$ [α+β] and IS6-$H_2$[α+β]), 4.65 (1H, d, J 5.0 Hz, ISH-3), 5.04 (1H, t, J 5.04 and 5.0 Hz, ISH-4), 5.43 (2H, m, ISH-5 and ISH-2), 7.12 (1H, d, J 8.0 Hz, ArH-4), 7.35 (3H, m, ArH-2), 7.58 (1H, q, J 1.0, 6.56 and 1.48 Hz, ArH-3), 8.01 (1H, dd, J 1.0 and 1.52 Hz, ArH-1). $^{13}C$ NMR ppm ($CDCl_3$): 20.42 (Ar $CH_3$), 20.79 ($OCOCH_3$), 70.39 (ISC-1), 72.77 (ISC-6), 73.92 (ISC-5), 78.19 (ISC-4), 80.66 (ISC-2), 85.66 (ISC-3), 122.35 ($Ar_1$C-1), 123.39 ($Ar_1$C-4), 125.57 ($Ar_1$C-6), 126.45 ($Ar_1$C-2), 12.89 ($Ar_2$C-4), 129.80 ($Ar_2$C-5), 131.37 ($Ar_2$C-3), 133.77 ($Ar_2$C-1), 150.25 ($Ar_1$C-5), 163.15 (ArOCOCH_3), 165.58 (ISOCOAr), 169.12 (ArOCO).

Isosorbide-2-aspirinate-5-acetate 4

To a solution of isosorbide-2-aspirinate 17 (0.2 g, 0.65 mmol) in dichloromethane (20 ml) was added triethylamine (0.09 ml, 0.65 mmol) and acetic anhydride (0.06 ml, 0.65 mmol). The reaction vessel was stirred at room temperature for 24 hours before washing with water (2×20 ml), HCl (1M, 30 ml), saturated aqueous $NaHCO_3$ (30 ml) and drying over $MgSO_4$. Solvent was removed by rotary evaporation to yield 0.52 g of crude product. Purification by column chromatography using hexane and ethyl acetate (3:2) as eluant afforded compound 4 as white crystalline material (0.1 g, 43.8%). m.pt. 96-98° C. IR$_{vmax}$ (KBr): 2966.9 and 2928.6 (C—H stretching), 1751.6 and 1734.0 (C=O), 1607.8 (C=C stretching), 1262.0 and 1193.9 (C(O)OR aromatic), 1082.5 (C—O—C) cm$^{-1}$. HRMS: Requires: 373.0899 (M$^+$+23), Found: 373.0877 (M$^+$+23), $^1$H NMR δ (CDCl$_3$): 2.13 (3H, s, IS—OCOCH$_3$), 2.37 (3H, s, Ar—OCOCH$_3$), 3.85 (1H, q, J 5.52, 4.52 and 4.96 Hz, IS6α-H), 3.99 (1H, q, J 6.0, 3.52 and 6.04 Hz, IS6β-H), 4.10 (2H, t, J 3.52 and 2.0 Hz, IS1H$_2$[α+β]), 4.59 (1H, d, J 4.52 Hz, ISH-3), 4.90 (1H, t, J 5.0 and 5.04 Hz, ISH-4), 5.19 (1H, d, J 5.52 Hz, ISH-5), 5.44 (1H, d, J 5.52 Hz, ISH-2), 7.12 (1H, d, J 8.04 Hz, ArH-4), 7.33 (1H, t, J 7.52 and 7.56 Hz, ArH-2), 7.59 (1H, m, ArH-3), 8.01 (1H, dd, J 6.04 Hz, ArH-1). $^{13}$C NMR ppm (CDCl$_3$): 20.43 (ArO-COCH$_3$), 20.18 (IS—OCOCH$_3$), 69.91 (ISC-2), 72.78 (ISC-6), 73.52 (ISC-5), 78345 (ISC-3), 80.32 (ISC-1), 122.29 (ArC-5), 123.39 (ArC-1), 125.58 (ArC-3), 131.36 (ArC-2), 133.81 (ArC-4), 154.32 (ArC-6), 167.15 (OCOAr), 168.48 (ArOCOCH$_3$), 171.27 (OCOCH$_3$).

Isosorbide-2-aspirinate-5-proprionate 5

Isosorbide-2-aspirinate 17 (0.3 g, 0.98 mmol) was dissolved in dichloromethane (20 ml) to which was added proprionic anhydride (0.14 ml, 1.07 mmol) and triethylamine (0.09 ml, 1.07 mmol). This was allowed to stir at room temperature for 24 hours before washing with HCl (30 ml, 1M), saturated aqueous NaHCO$_3$ (30 ml) and water (2×30 ml). Reaction was dried over anhydrous Na$_2$SO$_4$ and solvent was removed in vacuo to yield crude product as a yellow oil (0.19 g). Purification by column chromatography using hexane and ethyl acetate (5:2) as eluant yielded product as white crystals (0.3 g, 84.3%): m.pt. 54-56° C. IR$_{vmax}$ (KBr): 2989.0 and 2933.0 (C—H stretching), 1764.0 and 1734.5 (C=O), 1606.3 (C=C stretching), 1254.3 and 1193.6 (C(O)OR, aromatic), 1080.6 (C—O—C) cm$^{-1}$. HRMS: Requires: 387.1056 (M$^+$+23), Found: 387.1069 (M$^+$+23). $^1$H NMR δ (CDCl$_3$): 1.19 (3H, t, J 8.04 and 7.52 Hz, CH$_3$), 2.37 (3H, s, OCOCH$_3$), 2.44 (2H, q, J 7.52, 8.04 and 7.52 Hz, OCH$_2$), 3.86 (1H, q, J 5.52, 4.52 and 5.04 Hz, IS6α-H), 3.98 (1H, q, J 5.52, 4.04 and 6.0 Hz, IS6β-H), 4.08 (2H, m, IS1H$_2$[α+β]), 4.59 (1H, d, J 4.52 Hz, ISH-3), 4.91 (1H, t, J 5.0 and 5.04, ISH-4), 5.20 (1H, q, J 5.04, 6.0 and 5.52 Hz, ISH-5), 5.43 (1H, d, J 3.0 Hz, ISH-2), 7.12 (1H, dd, J 1.0 and 1.0 Hz, ArH-4), 7.33 (1H, t, J 1.0, 6.56 and 8.0 Hz, ArH-2), 7.59 (1H, t, J 6.0 and 6.52 Hz, ArH-3), 8.01 (1H, dd, J 1.48 and 2.0 Hz, ArH-1). $^{13}$C NMR ppm (CDCl$_3$): 8.62 (CH$_2$CH$_3$), 20.49 (COCH$_3$), 26.84 (OCOCH$_2$), 70.08 (ISC-2) 72.72 (ISC-6), 73.32 (ISC-5), 78.12 (ISC-3), 80.37 (ISC-1), 85.45 (ISC-4), 122.22 (ArC-5), 123.41 (ArC-1), 125.64 (ArC-3), 131.41 (ArC-2), 133.89 (ArC-4), 150.24 (ArC-6), 163.09 (OCOAr), 169.28 (OCOCH$_3$), 173.40 (OCOCH$_2$).

Isosorbide-2-aspirinate-5-benzoate 6

To a solution of isosorbide-2-aspirinate 17 (1.0 g, 3.25 mmol) in dichloromethane (20 ml) was added benzoic acid (0.59 g, 4.88 mmol), DCC (1.34 g, 6.49 mmol) and DMAP (0.38 g, 3.11 mmol). The reaction mixture was allowed to stir at room temperature for three hours before filtering off precipitate and washing the filtrate with HCl (30 ml, 1M), saturated aqueous Na$_2$HCO$_3$ (30 ml) and water (3×30 ml). It was dried over anhydrous Na$_2$SO$_4$ and solvent was removed in vacuo to give colourless oil, which was recrystallised in ethanol to afford product as white crystals (1.13 g, 84.3%): m.pt. 80-82° C. IR$_{vmax}$ (KBr): 2991.1 and 2932.9 (C—H, stretching), 1762.9 and 1720.6 (C=O), 1275.5 and 1199.1 (C(O) OR aromatic), 1078.4 (C—O—C) cm$^{-1}$. HRMS: Requires: 435.1056 (M$^+$+23), Found: 435.1043 (M$^+$+23). $^1$H NMR δ (CDCl$_3$): 2.37 (3H, s, OCOCH$_3$), 4.07 (1H, m, IS1α-H), 4.11 (3H, m, IS6H[α+] and IS1β-H), 4.65 (1H, d, J 5.0 Hz, ISH-5), 5.05 (1H, t, J 5.5 and 5.0 Hz, ISH-3), 5.56 (1H, m, ISH-4), 7.13 (1H, d, J 8.04 Hz, Ar$_1$h1-5 and Ar$_1$H-3), 7.27 (1H, t, J 8.04 and 6.52 Hz, Ar$_2$H— and Ar$_2$H-5), 7.33 (1H, d, J 7.56 Hz, Ar$_1$H-4), 7.49 (2H, t, J 7.52 and 7.56 Hz, Ar$_2$H-5), 8.01 (1H, d, J 7.56 Hz, Ar$_1$H1-2), 8.12 (2H, d, J 7.52 Hz, Ar$_2$H-2 and Ar$_2$H-6). $^{13}$C NMR ppm (CDCl$_3$): 20.44 (OCOCH$_3$), 70.42 (ISC-1), 72.79 (ISC-6), 73.97 (ISC-5) 78.16 ISC-2), 80.67 (ISC-4), 85.67 (ISC-3), 123.39 (Ar$_1$C-5), 125.58 (AR$_1$C-1), 128.00 (Ar$_1$C-3), 129.31 (Ar$_2$C-3 and Ar$_2$C-5), 131.39 (Ar$_1$C-2 and Ar$_2$C-6), 132.82 (Ar$_2$C-2 and Ar$_2$C-1), 133.79 (Ar$_2$C-4), 134.81 (Ar$_1$C-4), 154.32 (Ar$_1$C-6), 167.10 (OCOCH$_3$), 168.2 (OCOAr$_1$ and OCOAr$_2$).

Isosorbide-2-aspirinate-5-nicotinate 7

Isosorbide-2-aspirinate 17 (0.3 g, 0.98 mmol), in dichloromethane (20 ml) at 0° C. was stirred for 10 mins in the presence of DCC (0.2 g, 0.98 mmol) and DMAP (0.12 g, 0.98 mmol). The reaction vessel was returned to room temperature, nicotinic acid (0.12 g, 0.98 mmol) was added and allowed to stir for 24 hours. The reaction mixture was washed with HCl (20 ml, 1M), saturated aqueous NaHCO$_3$ (20 ml), water (3×20 ml), dried over anhydrous Na$_2$SO$_4$ and solvent removed in vacuo to give product as a crude oil (0.95 g). Purification by column chromatography over silica gel using dichloromethane and ethyl acetate (95:5) as eluant yielded compound 7 as white crystals (0.12 g, 29.7%): m.pt. 94-96° C. IR$_{vmax}$ (KBr): 3327.6 (N=C), 2929.6 (C—H stretching), 1731.7 and 1718.7 (C=O), 1654.4 (C=C stretching), 180.7 and 1195.9 (C(O)OR aromatic), 1090.4 (C—O—C) cm$^{-1}$. HRMS: Requires: 436.1008 (M$^+$+23), Found: 436.1011 (M$^+$+23). $^1$H NMR δ (CDCl$_3$): 2.36 (3H, s, OCOCH$_3$), 4.11 (9H, m, IS1-H$_2$[α+β] and IS6-H$_2$[α+β]), 6.64 (1H, d, J 4.52 Hz, ISH-3), 5.05 (1H, t, J 5.04 and 5.52 Hz, ISH-4), 5.46 (2H, dd, J 2.0 and 2.52 Hz, ISH-5 and ISH-2), 7.11 (1H, d, J 8.52 Hz, Ar$_1$H-2), 7.32 (1H, q, J 6.52, 8.04 and 8.52 Hz, Ar$_1$H-3), 7.43 (1H, q, J 6.53, 8.04 and 8.52 Hz, Ar$_1$H-5), 7.59 (1H, t, J 6.04 and 6.52 Hz, Ar$_1$H-4), 8.00 (1H, dd, J 1.52 and 2.0 Hz, Ar$_2$H-5), 8.34 (1H, m, Ar$_2$H-6), 8.82 (1H, dd, J 2.0 and 1.48 Hz, Ar$_2$H-4), 9.28 (1H, d, J 2.0 Hz, Ar$_2$H-2). $^{13}$C NMR ppm (CDCl$_3$): 20.52 (OCOCH$_3$), 79.32 (ISC-1), 72.75 (ISC-6), 74.38 (ISOC(O)Ar), 74.43 (ISC-5), 78.27 (ISC-4), 80.60 (ISC-2), 85.60 (ISC-3), 122.26 (Ar$_1$C-1), 122.88 (Ar$_1$C-4), 123.38 (Ar$_2$C-4), 125.57 (Ar$_1$C-6), 131.35 (Ar$_2$C-6), 133.83 (Ar$_1$C-2), 136.68 (Ar$_1$C-3), 150.55 (Ar$_2$C-5), 153.30 (Ar$_2$C-1), 164.13 (Ar$_1$C-5), 164.13 (Ar$_2$C-3), 170.59 (ArCOOR).

Isosorbide-2-aspirinate-5-[iso-nicotinate] 8

Isosorbide-2-aspirinate 17 (0.2 g, 0.65 mmol) was dissolved in dichloromethane (20 ml) at 0° C. to which was added DCC (0.13 g, 0.65 mmol) and DMAP (0.08 g, 0.65 mmol). After 10 mins the reaction vessel was returned to room temperature and iso-nicotinic acid (0.08 g, 0.65 mmol) was added and stirred for 24 hours. The reaction was washed with HCl (20 ml, 1M), saturated aqueous NaHCO$_3$ (20 ml), water (3×20 ml), dried over anhydrous MgSO$_4$ and solvent removed in vacuo to yield compound 8 as white powder (0.17 g, 63.1%): m.pt. 86-88° C. IR$_{vmax}$ (KBr): 3327.8 (N=C), 2929.3 (C—H stretching), 1751.8 and 1710.7 (C=O), 1628.0 (C=C stretching), 1249.0 and 1194.1 (C(O)OR aromatic), 1082.8 (C—O—C) cm$^{-1}$. HRMS: Requires: 436.1008 (M$^+$+23), Found: 436.1004 (M$^+$+23). $^1$H NMR δ

(CDCl$_3$): 2.37 (3H, s, OCOCH$_3$), 4.09 (5H, m, IS1-H$_2$[α+β] and IS6-H$_2$[α+β]), 4.65 (1H, d, J 4.52 Hz, ISH-3), 5.05 (1H, t, J 5.52 and 5.04 Hz, ISH-4), 5.46 (2H, dd, J 5.52 and 5.04 Hz, ISH-5 and ISH-2), 7.12 (1H, d, J 7.04 Hz, Ar$_1$H-2), 7.33 (1H, m, Ar$_1$H-3), 7.59 (2H, t, J 6.04 and 6.04 Hz, Ar$_1$H-5 and Ar$_1$H-4), 7.90 (1H, d, J 5.04 Hz, Ar$_2$H-6), 8.01 (H, dd, J 2.0 and 1.52 Hz, Ar$_2$H-2), 8.84 (1H, s, Ar$_2$H-5), 8.98 (1H, s, Ar$_2$H-3).

Isosorbide-2-aspirinate-5-benzyloxy benzoate 9

To a solution of isosorbide-2-aspirinate 17 (0.27 g, 0.87 mmol) in dichloromethane (20 ml) was added benzyloxy benzoic acid (0.20 g, 0.87 mmol), DCC (0.18 g, 0.87 mmol) and DMAP (0.01 g, 0.09 mmol). The reaction vessel was stirred at room temperature for 24 hours before filtering and washing the filtrate with HCl (30 ml, 0.1 M), saturated aqueous NaHCO$_3$ (30 ml) and water (2×30 ml). After drying over anhydrous Na$_2$SO$_4$, the dichloromethane was removed in vacuo to give 0.7 g of crude product as colourless oil. Purification by column chromatography over silica gel using hexane and ethyl acetate (3:1) as eluant yielded 0.19 g of compound 9 as white crystals (41.5%): m.pt. 76-78° C. IR$_{vmax}$ (KBr): 1772.7 and 1726.2 (C=O), 1276.6 (C(O)OR aromatic), 1078.1 (C—O—C) cm$^{-1}$. HRMS: Requires: 541.1475 (M$^+$+23), Found: 541.1460 (M$^+$+23). $^1$H NMR δ (CDCl$_3$): 2.05 (2H, s, ArOCH$_2$Ar), 2.36 (3H, s, OCOCH$_3$), 3.92 (1H, q, J 5.0, 5.04 and 5.0 Hz, IS6α-H), 4.02 (3H, m, IS1H[α+β]), 4.13 (1H, q, J 7.04, 7.0 and 7.56 Hz, IS6H-β), 4.62 (1H, d, J 5.0 Hz, ISH-3), 5.02 (1H, t, J 5.04 and 5.0 Hz, ISH-4), 5.19 (2H, s, ISH-5), 5.39 (2H, m, ISH-5), 7.03 (2H, m, 2×Ar—H) 7.11 (1H, d, J 7.56 Hz, Ar—H) 7.33 (2H, m, Ar—H), 7.41 (2H, t, J 6.04 and 7.04 Hz, Ar—H), 7.48 (3H, m, Ar—H) 7.58 (1H, m, Ar—H), 7.92 (1H, dd, J 1.52 and 2.0 Hz, Ar—H) 8.01 (1H, dd, J 1.48 and 2.0 Hz, Ar—H). $^{13}$C NMR ppm (CDCl$_3$): 20.49 (OCOCH$_3$), 70.12 (ISC-6), 70.19 (ISC-2), 72.59 (ISC-5), 73.84 (ISC-3), 78.28 (ArOCH$_2$), 80.48 (ISC-1), 85.59 (ISC-4), 113.18 (Ar$_2$C-5), 119.29 (Ar$_2$C-1). 120.10 (Ar$_2$C-3), 122.30 (Ar$_1$C-5), 123.41 (Ar$_1$C-1), 125.64 (Ar$_1$C-3), 126.78 (Ar$_3$C-2 and Ar$_3$C-6), 127.51 (Ar$_3$C-4), 128.08 (Ar$_3$C-3 and Ar$_3$C-6), 128.13 (Ar$_1$C-2), 131.44 (Ar$_2$C-2), 131.81 (Ar$_1$C-4) 133.44 (Ar$_2$C-4), 136.09 (Ar$_3$C-1), 150.21 (Ar$_1$C-6), 157.95 (Ar$_2$C-6), 163.16 (ArOC(O)Me), 165.20 (ArC(O)OR), 169.28 (ArC(O)OR).

Isosorbide-2-aspirinate-5-(2-aminobenzoate) 10

Isosorbide-2-aspirinate 17 (0.69 g, 2.2 mmol) was dissolved in DCM (20 mls) to which was added DCC (0.44 g, 2.2 mmol) and DMAP (0.05 g, 0.22 mmol) and the reaction vessel was stirred at 0° C. for 10 minutes. After returning to room temperature, anthranillic acid (0.29 g, 2.2 mmol) was added allowed to stir for 3 hours. The reaction mixture was washed with HCl (20 ml, 1M), saturated aqueous NaHCO$_3$ (20 ml), saturated brine solution (20 ml) and water (2×20 ml), dried over anhydrous Na$_2$SO$_4$ and solvent removed in vacuo to yield product as crude yellow oil. Purification by column chromatography over silica gel using hexane and ethyl acetate (4:1) as eluant yielded compound 10 as a yellow solid (0.39 g, 41.5%). Product was stored at 0-4° C. until required for testing. m.pt. 150-152° C. IR$_{vmax}$ (KBr): 3443.4 (N—H stretching), 2920.5 (C—H stretching), 1742.7 (C=O), 1548.0 (N—H bending), 1220.9 and 1158.6 (C(O)OR, aromatic), 1047.4 (C—O—C) cm$^{-1}$. $^1$H NMR δ (CDCl$_3$): 2.07 (3H, s, OCOCH$_3$), 4.04 (2H, m, NH$_2$), 3.88 (1H, q, J 5.52, 4.52 and 5.0 Hz, ISH-1), 4.16 (2H, m, ISH-2 and ISH-5), 4.69 (2H, dd, J 4.52 and 4.52, ISH-1 and ISH-3), 4.95 (1H, t, J 5.04 and 5.0 Hz, ISH-4), 6.69 (1H, t, J 57.52 and 7.52 Hz, Ar$_2$H-5), 6.91 (1H, t, J 8.0 and 7.04, Ar$_2$H-3), 7.01 (2H, d, J 8.52, Ar$_1$H-3 and Ar$_1$H-5), 7.31 (1H, m, Ar$_2$H-4), 7.51 (1H, m, Ar$_1$H-4), 7.82 (1H, dd, J 2.0 and 2.0 Hz, Ar$_2$H-2), 7.92 (1H, d, J 7.04, Ar$_1$H-2). $^{13}$C NMR ppm (CDCl$_3$): 20.13 (ArOCOCH$_3$), 69.82 (ISC-1), 70.02 (ISC-5), 75.01 (ISC-2), 75.03 (ISC-6), 79.29 (ISC-3), 81.86 (ISC-4), 115.02 (Ar$_2$C-5), 117.49 (Ar$_2$C-1), 119.32 (Ar$_2$C-3), 121.63 (Ar$_1$C-5), 123.59 (Ar$_1$C-1), 125.42 (Ar$_1$C-3), 130.23 (Ar$_1$C-2), 130.59 (Ar$_2$C-2), 133.27 (Ar$_1$C-4), 133.36 (Ar$_2$C-4), 147.99 (Ar$_2$C-6), 154.32 (Ar$_1$C-6), 167.02 (OCOAr), 167.06 (OCOAr), 168.92 (OCOCH$_3$).

Isosorbide-2-aspirinate-5-[2'-methoxy]-benzoate 11

Isosorbide-2-aspirinate 17 (0.2 g, 0.65 mmol) was dissolved in toluene (15 ml) at 0° C. to which was added DMAP (0.08 g, 0.65 mmol) and DCC (0.13 g, 0.65 mmol). After 10 mins the reaction vessel was returned to room temperature, 2-anisic acid (2-methoxybenzoic acid, 0.10 g, 0.65 mmol) was added and allowed to stir for 12 hours. The reaction mixture was washed with HCl (20 ml, 1M), saturated aqueous NaHCO$_3$ (20 ml), saturated brine solution (20 ml) and water (3×20 ml), dried over anhydrous Na$_2$SO$_4$ and solvent removed in vacuo to yield product as a crude oil. Purification by column chromatography over silica gel using hexane and ethyl acetate (3:1) as eluant yielded compound 11 as white crystals (0.23 g, 79.8%): m.pt. 132-134° C. IR$_{vmax}$ (KBr): 2920.5 (C—H stretching), 1764.9 and 1720.4 (C=O), 1253.2 (C(O)OR, aromatic), 1075.2 (C—O—C) cm$^{-1}$. HRMS: Requires: 465.1162 (M$^+$+23), Found: 465.1131 (M$^+$+23), $^1$H NMR δ (CDCl$_3$): 2.89 (3H, s, OCOCH$_3$) 3.95 (3H, m, ArOCH$_3$, 4.06 (1H, m, IS6-Hα), 4.14 (3H, m, IS1-H$_2$[α+β] and IS6-Hβ), 4.64 (1H, d, J 5.0 Hz, ISH-3), 5.03 (1H, t, J 5.04 and 5.52 Hz, ISH-4), 5.40 (1H, t, J 5.0 and 5.52 Hz, ISH-5), 5.45 (1H, d, J 2.0 Hz, ISH-2), 7.01 (2H, q, J 4.52, 2.52 and 6.0 Hz, Ar$_2$H-3 and Ar$_2$H-5), 7.11 (1H, d, J 8.04 Hz, Ar$_1$H-2), 7.31 (1H, m, Ar$_1$H-3), 7.50 (1H, m, Ar$_1$H-4), 7.58 (1H, m, Ar$_1$H-5), 7.88 (1H, dd, J 2.04 and 1.52 Hz, Ar$_2$H-4), 8.01 (1H, dd, J 1.52 and 1.48 Hz, Ar$_2$H-6). $^{13}$C NMR ppm (CDCl$_3$): 20.42 (ArOCOCH$_3$), 55.52 (ArOCH$_3$), 70.41 (ISC-1), 72.66 (ISC-6), 73.69 (ISOCOAr), 76.58 (ISC-5). 78.25 (ISC-4), 80.56 (ISC-2), 85.64 (ISC-3), 111.74 (Ar$_2$C-3) 118.83 (Ar$_2$C-1), 122.39 (Ar$_2$C-5), 122.91 (Ar$_1$C-5), 123.38 (Ar$_1$C-1), 125.42 (Ar$_1$C-3), 125.56 (Ar$_1$C-2), 131.38 (Ar$_2$C-6), 133.45 (Ar$_1$C-4), 133.75 (Ar$_2$C-4), 150.24 (Ar$_1$C-6), 159.09 (Ar$_2$C-6), 164.79 (ArCOOR), 169.13 (ArOC(O)CH$_3$).

Isosorbide-2-aspirinate-5-[3'-methoxy]-benzoate 12

Isosorbide-2-aspirinate 17 (0.2 g, 0.65 mmol) was dissolved in toluene (15 ml) at 0° C. to which was added DMAP (0.08 g, 0.65 mmol) and DCC (0.13 g, 0.65 mmol). After 10 mins the reaction vessel was returned to room temperature, 3-anisic acid (3-methoxybenzoic acid) (0.10 g, 0.65 mmol was added and allowed to stir for 12 hours. The reaction mixture was washed with HCl (20 ml, 1M), saturated aqueous NaHCO$_3$ (20 ml), saturated brine solution (20 ml) and water (3×20 ml), dried over anhydrous Na$_2$SO$_4$ and solvent removed in vacuo to yield product as a crude oil. Purification by column chromatography over silica gel using hexane and ethyl acetate (3:1) as eluant yielded compound 12 as white crystals (0.23 g, 79.8%): m.pt. 125-128° C. IR$_{vmax}$ (KBr): 2980.9 (C—H stretching), 1768.3 and 1723.8 (C=O), 1298.5 and 1253.5 (C(O)OR, aromatic), 1075.9 (C—O—C) cm$^{-1}$. HRMS: Requires: 465.1162 (M$^+$+23), Found:

465.1168 (M$^+$+23), $^1$H NMR δ (CDCl$_3$): 2.36 (3H, s, OCOCH$_3$) 3.87 (3H, s, ArOCH$_3$), 4.05 (1H, d, J 5.0 Hz, IS6-Hα), 4.09 (2H, t, J 3.0 and 2.52 Hz, IS1-H$_2$[α+β]), 4.14 (2H, d, J 7.52 Hz, IS6-Hβ), 4.64 (1H, d, J 5.04 Hz, ISH-3), 5.03 (1H, t, J 5.04 and 5.52 Hz, ISH-4), 5.43 (1H, q, J 5.0, 5.52 and 5.52 Hz, ISH-5), 5.47 (1H, s, ISH-2), 7.13 (2H, q, J 4.52, 2.52 and 6.0 Hz, Ar$_2$H-3 and Ar$_2$H-5), 7.33 (2H, m, Ar$_1$H-2 and Ar$_1$H-3), 7.58 (2H, m, Ar$_1$H-4 and Ar$_1$H-5), 7.69 (1H, d, J 7.52 Hz, Ar$_2$H-4), 8.01 (1H, dd, J 1.52 and 1.52 Hz, Ar$_2$H-6). $^{13}$C NMR ppm (CDCl$_3$): 20.41 (ArOCOCH$_3$), 54.99 (ArOCH$_3$), 70.43 (ISC-1), 72.74 (ISC-6), 74.05 (ISOCOAr), 76.58 (ISC-5), 78.17 (ISC-4), 80.49 (ISC-2), 85.67 (ISC-3), 113.96 (Ar$_2$C-2), 119.21 (Ar$_2$C-4), 121.67 (Ar$_1$C-5), 122.34 (Ar$_2$C-6), 123.38 (Ar$_1$C-1), 125.56 (Ar$_1$C-3), 129.03 (Ar$_2$C-5), 130.39 (Ar$_1$C-2), 131.36 (Ar$_2$C-1), 133.77 (Ar$_1$C-4), 150.24 (Ar$_1$C-6), 159.20 (Ar$_2$C-3), 163.14 (ArCOOR), 169.11 (ArOCOCH$_3$).

Isosorbide-2-aspirinate-5-[4-methoxy]-benzoate 13

Isosorbide-2-aspirinate 17 (0.2 g, 0.65 mmol) was dissolved in toluene (15 ml) at 0° C. to which was added DMAP (0.08 g, 0.65 mmol) and DCC (0.13 g, 0.65 mmol). After 10 mins the reaction vessel was returned to room temperature, 4-anisic acid (4-methoxybenzoic acid) (0.10 g, 0.65 mmol) was added and allowed to stir for 12 hours. The reaction mixture was washed with HCl (20 ml, 1M), saturated aqueous NaHCO$_3$ (20 ml), saturated brine solution (20 ml) and water (3×20 ml), dried over anhydrous Na$_2$SO$_4$ and solvent removed in vacuo to yield product as a crude oil. Purification by column chromatography over silica gel using hexane and ethyl acetate (2:1) as eluant yielded product as white crystals (0.17 g, 58.9%): m.pt. 141-144° C. IR$_{vmax}$ (KBr): 2994.1 and 2936.7 (C—H stretching), 1764. and 724.9 (C=)), 1605.8 (C=C stretching), 1260.5 (C(O)OR, aromatic), 1078.6 (C—O—C) cm$^{-1}$. HRMS: Requires: 465.1162 (M$^+$+23), Found: 465.1157 (M$^+$+23). $^1$H NMR δ (CDCl$_3$): 2.32 (3H, s, OCOCH$_3$), 3.84 (3H, s, ArOCH$_3$, 3.99 (1H, m, IS6-Hα), 4.07 (6H, m, IS1-H$_2$[α+β] and IS6-Hβ), 4.59 (1H, d, J 4.52 Hz, ISH-3), 4.98 (1H, t, J 5.52 and 5.0 Hz, ISH-4), 5.38 (1H, t, J 5.0 and 5.52 Hz, ISH-5), 5.43 (1H, d, J 2.0 Hz, ISH-2), 6.91 (2H, d, J 8.52 Hz, Ar$_2$H-3 and Ar$_2$H-5), 7.08 (1H, d, J 8.0 Hz, Ar$_1$H-4), 7.28 (1H, t, J 7.56 and 9.52 Hz, Ar$_1$H-2), 7.54 (1H, t, J 8.0 and 7.52 Hz, Ar$_1$H-3), 7.99 (3H, q, J 9.0, 7.04 and 8.04 Hz, Ar$_1$H-1, Ar$_2$H-2 and Ar$_2$H-6). $^{13}$C NMR ppm (CDCl$_3$): 20.48 (ArOCOCH3), 59.83 (ArOCH$_3$), 70.41 (ISC-1), 72.82 (ISC-6), 73.58 (ISOCOAr), 76.58 (ISC-5). 78.26 (ISC-4), 80.47 (ISC-2), 85.46 (ISC-3), 113.33 (Ar$_2$C-3 and Ar$_2$C-5), 121.46 (Ar$_1$C-5), 122.35 (Ar$_2$C-1), 123.36 (Ar$_1$C-1), 125.54 (Ar$_1$C-3), 131.35 (Ar$_1$C-2), 133.73 (Ar$_2$C-2 and Ar$_2$C-6), 133.76 (Ar$_1$C-4), 150.23 (Ar$_1$C-6), 163.12 (ArOCH$_3$ and Ar$_2$C-4), 165.09 (ArCOOR), 169.08 (ArCOOR), 170.52 (ArOCOCH$_3$).

Isosorbide-2-aspirinate-5-[4-methylbenzoate] 14

A solution of isosorbide-2-aspirinate 17 (0.2 g, 0.65 mmol) was dissolved in toluene at 0° C. to which was added triethylamine (0.13 mls, 0.98 mmol) and 4-toluoyl chloride (0.93 ml, 0.78 mmol). The reaction vessel was returned to room temperature and allowed to stir for 10 hours, then washed with HCl (30 ml, 1M), saturated aqueous NaHCO$_3$ (30 ml), water (3×30 ml) and saturated NaCl solution (30 ml). The reaction was dried with anhydrous Na$_2$SO$_4$ and solvent was removed in vacuo using ethyl acetate as co-solvent to give crude product. Purification by column chromatography using hexane and ethyl acetate (9:1) as eluant gave compound 14 as white crystals (0.1 g, 35.99%): m.pt. 102-104° C. IR$_{vmax}$ (KBr): 2982.7 and 2923.6 (C—H stretching), 1763.9 and 1717.8 (C=O), 1608.5 (C=C), 1275.4 and 1202.0 (C(O)OR), 1100.3 (C—O—C)) cm$^{-1}$. HRMS: Requires: 449.1212 (M$^+$+23), Found: 449.1229 (M$^+$+23), $^1$H NMR δ (CDCl$_3$): 2.19 (3H, s, OCOCH$_3$), 2.43 (3H, s, Ar—CH$_3$), 4.05 (2H, d, J 5.0 Hz, IS1H$_2$[α+] and IS6H$_2$[α+]), 4.09 (2H, t, J 4.04 and 3.52 Hz, ISH-6), 4.14 (1H, t, J 7.04 and 7.52 Hz, ISH-5), 4.63 (1H, d, J 5.0 Hz, ISH-3), 5.03 (1H, t, J 4.8 and 5.0, ISH-4), 5.44 (2H, m, ISH-2), 7.11 (1H, d, J 8.04 Hz, Ar—H), 7.27 (2H, d, J 8.56 Hz, Ar—H), 7.33 (1H, t, J 7.52 and 7.52 Hz, Ar—H), 7.55 (1H, t, J 1.52 and 6.04 Hz, Ar—H), 8.00 (3H, m, Ar—H). $^{13}$C NMR ppm (CDCl$_3$): 13.71 (ArCH$_3$), 20.54 (OCOCH$_3$), 70.49 (ISC-1), 72.75 (ISC-6), 73.78 (ISC-5), 78.13 (ISC-4), 80.72 (ISC-2), 85.62 (ISC-3), 122.25 (Ar$_1$C-1), 123.38 (Ar$_1$C-4), 125.64 (Ar$_1$C-6), 126.26 (Ar$_1$C-2 and Ar$_2$C-4), 128.74 (Ar$_2$C-2 and Ar$_2$C-5), 129.36 (Ar$_2$C-6), 131.42 (Ar$_2$C-3), 133.87 (Ar$_1$C-3), 143.62 (Ar$_2$C-1), 150.22 (Ar$_1$C-5), 163.15 (ArOCOCH$_3$), 165.48 (IS—OCOAr), 169.27 (ArCOO).

Isosorbide-2-aspirinate-5-(4-nitrobenzoate) 15

(Please note a compound 16 is not included in this description)

Isosorbide-2-aspirinate 17 (0.2 g, 0.65 mmol) was dissolved in DCM (10 mls) at room temperature. To the reaction vessel was added 4-nitrobenzoylchloride (0.15 g, 0.78 mmol) and triethylamine (1.12 ml, 0.78 mmol). The reaction was allowed to stir at room temperature for 48 hours before washing with HCl (20 ml, 1M), saturated aqueous NaHCO$_3$ (25 ml), saturated brine solution (20 ml) and water (2×20 ml), dried over anhydrous Na$_2$SO$_4$ and solvent removed in vacuo to yield product as a crude yellow oil. Purification by column chromatography over silica gel using hexane and ethyl acetate (3:2) as eluant yielded compound 15 as a colourless oil which when recrystallised in ethanol afforded product as white crystals (0.15 g, 50.5%). m.pt. 66-68° C. IR$_{vmax}$ (KBr): 1772.7 and 1726.2 (C=O), 1276.6 (C(O)OR, aromatic), 1078.1 (C—O—C) cm$^{-1}$. HRMS: Requires: 480.0907 (M$^+$+23), Found: 480.0922 (M$^+$+23), $^1$H NMR δ (CDCl$_3$): 2.34 (3H, s, OCOCH$_3$), 4.07 (4H, m, ISH-3), 4.64 (1H, d, J 4.52 Hz, ISH-1 and ISH-4), 5.04 (1H, t, J 5.04 and 5.0 Hz, ISH-5), 5.45 (2H, m, ISH-2 and ISH-6), 7.10 (1H, dd, J 1.0 and 1.0 Hz, Ar$_1$H-2), 7.31 (1H, m, Ar$_1$H-3), 7.53 (1H, m, Ar$_1$H-4), 7.99 (1H, dd, J 2.04 and 1.52 Hz, Ar$_1$H-5), 8.25 (4H, dd, J 2.0 and 2.04 Hz, Ar$_2$H-2 and Ar$_2$H-6), 8.31 (2H, dd, J 2.0 and 2.04 Hz, Ar$_2$H-3 and Ar$_2$H-5). $^{13}$C NMR ppm (CDCl$_3$): 20.41 (ArOCOCH$_3$), 70.26 (ISC-1), 72.76 (ISC-5), 74.88 (ISC-2 and ISC-6), 80.52 (ISC-4), 85.68 (ISC-3), 123.16 (Ar$_1$C-5), 123.36 (Ar$_1$C-1), 125.58 (Ar$_2$C-3 and Ar$_2$C-5), 130.39 (Ar$_1$C-2), 131.32 (Ar$_2$C-2 and Ar$_2$C-6), 133.87 (Ar$_1$C-4), 150.32 (Ar$_2$C-4), 163.07 (OCOAr), 163.53 (OCOAr), 169.09 (OCOCH$_3$).

Isosorbide-2-aspirinate-5-OH 17

A stirred solution of acetylsalicyloyl chloride (m.w. 198.60 g/mol, 10.9 g=54.9 mmol) in dichloromethane (160 ml) was treated with triethylamine (m.w. 101.19 g/mol, d=0.726 g/ml, 9.1 ml=65.4 mmol). The mixture was cooled to 0° C. and 5-ISMN (m.w. 191.12 g/mol, 10 g=52.3 mmol) was added. The flask was stirred at room temperature overnight and protected from light. Mixture was washed with HCl (2 M), 5% NaHCO$_3$ and water, dried over sodium sulfate and concentrated to an oil. This was recrystallised using hot ethanol (crystallization can be quite slow) to give 10 g of yellow crystals. This was dissolved in methanol/ethyl acetate (1:1), Pd/C was added and a hydrogen balloon was attached. Stirred overnight and monitored by TLC (hexane/ethyl acetate 2:1) to determine reaction completion. Mixture was filtered and the solvent removed. Some dichloromethane added and concentrated, diethyl ether added, allowed to stand for 10-15 mins and concentrated to white crystals (7.4 g). $^1$H NMR δ (CDCl$_3$) 400 MHz: 2.37 (3H, s, OCOCH$_3$), 3.6 (1H, m, ISH-6), 3.9 (1H, m ISH-6'), 4.07 (2H, 2×dd, ISH-1/H-1'), 4.3 (1H, q, ISH-3), 4.58 (1H, d, ISH-4), 4.69 (1H, m, ISH-2), 5.45 (1H, d, ISH-5), 7.11 (1H, d, Ar—H), 7.28 (1H, t, Ar—H), 7.57 (1H, t, Ar—H), 8.00 (1H, dd, Ar—H). $^{13}$C NMR ppm (CDCl$_3$) 400 MHz: 20.48 (OCOCH$_3$), 71.56 (ISC-1), 72.91 (ISC-6), 73.11 (ISC-5), 78.44 (ISC-2), 81.56 (ISC-4), 85.09 (ISC-3), 122.18 (Ar$_2$C-2/C-6), 123.42, 125.66 (Ar$_2$C-4), 131.37 (Ar$_1$C-4), 133.95, 150.23 (Ar$_2$OCO), 163.03 (OCOArCH$_2$ONO$_2$), 169.27 (ArC(O)OR).

Isosorbide-2-aspirinate-5-(3-(2-bromo-acetoxy))-benzoate 18

To a solution of isosorbide-2-aspirinate-5-salicylate (0.15 g, 0.35 mmol) and DBU (0.052 ml, 0.35 mmol) in dichloromethane (5 ml) was added bromoacetyl chloride (0.03 ml, 0.35 mmol) and the reaction mixture was allowed to stir overnight. The reaction was washed with water (2×5 ml) and the solvents removed in vacuo to yield compound 18 as a colourless oil (0.13 g). IR$_{Vmax}$ (film) cm$^{-1}$: 1765.6 and 1724.3 (C=O), 1608.1 (C=O), 1288.4 and 1251.4 (C(O)OR), 1196.9 and 1135.6 (C—O—C), 732.6 (C—Br). HRMS: Requires: 531.1013 (M$^+$); Found: 570.4453 (M$^+$+23). δH (400 MHz; CDCl$_3$): 2.37 (3H, s, OCOCH$_3$), 4.07 (4H, m, IS1, 6-H), 4.48 (2H, s, CH$_2$), −4.63 (1H, m, IS4-H), 4.98 (1H, m, IS3-H), 5.40 (2H, m, IS2, 5-H), 7.11 (1H, d, J8.0 and 7.5 Hz, Ar—H), 7.60 (2H, m, 2×ArH), 8.11 (1H, d, J1.5 Hz, Ar—H), 8.12 (1H, d, J 1.5 Hz, Ar—H); δ$^{13}$C (100 MHz; CDCl$_3$): 20.86 (OCOCH$_3$), 40.99 (CH2), 70.47 (IS—C), 73.24 (IS6-C), 74.69 (IS4-C), 78.40 (IS3-C), 81.09 (IS5-C), 86.07 (IS2-C), 123.61, 123.83, 126.01, 126.65 and 131.78, 132.21, 134.26, 134.42, 150.23, 150.69, 163.5, 166.11, 169.55.

Isosorbide-2-aspirinate-5-cyclopropanoate 19

Cycolpropane carbonyl chloride (m.w. 104.54 g/mol, d=1.152 g/ml, 250 μl=2 mmol) was dissolved in DCM (10 ml). Triethylamine (500 μl=6 mmol) was added and the mixture was cooled to 0° C. Isosorbide-2-aspirinate, 17 was added (506.2 mg=1.6 mmol) and the reaction was stirred overnight at room temperature. Washed with 2 M HCl (10 ml), 5% NaHCO$_3$ (10 ml) and water (10 ml). Dried over sodium sulfate and concentrated. Purified by column chromatography (hexane/ethyl acetate 2:1) Rf=0.3 to give 396 mg of an oil. $^1$H NMR δ (CDCl$_3$) 400 MHz: 0.9-1.18 (2×dd and t, 4H, 2×CH$_2$), 2.32 (3H, s, OCOCH$_3$), 3.78 (m, 1H, IsH-1), 3.9 (m, 1H, IsH-6), 4.06 (2H, d, ISH-1' and ISH-6'), 4.5 (1H, d, ISH-3), 4.83 (1H, t, ISH-4), 5.12 (1H, q, IsH-2), 5.38 (1H, s, H-5), 7.06 (1H, d, Ar—H), 7.26 (1H, t, Ar—H), 7.52 (1H, t, Ar—H), 7.95 (1H, d, Ar—H). $^{13}$C NMR ppm (CDCl$_3$) 400 MHz: 9 and 10 (2×CH$_2$), 12.15 (CH), 20.43 (OCOCH$_3$), 69.96 (ISC-1), 72.71 (ISC-6), 73.40 (ISC-5), 78.14 (ISC-2), 80.39 (ISC-4), 85.35 (ISC-3), 122.20 (ArC-6), 123.37 (ArC-2), 125.59 (ArC-4), 131.36 (ArC-3), 133.86 (ArC-5), 150.19 (ArC-1), 163.05 (Ar$_2$OCO), 169.18 (CH$_3$OCOAr), 173.78 (OCOcyclopropane).

Isosorbide-2-aspirinate-5-(p-cyanobenzoate) 20

Isosorbide-2-aspirinate 17 (200 mg, 0.6 mmol) and 4-cyanobenzoylchloride (120 mg, 0.72 mmol) were reacted together according to GP2 to give 213 mg (81%) of a yellow oil after flash chromatography with EtOac:Hex 1:4. $^1$H NMR (CDCl$_3$, 400 MHz) δ 8.2 (2H, d, J=8.5 Hz), 8.0 (1H, dd, J=8 Hz, 1.5 Hz), 7.8 (2H, d, J=10 Hz), 7.6 (1H, dt, J=8 Hz, 1.5 Hz), 7.35 (1H, dt, J=6.5 Hz, 1 Hz), 7.1 (1H, d, J=8.5 Hz), 5.45 (2H, m), 5.05 (1H, t, J=5 Hz), 4.65 (1H, d, J=5 Hz), 4.1 (4H, m), 2.4 (3H, s). $^{13}$C NMR (CDCl$_3$ 400 MHz) δ 169.3, 163.8, 163.1, 150.3, 133.9, 132.8, 131.9, 131.4, 129.8, 125.7, 123.4, 122.1, 117.4, 116.3, 85.7, 80.7, 80.5, 77.9, 76.8 74.8, 72.7, 70.3, 20.5. HRMS (EI) C$_{23}$H$_{19}$O$_8$N, [M+H]$^+$ requires 438.4068, found 438.4183. Anal. C$_{23}$H$_{19}$O$_8$N requires C, 63.16; H, 4.38; N, 3.20. found C, 63.46; H, 4.51; N, 2.97.

Isosorbide-2aspirnate-5-(p-phenylbenzoate) 21

Isosorbide-2-aspirinate 17 (200 mg, 0.6 mmol) and 4-phenylbenzoylchloride (156 mg, 0.72 mmol) were reacted together to give 185 mg (65%) of a colourless oil after flash chromatography with EtOac:Hex 1:4. $^1$H NMR (CDCl$_3$, 400 MHz) δ 8.2 (2H, d, J=8.5 Hz), 8.0 (1H, dd, J=8 Hz, 1.5 Hz), 7.7 (2H, d, J=8.5 Hz), 7.65 (2H, d, J=7 Hz), 7.6 (1H, dt, J=8 Hz, 1.5 Hz), 7.5 (2H, t, J=7.5 Hz), 7.45 (1H, t, J=8 Hz), 7.35 (1H, dt, J=6.5 Hz, 1 Hz), 7.1 (1H, d, J=8.5 Hz), 5.45 (2H, m), 5.05 (1H, t, J=5 Hz), 4.65 (1H, d, J=5 Hz), 4.1 (4H, m), 2.4 (3H, s). $^{13}$C NMR (CDCl$_3$ 400 MHz) δ 169.3, 165.3, 163.1, 150.3, 145.6, 139.5, 133.9, 131.4, 129.8, 128.5, 127.8, 127.7, 126.8, 126.7 125.7, 123.4, 122.1, 85.7, 80.7, 78.12, 77.2, 76.8 73.9, 72.7, 70.5, 20.5. HRMS (EI) C$_{28}$H$_{24}$O$_8$, [M+H]$^+$ requires 489.4933, found 489.5021. Anal. C$_{28}$H$_{24}$O$_8$ requires C, 68.85; H, 4.95. found C, 68.88; H, 5.08.

Isosorbide-2-aspirinate-5-(6-chloronicotinate) 22

Isosorbide-2-aspirinate 17 (250 mg, 0.8 mmol) and 6-chloronicotinoylchloride (230 mg, 0.9 mmol) were reacted together according to GP2 to give 256 mg (70%) of a white solid after flash chromatography with EtOac:Hex 3:7. $^1$H NMR (CDCl$_3$, 400 MHz) δ 9.3 (1H s) 8.9 (1H, s), 8.3 (2H, d, J=8.5 Hz), 8.0 (1H, dd, J=8 Hz, 1.5 Hz), 7.6 (1H, dt, J=8 Hz, 1.5 Hz), 7.45 (1H, t, J=1 Hz) 7.35 (1H, dt, J=6.5 Hz, 1 Hz), 7.1 (1H, d, J=8.5 Hz), 5.45 (2H, m), 5.05 (1H, t, J=5 Hz), 4.65 (1H, d, J=5 Hz), 4.1 (4H, m), 2.4 (3H, s). $^{13}$C NMR (CDCl$_3$ 400 MHz) δ 169.3, 164.2, 163.1, 153.3, 150.5, 150.2, 136.8, 133.9, 131.4, 125.7, 123.4, 123.0, 122.2, 85.7, 80.6, 77.9, 76.8, 74.4, 72.8, 70.4, 20.5. HRMS (EI) C$_{21}$H$_{18}$ClNO$_8$, [M+H]$^+$ requires 448.8304, found 448.8295. Anal. C$_{21}$H$_{18}$ClNO$_8$ requires C, 56.32; H, 4.05; N, 3.13. found C, 56.20; H, 4.21; N, 3.02.

Isosorbide-2-aspirinate-5-(-2-chloro-6-methyl-pyridine-4-oate) 23

Isosorbide-2-aspirinate 17 (250 mg, 0.8 mmol) and 2-chloro-6-methylpyridine-4-carbamoylchloride (247 mg, 0.9 mmol) were reacted together according to GP2 to give 196 mg (53%) of a white foam after flash chromatography with EtOac:Hex 2:6. $^1$H NMR (CDCl$_3$, 400 MHz) δ 8.0 (1H, dd, J=8 Hz, 1.5 Hz), 7.74 (1H, s), 7.68 (1H, s) 7.6 (1H, dt, J=8 Hz, 1.5 Hz), 7.45 (1H, t, J=1 Hz) 7.35 (1H, dt, J=6.5 Hz, 1 Hz), 7.1 (1H, d, J=8.5 Hz), 5.45 (2H, m), 5.05 (1H, t, J=5 Hz), 4.65 (1H, d, J=5 Hz), 4.1 (4H, m), 2.65 (3H, s), 2.4 (3H, s). $^{13}$C NMR (CDCl$_3$ 400 MHz) δ 169.3, 163.1, 151.1, 150.2, 139.3, 134.0, 131.4, 125.7, 123.4, 122.1, 120.8, 120.4, 85.7, 80.4, 77.8, 77.6, 75.1, 72.8, 70.2, 23.8, 20.5. HRMS (EI) C$_{22}$H$_{20}$ClNO$_8$, [M+H]$^+$ requires 462.8570, found 462.8601.

Anal. C$_{22}$H$_{20}$ClNO$_8$ requires C, 57.21; H, 4.36; N, 3.03. found C, 56.91; H, 4.38; N, 2.94.

Isosorbide-2-aspirinate-5-(-3,5-ethoxybenzoate) 24

Isosorbide-2-aspirinate 17 (200 mg, 0.65 mmol) and 3,5-ethoxybenzoyl chloride (157 mg, 0.72 mmol) were reacted together according to GP2 to give 296 mg (74%) of a viscous yellow oil after flash chromatography with EtOac:Hex 1:4. $^1$H NMR (CDCl$_3$, 400 MHz) δ 8.1 (1H, d, J=8 Hz, Asp H5), 7.6 (1H, dt, J=8 Hz, 1.5 Hz, Asp H4), 7.35 (1H, t, J=1 Hz, Asp H3), 7.2 (2H, d, 1 Hz, Benz H2+6), 7.1 (1H, d, 8.5 Hz, Asp H2), 6.7 (1H, t, J=2.25 Hz, Benz H4), 5.45 (2H, m, IS H5+H2), 5.05 (1H, t, J=5 Hz, IS H4), 4.65 (1H, d, J=5.5 Hz, IS H3), 4.05 (8H, m, IS1-H$_2$ [α+β], IS6-H$_2$ [α+β], ethoxy-CH$_2$), 2.4 (3H, s, Acet-CH$_3$), 1.45 (6H, t, J=3.5 Hz, Eto-CH$_3$). $^{13}$C NMR (CDCl$_3$ 400 MHz) δ 169.8, 165.8, 163.6, 160.0, 150.7, 134.3, 131.9, 131.1, 126.1, 123.8, 122.7, 107.9, 106.6, 86.1, 81.1, 78.6, 76.7, 74.5, 73.2, 71.0, 63.8, 61.2, 20.9, 14.8. HRMS (EI) C$_{26}$H$_{28}$O$_{10}$, [M+H]$^+$ requires 500.4945, found 500.4932. Anal. C$_{26}$H$_{28}$O$_{10}$ requires C, 62.39; H, 5.64. found C, 62.45; H, 5.79.

Isosorbide-2-aspirinate-5-(-3-methyl-isoxazole-4-oate) 25

Isosorbide-2-aspirinate 17 (200 mg, 0.65 mmol) and 3-methyl-isoxazole-4-carboxylic acid (127 mg, 0.72 mmol) were reacted together according to GP1 to give 228 mg (83%) of a white foam after flash chromatography with EtOac:Hex 1:3. $^1$H NMR (CDCl$_3$, 400 MHz) δ 8.55 (1H, s, isox), 8.0 (1H, d, J=8 Hz, Asp H5), 7.65 (1H, dt, J=8 Hz, 1.5 Hz, Asp H4), 7.3 (1H, t, J=1 Hz, Asp H3), 7.1 (1H, d, 8.5 Hz, Asp H2), 5.4 (2H, m, IS H5+H2), 5.0 (1H, t, J=5 Hz, IS H4), 4.6 (1H, d, J=5.5 Hz, IS H3), 4.1 (4H, m, IS1-H$_2$ [α+β], IS6-H$_2$ [α+β]), 3.8 (3H, s, isox-CH$_3$), 2.35 (3H, s, Asp-acet-CH$_3$). $^{13}$C NMR (CDCl$_3$ 400 MHz) δ 169.2, 163.0, 160.4, 150.2, 149.6, 133.9, 131.4, 125.6, 123.4, 122.1, 85.6, 80.5, 73.9, 72.7, 70.2, 33.5, 24.5, 20.5, 12.3.

Isosorbide-2-aspirinate-5-(-4-methyl-1,2,3-thiadiazole-5-oate) 26

Isosorbide-2-aspirinate 17 (200 mg, 0.65 mmol) and 4-methyl-1,2,3-thiadiazole-5-carboxylic acid were reacted together to give 228 mg (83%) of a pale pink foam after flash chromatography with EtOac:Hex 1:3. $^1$H NMR (CDCl$_3$, 400 MHz) δ 8.1 (1H, d, J=8 Hz, Asp H5), 7.7 (1H, dt, J=8 Hz, 1.5 Hz, Asp H4), 7.35 (1H, t, J=1 Hz, Asp H3), 7.15 (1H, d, 8.5 Hz, Asp H2), 5.5 (2H, m, IS H5+H2), 5.05 (1H, t, J=5 Hz, IS H4), 4.65 (1H, d, J=5.5 Hz, IS H3), 4.1 (4H, m, IS1-H$_2$ [α+β], IS6-H$_2$ [α+β]), 3.05 (3H, s, thiad-CH$_3$), 2.4 (3H, s, Asp-acet-CH$_3$). $^{13}$C NMR (CDCl$_3$ 400 MHz) δ 169.7, 163.5, 162.9, 159.1, 150.7, 134.4, 131.8, 126.1, 123.8, 122.5, 86.2, 80.9, 78.2, 75.9, 73.2, 70.8, 21.0, 14.1.

Isosorbide-2-aspirinate-5-(N-Boc-isonipecotate) 27

Isosorbide-2-aspirinate 17 (200 mg, 0.65 mmol) and 4N-Boc-isonipecotic acid (162 mg, 0.72 mmol) were reacted together to give 166 mg (49%) of an off white oil after flash chromatography with MeOH:DCM 3:97. $^1$H NMR (CDCl$_3$, 400 MHz) δ8.1 (1H, d, J=8 Hz, Asp H5), 7.7 (1H, dt, J=8 Hz, 1.5 Hz, Asp H4), 7.35 (1H, t, J=1 Hz, Asp H3), 7.15 (1H, d, 8.5 Hz, Asp H2), 5.5 (1H, d, J=1.5 Hz IS H2), 5.5, (1H, dd, J=5 Hz, 1 Hz) 4.95 (1H, t, J=5 Hz, IS H4), 4.65 (1H, d, J=5.5 Hz, IS H3), 4.1 (8H, m, IS1-H$_2$ [α+β], IS6-H$_2$ [α+β], 4 nip H), 2.6 (1H, m, nip-methine-H), 2.4 (3H, s, Asp-Acet-CH$_3$), 1.7 (4H, m, 4 nip H), 1.5, (9H, s, t-Bu). $^{13}$C NMR (CDCl$_3$ 400 MHz) δ 173.9, 169.8, 163.5, 154.7, 150.7, 134.4, 131.9, 126.1, 123.9, 122.6, 85.9, 80.7, 79.6, 78.5, 77.2, 76.5, 73.9, 73.0, 70.7, 42.9, 40.9, 28.4, 28.1, 27.9, 20.9. HRMS (EI) C$_{26}$H$_{33}$O$_{10}$N, [M+H]$^+$ requires 520.4616, found 520.4631. Anal. C$_{26}$H$_{33}$O$_{10}$N requires C, 60.11; H, 6.40; N, 2.69. found C, 60.15; H, 6.79; N, 2.76.

Isosorbide-2aspirinate-5-(m-acetamidobenzoate) 28

Isosorbide-2-aspirinate 17 (200 mg, 0.65 mmol) and m-acetamidobenzoic acid (128 mg, 0.72 mmol) were reacted together to give 202 mg (66%) of a white solid after flash chromatography with MeOH:DCM 3:97. $^1$H NMR (CDCl$_3$, 400 MHz) δ8.0 (3H, m, Asp H5, Ar H2+4), 7.85 (1H, d, J=8 Hz, Ar H6), 7.6 (1H, dt, J=8 Hz, 1.5 Hz, Asp H4), 7.45 (1H, t, J=7.5 Hz, Ar H5), 7.35 (1H, t, J=1 Hz, Asp H3), 7.15 (1H, d, 8.5 Hz, Asp H2), 5.5 (2H, m, IS H5+H2), 5.05 (1H, t, J=5 Hz, IS H4), 4.65 (1H, d, J=5.5 Hz, IS H3), 4.1 (4H, m, IS1-H$_2$ [α+β], IS6-H$_2$ [α+β]), 2.4 (3H, s, Asp-Acet-CH$_3$), 2.2 (3H, Ar-acet-CH$_3$). $^{13}$C NMR (CDCl$_3$ 400 MHz) δ 169.3, 168.0, 165.0, 163.1, 150.2, 137.7, 133.9, 131.4, 129.7, 128.9, 125.6, 125.0, 124.4, 123.4, 122.2, 120.2, 85.7, m80.7, 78.1, 74.12, 72.8, 70.4, 60.0, 24.2, 20.5, 13.8. HRMS (EI) C$_{24}$H$_{23}$O$_9$N, [M+H]$^+$ requires 470.4392, found 470.4403. Anal. C$_{24}$H$_{23}$O$_9$N requires C, 61.41; H, 4.93; N, 2.98. found C, 61.52; H, 5.09; N, 2.86.

Isosorbide-2-aspirinate-5-(m-benzyloxybenzoate) 29

Isosorbide-2-aspirinate 17 (250 mg, 0.8 mmol) and m-benzyloxybenzoic acid (182 mg, 0.88 mmol) were reacted together according to GP1 to give 346 mg (85%) of a white solid after flash chromatography with EtOac:Hex 1:2. $^1$H NMR (CDCl$_3$, 400 MHz) δ 8.0 (1H, d, J=8 Hz, Asp H5), 7.7 (3H, m, Asp H4, Ar2H), 7.35 (2H, m, Asp H3, ArH), 7.1 (2H, m, Asp H2, ArH), 7.25 (5H, m, BnH), 5.5 (3H, m, IS H2, Bn-CH$_2$), 5.05 (1H, t, J=5 Hz, IS H4), 4.65 (1H, d, J=5.5 Hz, IS H3), 4.1 (4H, m, IS1-H$_2$ [α+β], IS6-H$_2$ [α+β]), 2.4 (3H, s, Asp-Acet-CH$_3$). $^{13}$C NMR (CDCl$_3$ 400 MHz) δ 169.76, 165.2, 163.6, 150.7, 135.8, 134.4, 133.7, 132.9, 131.9, 130.8, 130.3, 130.2, 129.2, 126.1, 123.9, 122.7, 97.7, 86.1, 81.1, 78.5, 74.7, 73.2, 70.8, 43.9, 20.9. HRMS (EI) C$_{29}$H$_{26}$O$_9$, [M+H]$^+$ requires 518.4344, found 518.4357. Anal. C$_{29}$H$_{26}$O$_9$ requires C, 67.19; H, 5.05. found C, 67.28; H, 5.09.

Isosorbide-2-aspirinate-5-(p-benzyloxybenzoate) 30

Isosorbide-2-aspirinate (250 mg, 0.8 mmol) and m-benzyloxybenzoic acid (182 mg, 0.88 mmol) were reacted together according to GP1 to give 346 mg (85%) of a white solid after flash chromatography with EtOac:Hex 1:2. $^1$H NMR (CDCl$_3$, 400 MHz) δ 8.0 (1H, d, J=8 Hz, Asp H5), 7.7 (1H, dt, J=8 Hz, 1.5 Hz, Asp H4), 7.45 (m, 4H, ArH), 7.35 (1H, t, J=1 Hz, Asp H3), 7.25 (5H, m, BnH) 7.1 (1H, d, 8.5 Hz, Asp H2), 5.5 (3H, m, IS H2, Bn-CH$_2$), 5.05 (1H, t, J=5 Hz, IS H4), 4.65 (1H, d, J=5.5 Hz, IS H3), 4.1 (4H, m, IS1-H$_2$ [α+β], IS6-H$_2$ [α+β]), 2.4 (3H, s, Asp-Acet-CH$_3$). $^{13}$C NMR (CDCl$_3$ 400 MHz) δ 169.76, 165.2, 163.6, 150.7, 136.9, 135.2, 133.0, 132.2, 131.9, 130.8, 130.3, 130.2, 129.2, 126.1, 123.9, 122.7, 97.7, 86.1, 81.1, 78.5, 74.7, 73.2, 70.8, 43.9, 20.9. HRMS (EI) C$_{29}$H$_{26}$O$_9$, [M+H]$^+$ requires 518.4344, found 518.4338. Anal. C$_{29}$H$_{26}$O$_9$ requires C, 67.19; H, 5.05. found C, 67.35; H, 5.18.

Isosorbide-2-aspirinate-5-(2-nitrooxy-methyl)benzoate 31

Figure 12:
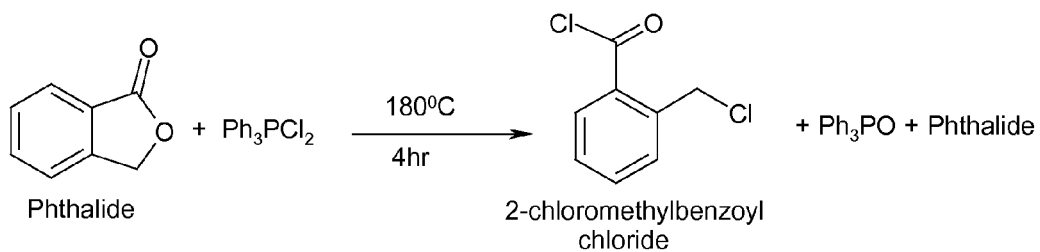
FIG. 12: Synthetic route for preparation of 2-chloromethylbenzoyl chloride

Phthalide (m.w. 134.13 g/mol, 5.03 g=37 mmol) and dichlorotriphenylphosphorane (m.w. 333.19 g/mol, 12.3 g=38 mmol) were heated at 180° C. for 4 hrs with stirring[3]. Colour change from green to brown was seen over the course of 4 hrs. TLC (hexane/ethyl acetate 2:1) showed 3 spots and NMR determined that the top spot (Rf 0.77) was that of 2-chloromethylbenzoyl chloride, the second spot (Rf 0.57) was phthalide and the bottom spot (Rf 0.14) was triphenylphosphorous. A large amount of the phthalide was unreacted. 2-chloromethylbenzoyl chloride (FIG. 12) (m.w. 189.04 g/mol, 600 µl) was dissolved in dichloromethane (10 ml). Triethylamine (m.w. 101.19 g/mol, d=0.726 g/ml, 600 µl=4.3 mmol) was added and the mixture was cooled to 0° C. Compound 17 (m.w. 308.14 g/mol, 0.5298 g=1.7 mmol) was added and the mixture was stirred at room temperature overnight while protected from light. The mixture (green colour) was washed with HCl (2 M, 10 ml), 5% NaHCO$_3$ (10 ml) and distilled water (10 ml) and dried over sodium sulfate. Mixture was concentrated producing 769.5 mg of a brown/green oil. This was chromatographed using hexane/ethyl acetate (2:1) resulting in 419.4 mg of a brown solid (Rf 0.38). $^1$H NMR δ (CDCl$_3$) 400 MHz: 2.38 (3H, s, OCOCH$_3$), 4.03 (4H, m, ISH-1, ISH-1', ISH-6 and ISH-6'), 4.66 (1H, d, ISH-3), 5.04 (2H, m, CH$_2$Cl), 5.10 (1H, ss, ISH-4), 5.42 (2H, m, ISH-2/H-5), 7.12 (1H, d, Ar—H), 7.28 (1H, m, Ar—H), 7.42 (1H, m, Ar—H), 7.6 (3H, m, Ar—H), 8.01 (2H, dd, Ar—H). $^{13}$C NMR ppm (CDCl$_3$) 400 MHz: 20.51 (OCOCH$_3$), 43.95 (CH$_2$Cl), 70.15 (ISC-1), 72.78 (ISC-6), 74.33 (ISC-5), 78.11 (ISC-2), 80.52 (ISC-4), 85.58 (ISC-3), 122.21 (Ar$_2$C-2/C-6), 123.42, 125.65 (Ar$_2$C-4), 128.03 (Ar$_1$C-6), 128.07 (Ar$_1$C-2), 130.60 (Ar$_1$C-5), 130.73 (Ar1C-1), 131.43 (Ar$_1$C-4), 133.45 (Ar$_2$C-5), 133.92, 138.54, 150.25 (Ar$_2$OCO), 163.12 (O COArCH$_2$ONO$_2$), 165.47 (ArOCOCH$_3$), 169.29 (Ar C(O)OR). 400 mg was dissolved in CH$_3$CN/THF (6 ml, 4/2 v/v) and treated with AgNO$_3$ (m.w. 169.87 g/mol, 0.30 g=1.7 mmol) and refluxed for 4 hours before stirring overnight at room temperature while protected from light. Mixture was filtered and concentrated. This was reconstituted in ethyl acetate (10 ml) and water (2 ml). The organic phase was washed with water (3×2 ml), brine (2 ml) and dried over sodium sulfate. Concentrated, producing an oil which was chromatographed using hexane/ethyl acetate (2:1) resulting in 95 mg of yellow wax-like material. $^1$H NMR δ (CDCl$_3$) 400 MHz: 2.38 (3H, s, OCOCH$_3$), 4.01 (4H, m, ISH-1, ISH-1', ISH-6 and ISH-6'), 4.65 (1H, d, ISH-3), 5.02 (1H, t, ISH-4), 5.41 (2H, m, CH$_2$), 5.86 (2H, ss, ISH-2/H-5), 7.11 (1H, d, Ar—H), 7.28 (1H, t, Ar—H), 7.49 (2H, q, Ar—H), 7.61 (2H, q, Ar—H), 8.01 (1H, d, Ar—H), 8.10 (1H, d, Ar—H). $^{13}$C NMR ppm (CDCl$_3$) 400 MHz: 20.51 (OCOCH$_3$), 70.37 (CH$_2$ONO$_2$), 72.78 (ISC-1), 73.46 (ISC-6), 74.30 (ISC-5), 78.01 (ISC-2), 80.61 (ISC-4), 85.64 (ISC-3), 122.19 (Ar$_2$C-2/C-6), 123.40, 125.66 (Ar$_2$C-4), 128.76 (Ar$_1$C-6), 129.77 (Ar$_1$C-2), 129.85 (Ar$_1$C-5), 130.30 (Ar1C-1), 131.41 (Ar$_1$C-4), 132.44 (Ar$_2$C-5), 133.25, 133.93, 150.23 (Ar$_2$OCO), 163.12 (OCOArCH$_2$ONO$_2$), 164.71 (ArOCOCH$_3$), 169.28 (ArC(O)OR).

Isosorbide-2-aspirinate-5-(3-nitrooxy-methyl)benzoate 32

3-Chloromethylbenzoyl chloride (m.w. 189.04 g/mol, d=1.33 g/ml, 500 µl=3.5 mmol) was dissolved in dichloromethane (10 ml). Triethylamine (m.w. 101.19 g/mol, d=0.726 g/ml, 600 µl=4.3 mmol) was added and the mixture was cooled to 0° C. Compound 17 (m.w. 308.14 g/mol, 0.511 g=1.6 mmol) was added and the mixture was stirred at room temperature overnight while protected from light. The mixture was washed with HCl (2 M, 10 ml), 5% NaHCO$_3$ (10 ml) and distilled water (10 ml) and dried over sodium sulfate. Mixture was concentrated producing 1.18 g of an oil. This was chromatographed using hexane/ethyl acetate (3:1) resulting in 903.4 mg of an oil (Rf 0.2). $^1$H NMR δ (CDCl$_3$) 400 MHz: 2.37 (3H, s, OCOCH$_3$), 4.06 (4H, m, ISH-1, ISH-1', ISH-6 and ISH-6'), 4.65 (3H, ds, ISH-3 and CH$_2$Cl), 5.03 (1H, t, ISH-4), 5.43 (2H, dd, ISH-2, ISH-5), 7.10 (1H, d, Ar—H), 7.32 (1H, t, Ar—H), 7.47 (1H, t, Ar—H), 7.57 (2H, m, Ar—H), 8.00 (2H, m, Ar—H), 8.10 (1H, s, Ar—H). $^{13}$C NMR ppm (CDCl$_3$) 400 MHz: 20.49 (OCOCH$_3$), 45.01 (CH$_2$Cl), 70.41 (ISC-1), 72.76 (ISC-6), 74.20 (ISC-5), 78.04 (ISC-2), 80.64 (ISC-4), 85.63 (ISC-3), 122.18 (Ar$_2$C-2/C-6), 123.39, 125.67 (Ar$_2$C-4), 128.61 (Ar$_1$C-6), 129.28 (Ar$_1$C-2), 129.36 (Ar$_1$C-5), 129.52 (Ar1C-1), 131.41 (Ar$_1$C-4), 133.02 (Ar$_2$C-5), 133.93, 137.57, 150.20 (Ar$_2$OCO), 163.16 (OCOArCH$_2$ONO$_2$), 164.94 (ArOCOCH$_3$), 169.37 (Ar C(O)OR). This was dissolved in CH$_3$CN/THF (6 ml, 4/2 v/v) and treated with AgNO$_3$ (m.w. 169.87 g/mol, 0.67 g=3.9 mmol) and refluxed for 4 hours before stirring overnight at room temperature while protected from light. Mixture was filtered and concentrated. This was reconstituted in ethyl acetate (10 ml) and water (2 ml). The organic phase was washed with water (3×2 ml), brine (2 ml) and dried over sodium sulfate. Concentrated, producing an oil which was chromatographed using hexane/ethyl acetate (1:1) resulting in 184.3 mg of yellow wax-like material. $^1$H NMR δ (CDCl$_3$) 400 MHz: 2.38 (3H, s, OCOCH$_3$), 4.09 (4H, m, ISH-1, IsH-1', IsH-6 and ISH-6'), 4.65 (1H, d, ISH-3), 5.05 (1H, t, ISH-4), 5.5 (4H, dd, ISH-2, ISH-5 and CH$_2$), 7.12 (1H, d, Ar—H), 7.29 (1H, t, Ar—H), 7.50 (3H, m, Ar—H), 7.65 (1H, d, Ar—H), 8.01 (2H, broad s, Ar—H). $^{13}$C NMR ppm (CDCl$_3$) 400 MHz: 20.51 (OCOCH$_3$), 70.37 (CH$_2$ONO$_2$), 72.78 (ISC-1), 73.46 (ISC-6), 74.30 (ISC-5), 78.01 (ISC-2), 80.61 (ISC-4), 85.64 (ISC-3), 122.19 (Ar$_2$C-2/C-6), 123.40, 125.66 (Ar$_2$C-4), 128.76 (Ar$_1$C-6), 129.77 (Ar$_1$C-2), 129.85 (Ar$_1$C-5), 130.30 (Ar1C-1), 131.41 (Ar$_1$C-4), 132.44 (Ar$_2$C-5), 133.25, 133.93, 150.23 (Ar$_2$OCO), 163.12 (OCOArCH$_2$ONO$_2$), 164.71 (ArOCOCH$_3$), 169.28 (Ar C(O)OR).

Isosorbide-2-aspirinate-5-(4-nitrooxy-methyl)benzoate 33

4-chloromethylbenzoyl chloride (m.w. 189.04 g/mol, 650 µl) was dissolved in dichloromethane (10 ml). Triethylamine (m.w. 101.19 g/mol, d=0.726 g/ml, 600 µl=4.3 mmol) was added and the mixture was cooled to 0° C. Compound 17 (m.w. 308.14 g/mol, 0.5320 g=1.7 mmol) was added and the mixture was stirred at room temperature overnight while protected from light. The mixture was washed with HCl (2 M, 10 ml), 5% NaHCO$_3$ (10 ml) and distilled water (10 ml) and dried over sodium sulfate. Mixture was concentrated and was chromatographed using hexane/ethyl acetate (2:1) resulting in 100 mg of white solid material. $^1$H NMR δ (CDCl$_3$) 400 MHz: 2.35 (3H, s, OCOCH$_3$), 4.04 (4H, m, ISH-1, IsH-1', IsH-6 and ISH-6'), 4.6 (4H, m, ISH-3 and CH$_2$Cl, imp), 5.04 (1H, d, ISH-4), 5.42 (2H, t, ISH-2, ISH-5), 7.09 (1H, d, Ar—H), 7.26 (1H, t, Ar—H), 7.47 (2H, m, Ar—H), 7.51 (1H, q, Ar—H), 8.00 (1H, d, Ar—H), 8.06 (2H, m, Ar—H). $^{13}$C NMR ppm (CDCl$_3$) 400 MHz: 20.51 (OCOCH$_3$), 44.87 (CH$_2$Cl), 70.47 (ISC-1), 72.76 (ISC-6), 74.11 (ISC-5), 78.05 (ISC-2), 80.67 (ISC-4), 85.64 (ISC-3), 122.22 (Ar$_2$C-2/C-6), 123.40, 125.65 (Ar$_2$C-4), 128.53 (Ar$_1$C-6), 128.96 (Ar$_1$C-2), 129.77 (Ar$_1$C-5), 130.16 (Ar1C-1), 130.56 (Ar$_1$C-4), 131.43 (Ar$_2$C-5), 139.91, 142.23, 150.23 (Ar$_2$OCO), 163.14 (OCOArCH$_2$ONO$_2$), 164.91 (ArO$\underline{C}$OCH$_3$), 169.31 (Ar$\underline{C}$(O)OR). This was dissolved in CH$_3$CN/THF (6 ml, 4/2 v/v) and treated with AgNO$_3$ (m.w. 169.87 g/mol, 75 mg=0.4 mmol) and refluxed for 4 hours before stirring overnight at room temperature while protected from light. Mixture was filtered and concentrated. This was reconstituted in ethyl acetate (10 ml) and water (2 ml). The organic phase was washed with water (3×2 ml), brine (2 ml) and dried over sodium sulfate. Concentrated, producing an oil which was chromatographed using hexane/ethyl acetate (2:1) resulting in 28.3 mg of off-white solid. $^1$H NMR δ (CDCl$_3$) 400 MHz: 2.35 (3H, s, OCOCH$_3$), 4.04 (4H, m, ISH-1, ISH-1', ISH-6 and ISH-6'), 4.62 (1H, d, ISH-3), 5.01 (1H, t, ISH-4), 5.41 (2H, m, CH$_2$), 5.48 (2H, s, ISH-2/H-5), 7.09 (1H, d, Ar—H), 7.31 (1H, t, Ar—H), 7.48 (2H, d, Ar—H), 7.55 (1H, t, Ar—H), 8.00 (1H, d, Ar—H), 8.10 (2H, d, Ar—H). $^{13}$C NMR ppm (CDCl$_3$) 400 MHz: 20.51 (OCOCH$_3$), 70.44 (CH$_2$ONO$_2$), 72.76 (ISC-1), 73.18 (ISC-6), 74.23 (ISC-5), 78.02 (ISC-2), 80.65 (ISC-4), 85.65 (ISC-3), 122.19 (Ar$_2$C-2/C-6), 123.41, 125.66 (Ar$_2$C-4), 128.17 (Ar$_1$C-6), 129.85 (Ar$_1$C-2), 129.92 (Ar$_1$C-5), 131.41 (Ar1C-1), 133.93 (Ar$_1$C-4), 137.19 (Ar$_2$C-5), 150.24 (Ar$_2$OCO), 163.14 (OCOArCH$_2$ONO$_2$), 164.75 (ArO$\underline{C}$OCH$_3$), 169.29 (Ar$\underline{C}$(O)OR).

Isosorbide-2-aspirinate-5-(nitrooxy)-acetate 34

To a solution of isosorbide-2-aspirinate 17 (0.49 g, 1.6 mmol) in dichloromethane (10 ml) was added DCC (0.33 g, 1.6 mmol), DMAP (0.02 g, 0.16 mmol) and nitrooxy acetic acid (0.19 g, 1.6 mmol). The mixture was stirred at room temperature overnight before filtering and washing the filtrate with HCl (2×10 ml, 0.1 M), saturated aqueous NaHCO$_3$ (2×10 ml) and water (2×10 ml). After drying over anhydrous Na$_2$SO$_4$, the dichloromethane was removed in vacuo to afford product as crude oil. Purification by column chromatography over silica gel using hexane and ethyl acetate (5:2) as eluant yielded compound 23 (0.38 g) as colorless oil. IR$_{Vmax}$ (film) cm$^{-1}$: 1759.0 and 1727.5 (C=O), 1643.6 (NO$_2$), 1287.7 (NO$_2$), 1256.3 (C(O)OR, aromatic), 1193.5 (C—O—C). HRMS: Requires 411.0802 (M$^+$), Found: (M$^+$). δH (400 MHz; CDCL$_3$): 2.36 (3H, s, OCOCH$_3$), 2.68 (1H, d, J 7.52 Hz, IS—H), 3.61 (1H, q, J 6.04, 3.52 and 6 Hz, IS—H), 3.92 (1H, q, J 6.04, 3.52 and 6 Hz, IS—H), 4.12 (2H, m, IS—H$_2$), 4.33 (1H, M, IS—H$_2$). 4.58 (1H, d, J 4 Hz, IS—H), 4.67 (1H, t, J 5 and 5.04 Hz, IS—H), 5.44 (2H, s, OCH$_2$O), 7.11 (1H, d, J 8.04 Hz, Ar—H), 7.33 (1H, t, J 8 and 7.52 Hz, Ar—H), 7.59 (1H, t, 7.06 and 8.26 Hz, Ar—H), 8.01 (1H, d, J 6.52 Hz, Ar—H). δ$^{13}$C (100 MHz; CDCL$_3$): 20.91 (OCOCH$_3$), (CH$_2$), 72.36 (IS—C), 73.41 (IS—C), 73.69 (IS—C), 78.96 (IS—C), 82.04 (IS—C), 85.64 (IS—C), 122.77 (ArC-1), 123.89, 126.07, 131.81 and 134.31 (aromatic methine), 150.74 (CO), 163.51 (ArO$\underline{C}$(O)Me), 169.59 (Ar$\underline{C}$(O)OR).

Isosorbide-2-aspirinate-5-mononitrate ISMNA

To a solution of IS-5-MN (5 g, 26.65 mmol) in toluene (100 ml) at 0° C. was added triethylamine (5.52 ml, 3.96 mmol) and acetylsalicyloyl chloride (6.31 g, 31.74 mmol). The reaction was returned to room temperature and allowed to stir for 6 hours before washing with water (2×50 ml), HCl (1 M, 2×50 ml), saturated aqueous NaHCO$_3$ (2×50 ml) and brine (100 ml). The organic phase was dried with Na$_2$SO$_4$ and solvent removed in vacuo to yield product as oil. This was crystallised from ethanol to yield 5.42 g of product as white crystals. (58.05%): m.pt. 82-84° C. IR$_{Vmax}$ (KBr): 1757.6 and 1733.4 (C=O), 1651.8 (NO$_2$), 1261.4 (C(O)OR, aromatic), 915.5 (ONO$_2$) cm$^{-1}$. HRMS: Requires: 376.0645 (M$^+$+23), Found: 376.0640 (M$^+$+23). $^1$H NMR δ (CDCl$_3$): 2.37 (3H, s, OCOCH$_3$), 3.93 (1H, dd, J 6.0, 11.5 and 6.0 Hz, IS6a-H), 4.09 (3H, m, IS1H [αβ] and IS6H [β]), 4.58 (1H, d, J 4.5 Hz, IS3-H), 5.03 (1H, t, J 5.0 and 5.5 Hz, IS4-H), 5.38 (1H, m, IS5-H), 5.45 (1H, d, J 3.0 Hz, IS2-H), 7.12 (1H, d, J 8.0 Hz, Ar—H), 7.33 (1H, t, J 7.5 and 8.0 Hz, Ar—H), 7.60, (1H, t, J 7.5 and 8.0 Hz, Ar—H), 8.01 (1H, d, J 7.5 Hz, Ar—H). $^{13}$C NMR ppm (CDCl$_3$): 20.40 (OCOCH$_3$), 68.88 and 72.84 (ISC-1 and ISC-6), 77.50 (ISC-5), 80.83 (ISC-4), 81.08 (ISC-2), 122.19 (ArC-1), 123.41, 125.61, 131.37, 133.92 (aromatic methine), 150.24 (ArC-2), 163.09 (ArOCO(Me)), 169.17 (Ar$\underline{C}$(O)OR).

Experimental Method: Hydrolysis Studies Using Plasma/Enzyme Solutions

Pooled plasma/serum solutions (4 ml) were prepared to the correct strength by dilution of plasma with phosphate buffer pH 7.4 (e.g. for a 10% solution 0.4 ml of plasma/serum was added to 3.6 ml of phosphate buffer pH 7.4). Following equilibration of the plasma/serum sample at 37±0.5° C. 100 µl of a stock solution of test compound in acetonitrile (1×10$^{-4}$ M) was added and 250 µl aliquots were removed at specified time intervals. Samples were transferred to 1.5 ml Eppendorf tubes containing 500 µl of a 2% w/v solution of nSO$_4$.7H$_2$O (water:acetonitrile, 1:1). Tubes were vortexed for 2 minutes, then centrifuged at 10,000 rpm for 3 minutes at room temperature. Supernatant was aspirated off and analysed by HPLC. The concentration of test compound and metabolites were determined with reference to calibration curves run on that day in the same concentration range and under the same experimental conditions. In order to mimic conditions during the first passage of the drugs after intestinal absorption selected compounds were incubated in phosphate buffer at 37° C. in the presence of microsomes from human liver (HLM) and intestinal epithelium (HIM). The metabolic fate of the esters under these conditions was also determined by RPHPLC by measuring the concentration of drug and metabolites in the medium as a function of time. The identity of participating enzymes was confirmed by using purified enzyme in the case of plasma (BuChE) and by repeating the hydrolysis experiments in the presence of esterase specific inhibitors—isoOMPA for BuChE and BNPP for carboxylesterase. The BuChE activity of plasma and microsomal samples was determined using the Ellman assay (Ellman et al., 1964).

HPLC Procedure

High performance liquid chromatography was performed using a system consisting of a Waters 600 pump and controller, Waters 717 autosampler and a Waters 2996 photodiode array detector controlled by Empower software. A Hichrom Nucleosil C18 column (4.0×250 mm) was used. Mobile phase was filtered prior to use and sparged with helium throughout assays. The final gradient method used was as follows:

TABLE 1

Gradient method used for hydrolysis assays

| Time (min) | Flow rate (ml/min) | % Buffer (pH 2.5) | % acetonitrile |
|---|---|---|---|
| 0 | 1 | 80 | 20 |
| 10 | 1 | 20 | 80 |
| 15 | 1 | 60 | 40 |

TABLE 1-continued

Gradient method used for hydrolysis assays

| Time (min) | Flow rate (ml/min) | % Buffer (pH 2.5) | % acetonitrile |
|---|---|---|---|
| 17 | 1 | 80 | 20 |
| 20 | 1 | 80 | 20 |

The method was validated for linearity, precision and for the metabolites for LOQ and LOD. Developing a method that gave good separation of aspirin and salicylic acid was a lengthy task as the initial choice of a spherisorb ODS C18 column with buffer pH 3.19 gave extreme tailing and poor separation (buffer with a pH of 3.19 was chosen as it's close to their pKa's—aspirin is 3.5 and salicylic acid is 2.97[2]). This was eventually solved by using the hichrom nucleosil column and buffer pH 2.5. As aspirin is a weak acid with a pKa of 3.5 reducing the buffer pH below its pKa decreases retention as the compound becomes more hydrophobic. The nucleosil column gave excellent peak shape and resolution of the two compounds. Initially monohydrate salts were used which produced a large buffer peak at 18 mins. Using dihydrate salts eliminated the peak. Although nearing the end of this work some large buffer peaks began to appear again.

There are also methods for measuring platelet aggregation inhibition, $TXB_2$, platelet GP2B3A expression, MDA and corresponding data that demonstrate that the key compounds have aspirin-like activity.

Whole Blood Aggregation Studies

A 500 µl aliquot of blood was mixed with 500 µl of physiological saline and allowed to incubate at 37° C. for 10 mins in the incubation well of a Chrono-Log Whole Blood Aggregometer model 591/592. The sample was then transferred to the assay well, baseline was established and appropriate volume of reagent as above was added. Aggregation was monitored over 6 mins with impedance output recorded on a chart recorder. When testing inhibitors whole blood was pre-incubated with appropriate concentrations of inhibitor in DMSO at 37° C. for a specified length of time before adding the stimulant (10 mins with stirring). Three different aggregating agents, AA (0.5 mM), ADP (10 µM) and Collagen (5 µg/ml) were used. Where no aggregation response was observed in the presence of an inhibitor a control experiment was performed with no inhibitor present. DMSO in high concentrations (above 0.25%) can induce a concentration dependent change in platelet cytoplasmic ionised calcium. Before each experiment a control was run using PRP to obtain normal aggregating responses. A sample was also incubated for 10 min at 37° C. with 10 µl DMSO to ensure it was having no inhibitory effect on the aggregation response. Two metabolites of ISAS, salicylic acid and isosorbide were examined to determine if they had inhibitory effect on platelets. In this model ISAS exhibited significantly greater potency than aspirin or ISDA in the inhibition of platelet aggregation to all of the aggregatory stimuli.

Platelet Rich Plasma Platelet Aggregation

Blood was collected from healthy volunteers who had not taken any drugs known to affect platelet function for at least 14 days prior to the study. Platelet rich plasma (PRP) and washed platelet suspensions ($2.5\times10^8$ platelets/ml) were prepared from blood as previously described.

Platelet aggregation was measured by light aggregometry as previously described. Briefly, PRP and washed platelet samples ($2.5\times10^8$/ml) were placed in a whole blood ionized calcium lumi-aggregometer (Chronolog Corp., Havertown, Pa., U.S.A), and (BIO/DATA CORPORATION) and incubated for 10 min at 37° C., with stirring at 900 r.p.m., prior to the addition of aggregating agents. Aggregation was initiated by the addition of agonists, and monitored by Aggro-Link software for at least 6 min. For experiments using inhibitors, aggregation was initiated after 10 min preincubation with these compounds To study the aggregatory potency of ADP, the concentration-response (0.3-10 uM) curves were generated. Collagen at different concentrations (3-5 ug/ml) was also used to induce platelet aggregation. The submaximal concentrations of agonists, i.e. the concentrations that gave approximately 95% of the maximal aggregation were used to study the effects of inhibitors of aggregation. Results were expressed in percent changes in maximal light transmission, with 100% representing light transmission of platelet medium alone.

Inhibition of TXB2 Synthesis.

Aspirin inhibits platelet aggregation by attenuating cyclooxygenase mediated synthesis of PGH2, which is converted in cells to the powerful aggregator $TXA_2$ by thromboxane synthase. $TXA_2$ is highly evanescent and unsuitable for direct measurement but its metabolite $TXB_2$ is generally believed to provide a useful index of the parent. Aspirin treatment of tissue in vivo or in vitro is reflected in a depression of $TXB_2$. In order to compare the compounds of the invention with aspirin in this regard untreated whole blood was allowed to clot in the presence of aspirin or the test compounds over the course of 1 hour at 37° C. The samples were then centrifuged. Serum was collected and $TXB_2$ was measured using enzyme linked immunosorbent assay (ELISA) kits obtained from Cayman Chemicals. The experiments were performed with aspirin in descending concentration from values that gave complete inhibition of $TXB_2$ synthesis. In these assays ISAS was significantly more potent than aspirin as reflected in a lower $IC_{50}$.

Flow Cytometry

In order to analyze receptor expression on the surface of individual platelets and to minimize platelet activation caused by sample preparation procedures, no stirring or vortexing steps were used. The abundance of activated GPIIb/IIIa and P-selectin on the surface of platelets in the presence and absence of inhibitors was measured by flow cytometry. Platelet samples were first activated with agonists either collagen or ADP. When platelet aggregation reached 50% maximal light transmission the reaction was terminated by 10-fold dilution with physiologic saline. Resting platelets were used as control. In most of the experiments, platelets were preincubated with inhibitors for 10 min prior to the addition of agonists. Platelet samples were then incubated in the dark without stirring for 5 min at room temperature in the presence of saturating concentrations (10 µg/ml) of P-selectin (CD62P-APC). The activated GPIIb/IIIa platelet receptors were measured using PAC-1 monoclonal antibody at the same concentration as above. PAC-1 specifically recognizes an epitope on the high-affinity GPIIb/IIIa complex of activated platelets at or near the platelet[5]. Following incubation, samples were diluted in FACS Flow fluid and analyzed within 5 min using a BD FACSArray (BD Biosciences, Oxford, UK). Flow cytometry was performed on single stained platelet samples as described before[3]. The instrument was set up to measure the size (forward scatter), granularity (side scatter) and cell fluorescence. A two-dimensional analysis gate of forward and side scatter was drawn in order to include single platelets and exclude platelet aggregates and microparticles. Antibody binding was measured by analyzing individual platelets for fluorescence. The mean fluorescence intensity was determined after correction for cell autofluorescence. For each sample, the fluorescence was analyzed using a logarithmic scale. Fluorescence histograms were obtained for 10,000 individual events. Data were analyzed using Cytometer RXP software and expressed as a percentage of control fluorescence in arbitrary units.

Preparation of Biological Samples for Hydrolysis and Aspirin-Release Measurement Human blood samples were collected by venipuncture into Li-Heparin Sarstedt Monovette tubes (9 ml). Plasma samples were obtained by centrifugation of blood at 10,000 rpm for five minutes and were frozen in aliquots until required for testing. Pooled human liver microsomes (HLM) were diluted to 5 ml with phosphate buffer pH 7.4 (0.1M) giving a stock solution of 2 mg/ml. Aliquots were frozen until required for testing. Pooled human intestinal microsomes (HIM) were diluted to 5 ml with phosphate buffer pH 7.4 (0.1M) giving a stock solution of 80 μg/ml. Aliquots were frozen until required for testing.

Cholinesterase Activity

Butyrylcholinesterase (BChE) activity in HLM and HIM was determined spectrophotometrically (405 nm) at 37° C. by the Ellman method (Ellman et al., 1964). Butyrylthiocholine iodide (BTCI) (0.5 mM) was used as the substrate. The reaction took place in a 96-well plate with a final volume of 250 μl. Initially phosphate buffer pH 8.0 (0.1M) and microsomes were mixed and incubated for 30 mins. DTNB (0.3 mM) and BTCI were added and the reaction was measured. The assay was also performed using sonication bursts (4×5 sec) on the microsomes and placing on ice for 1 min in between. This ensures that the microsomes are open to penetration by reagents[5]. The activity was calculated according to Eqn 1:

$$\text{Enzyme activity } (\mu\text{mol/L/min}) = \frac{\text{Sample-Blank}}{10.6_{(abs\ coefficient)}} \quad \text{Eqn 1}$$

Table 2 shows the compounds with numbering and the amount of aspirin as a percentage of the initial ester concentration in moles measured at peak aspirin production following addition of candidate esters to buffered human plasma at 37° C. at pH 7.4 (phosphate buffer).

TABLE 2

| Compound | Half-life and molar % aspirin released in 10% human plasma | | Half-life and molar % aspirin released in 50% human plasma | |
|---|---|---|---|---|
| 2-Methyl benzoate, R = (1) | 2.17 min | 46.02% | 0.83 min | 58.53% |
| Salicylate, R = (ISAS) 2 | 4.90 min | 72.23% | 1.14 min | 85.56% |
| 3-Methyl benzoate, R = (3) | 9.72 min | 38.54% | 1.21 (min) | 53.66% |

TABLE 2-continued

Compound: [structure of 2-acetoxybenzoate ester of isosorbide with OR group]

| | Half-life and molar % aspirin released in 10% human plasma | | Half-life and molar % aspirin released in 50% human plasma | |
|---|---|---|---|---|
| Acetate, R = [COCH₃] 4 | 3.63 min | 1.17% | 0.57 (min) | 1.19% |
| Pentanoate, R = [CO-butyl] 5 | 3.76 min | 6.82% | 0.66 (min) | 6.71% |
| Benzoate, R = [CO-phenyl] 6 | 3.32 min | 18.93% | 0.64 (min) | 28.51% |
| Nicotinate, R = [CO-3-pyridyl] 7 | 1.29 min | 27.58% | 0.37 (min) | 17.92% |
| iso-Nicotinate, R = [CO-4-pyridyl] 8 | 3.68 min | 18.76% | 0.33 (min) | 27.62% |
| Benzoyloxy-benzoate, R = [CO-2-(benzyloxy)phenyl] 9 | 20.63 min | 12.87% | 4.27 (min) | 18.89% |

TABLE 2-continued

| Compound | Half-life and molar % aspirin released in 10% human plasma | | Half-life and molar % aspirin released in 50% human plasma | |
|---|---|---|---|---|
| 2-Aminobenzoate, R = (structure) 10 | 50.22 min | 2.82% | 1.55 (min) | 4.68% |
| 2-Methoxy benzoate, R = (structure) 11 | 3.59 min | 5.16% | 0.99 (min) | 7.08% |
| 2-Methoxybenzoate, R = (structure) 12 | 3.28 min | 18.91% | 0.85 (min) | 17.00% |
| 4-Methoxy benzoate, R = (structure) 13 | 3.17 min | 2.53% | 1.10 (min) | 3.75% |
| 4-Methoxy benzoate, R = (structure) 14 | 6.23 min | 15.85% | 2.16 (min) | 14.49% |

TABLE 2-continued

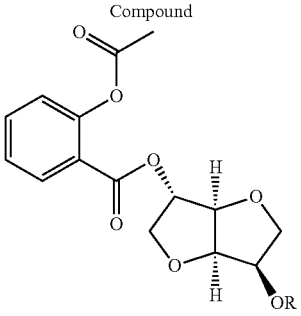

| Compound | Half-life and molar % aspirin released in 10% human plasma | | Half-life and molar % aspirin released in 50% human plasma | |
|---|---|---|---|---|
| 4-Nitrobenzoate, R = 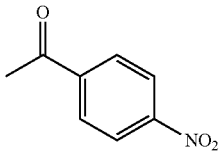 15 | 2.86 min | 18.46% | 1.37 (min) | 22.25% |
| Aspirinate, R = 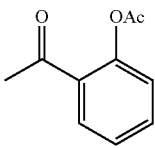 (ISDA) 16 | 4.43 min | 51.0% | 0.68 (min) | 60.47% |
| Unsubstituted, R = H (Isosorbide-2-aspirinate) 17 | 4.08 min | 2.95% | Not tested | Not tested |
| -(3-(2-bromo-acetoxy))-benzoate, R = 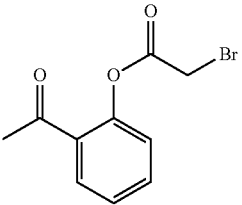 18 | 1.85 min | 74.2% | n/a | n/a |
| Cyclopropanoate, R = 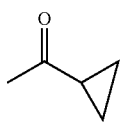 19 | 1.9 min | <2% | n/a | n/a |
| p-cyanobenzoate, R = 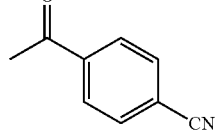 20 | Not tested | Not tested | 4.3 min | <1% |

TABLE 2-continued

| Compound | Half-life and molar % aspirin released in 10% human plasma | | Half-life and molar % aspirin released in 50% human plasma | |
|---|---|---|---|---|
| p-phenylbenzoate, R = (21) | Not tested | Not tested | >1 hour | <1% |
| 6-chloronicitinoate, R = (22) | Not tested | Not tested | 1.4 min | 45% |
| 2-chloro-6-methylnicitinoate, R = (23) | Not tested | Not tested | 2.7 min | 48% |
| 3,5 diethoxybenzoate, R = (24) | Not tested | Not tested | 3.1 min | <1% |
| 3-methylisoxazole-4-oate, R = (25) | Not tested | Not tested | <1 min | 72% |

TABLE 2-continued

| Compound | | Half-life and molar % aspirin released in 10% human plasma | | Half-life and molar % aspirin released in 50% human plasma | |
|---|---|---|---|---|---|
| 4-methyl-1,2,3-thiadiazole-5-oate, R = 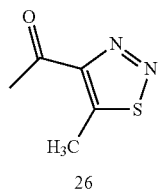 26 | | Not tested | Not tested | <1 min | 68% |
| NBOC nipecotoate, R = 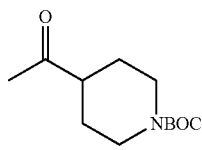 27 | | Not tested | Not tested | 4.1 min | <1% |
| 3-acetamidobenzoate, R = 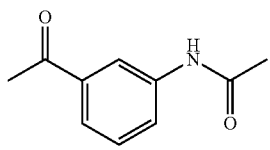 28 | | Not tested | Not tested | 1.3 min | 21% |
| p-benzyloxybenzoate, R = 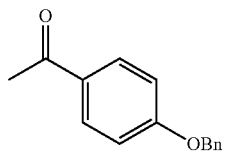 29 | | Not tested | Not tested | >5 min | <1% |
| R = m-benzyloxybenzoate, 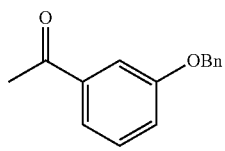 30 | | Not tested | Not tested | 2.5 min | <1% |

TABLE 2-continued

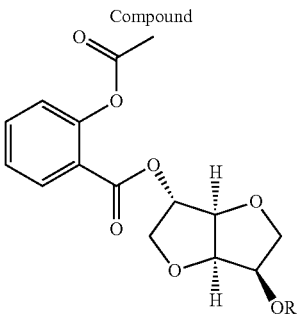

| Compound | Half-life and molar % aspirin released in 10% human plasma | | Half-life and molar % aspirin released in 50% human plasma | |
|---|---|---|---|---|
| (2-Nitroxymethyl)-benzoate, R = 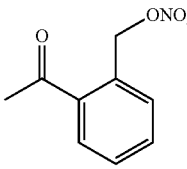 31 | Not tested | Not tested | 3.2 min | 81% |
| (3-Nitroxymethyl)-benzoate, R = 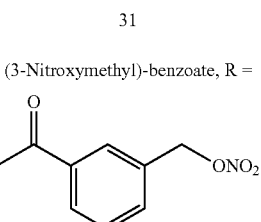 32 | Not tested | Not tested | 2.7 min | 78% |
| (4-Nitroxymethyl)-benzoate, R = 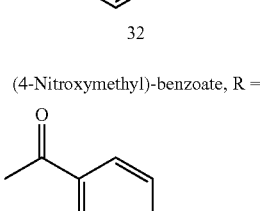 33 | 5.99 min | 2% | Not tested | Not tested |
| (Nitrooxy)-acetate, R = 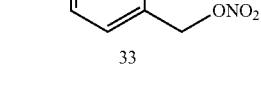 34 | 3.61 min | <0.5% | Not tested | Not tested |

Results of Tests in Plasma from Test Animals

Qualitative hydrolysis screening of Is-2-aspirinate-5-salicylate 2 (0.1 mM) was studied using guinea pig, hamster, rabbit and monkey plasma. The purpose of this test was to determine a suitable species for biological testing and preclinical development. The results were also expected to confirm the role of the human enzymes already identified because these are variously distributed in laboratory animals.

TABLE 3

Hydrolysis of Is-2-aspirinate-5-salicylate using various species

| Pro-drug conc (mM) | Plasma source | Aspirin | Drug disappearance time (min) |
|---|---|---|---|
| 0.1 | Guinea Pig | (v small amounts) | present after 1 hr |
| 0.1 | Rabbit | (v small amounts) | 10 |
| 0.1 | Hamster | (large amounts) | 20 |
| 0.1 | Monkey | (large amounts) | 5 |

Once a gradient method was successfully developed hydrolysis of 2 in 50% rabbit plasma was run as the rabbit is a potential model for platelet aggregation studies. The Ellman assay revealed BChE activity at 1.1 μmol/L/min. The results suggest that hamster and monkey would make suitable candidates for preclinical testing. Since plasma from these species has similar levels of BuChE to humans the role of that enzyme in human metabolism is also supported.

Figure 13:
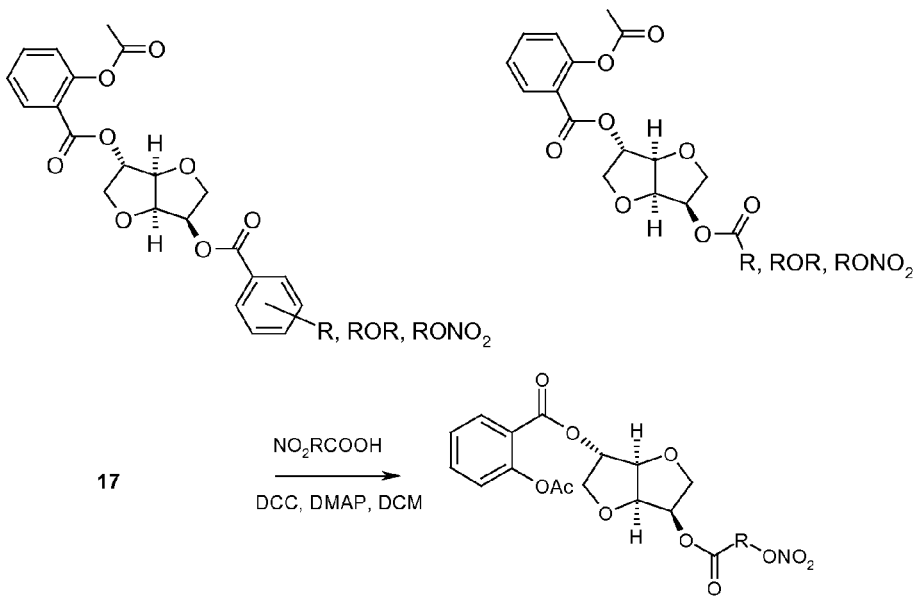
FIG. 13: Direct synthesis of nitrate-substituted 5-esters
Figure 14:
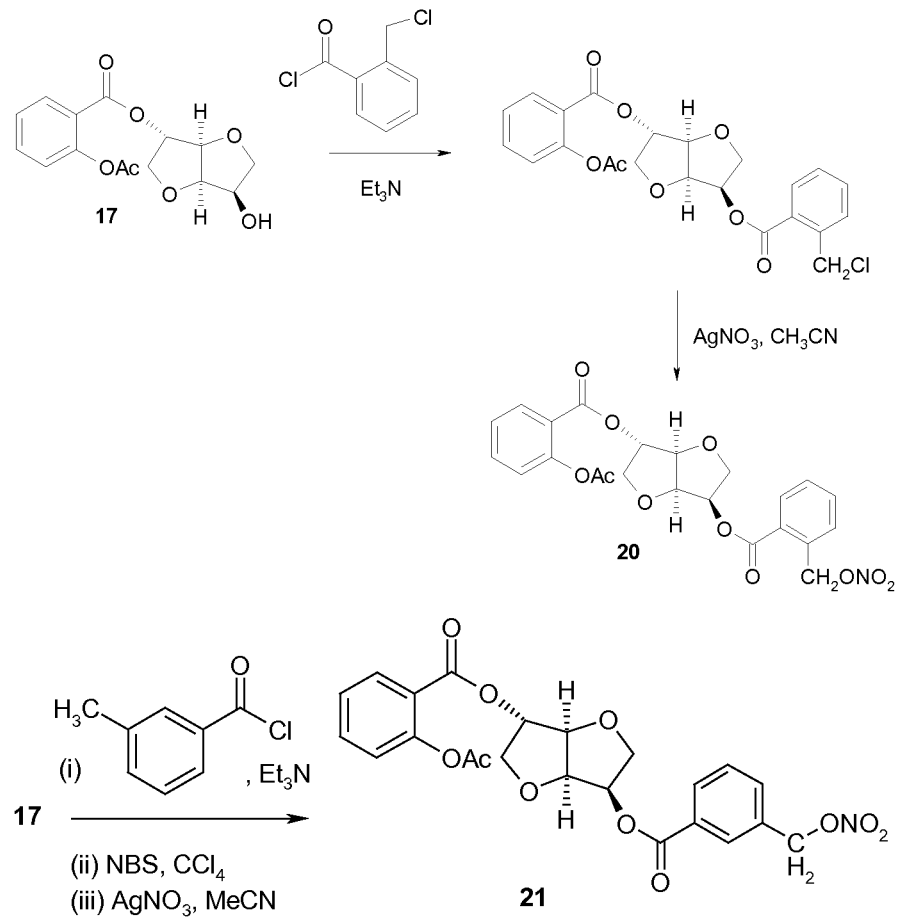
FIG. 14: Synthesis of 3-nitroxybenzoate ester of isosorbide-2-aspirinate by esterification with a chloromethyl benzoate and exchange of halide with silver nitrate.
Figure 15:
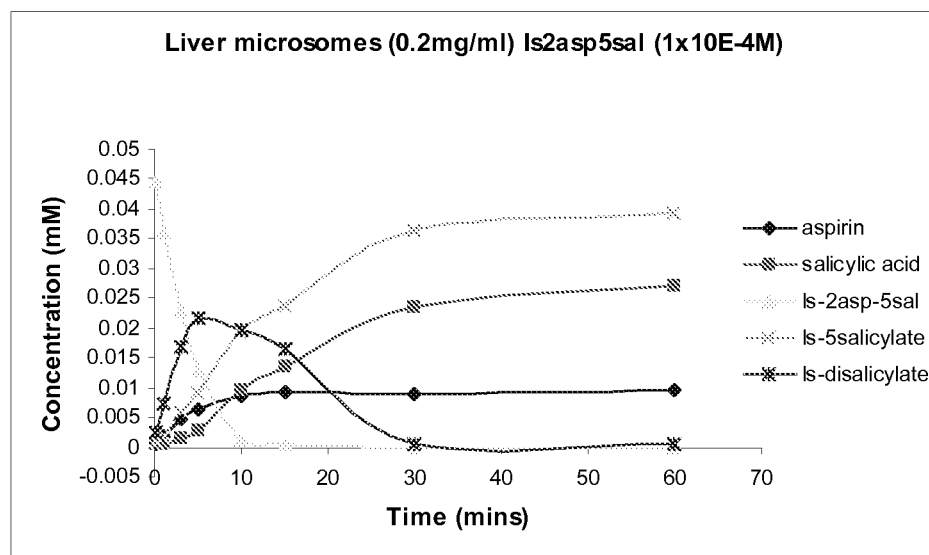
FIG. 15: Is-2-aspirinate-5-salicylate (ISAS, 2) in HLM. 9.4 µM aspirin produced.
Figure 16:
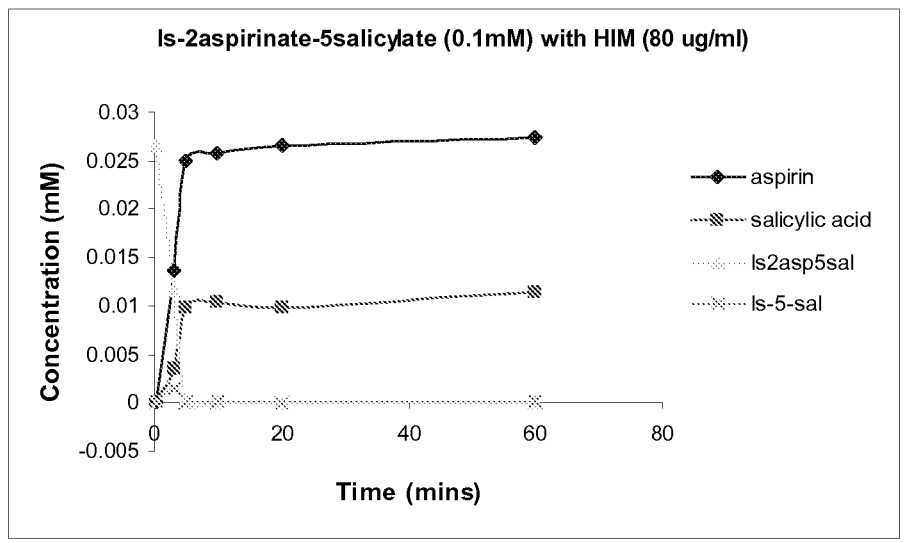
FIG. 16: Is-2-aspirinate-5-salicylate (ISAS, 2) ($1.04 \times 10^{-4}$ M) in HIM. 27 µM of aspirin produced.
Figure 17:
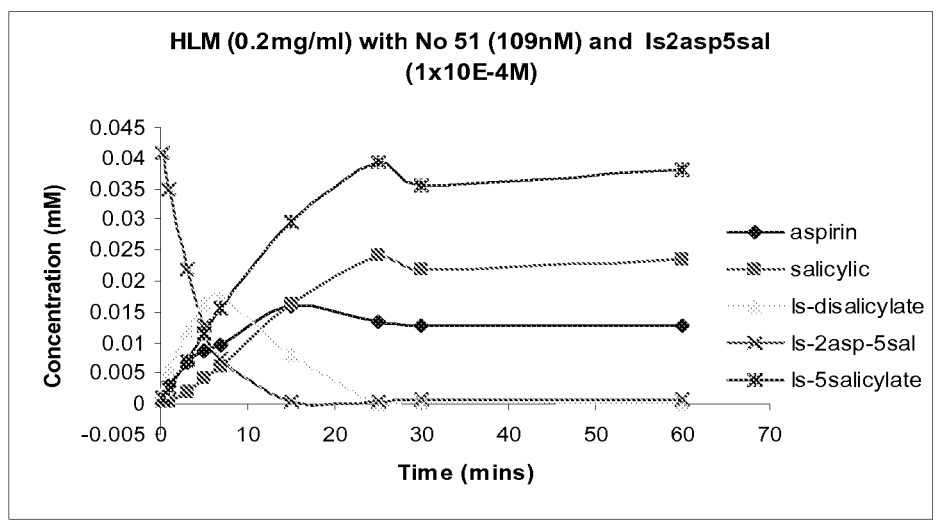
FIG. 17: HLM incubated for five mins with a potent BChE inhibitor before adding Is-2-aspirinate-5-salicylate (ISAS, 2). 16 µM aspirin produced.

Hydrolysis Results for Is-2-aspirinate-5-salicylate, ISAS (2) in the Presence of Intestinal or Liver Microsomes Hydrolysis studies in human blood plasma had indicated that ISAS (2) is a successful aspirin pro-drug. This work aimed to broaden the analysis to include liver and intestinal microsomal preparations in order to assess how much aspirin release would occur in other tissues during the absorption phase principally at the gastric epithelium and later in the liver. When the drug was incubated in the presence of Human Liver Microsomes and Human Intestinal Microsomes 9 µM and 56 µM of aspirin were produced (FIG. 13) and (FIG. 14) respectively. This raised the question as to whether this was due to the presence of BChE or to some other enzyme(s) because whereas human blood contains only butyrylcholinesterase the liver and intestinal epithelium also contain carboxylesterases (CE)—mainly CE-1 in the liver and CE-2 in the intestine. The microsomal preparations was therefore pre-incubated with iso-OMPA an established BChE inhibitor prior to addition of the pro-drug so as to allow sufficient time to inhibit any BChE that might have been present in the microsomal preparations. Hydrolysis assays were then carried out as previously described to see what effect if any there was on aspirin production. The use of the specific BChE inhibitor did not diminish aspirin production suggesting that some other enzyme is involved. The Ellman assay was performed on both microsomal preparations so as to determine what levels of BChE are present, if any. Only minimal amounts were found (Table 3.1) and could not be attributed to the high levels of aspirin production.

TABLE 4

BChE activity results for HLM and HIM

| HLM (mg/ml) | Activity (µmol/L/ min) No sonication | Activity (µmol/L/min) With sonication | HIM (µg/ml) | Activity (µmol/ L/min) No sonication | Activity (µmol/ L/min) With sonication |
|---|---|---|---|---|---|
| 0.04 | 0 | — | 16 | 0.16 | 0.18 |
| 0.08 | 0 | — | 32 | 0.33 | — |
| 0.2 | — | 0.93 | | | |
| 0.4 | 2.86 | 1.68 | | | |
| 0.8 | 4.93 | 3.03 | | | |

Blank female plasma=14.98 µmol/L/min. Plasma contains approx 5 mg/L BChE[5] therefore this is the equivalent of 0.0125 µg/ml BChE.

Figure 18:
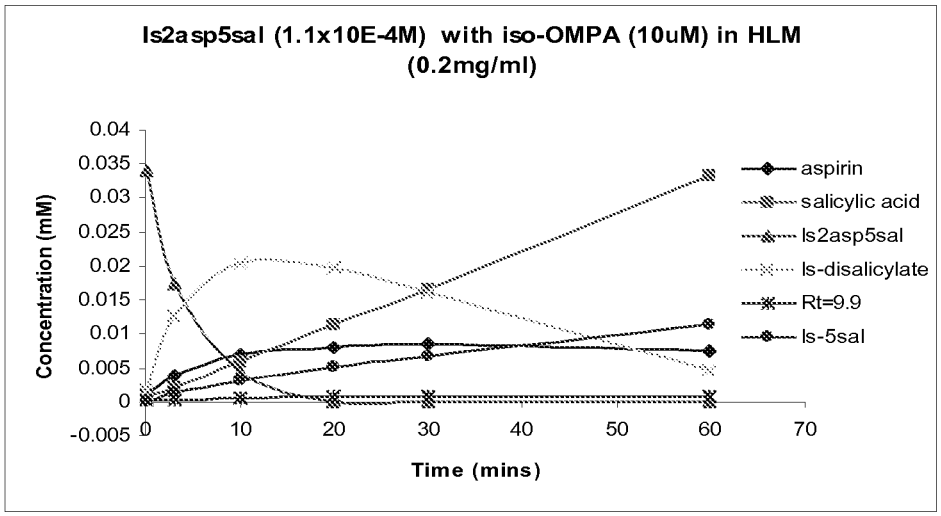
FIG. 18: Is-2-aspirinate-5-salicylate (ISAS, 2) ($1.1 \times 10^{-4}$ M) in HLM with iso-OMPA (10 µM). 8.5 µM of aspirin produced.
Figure 19:
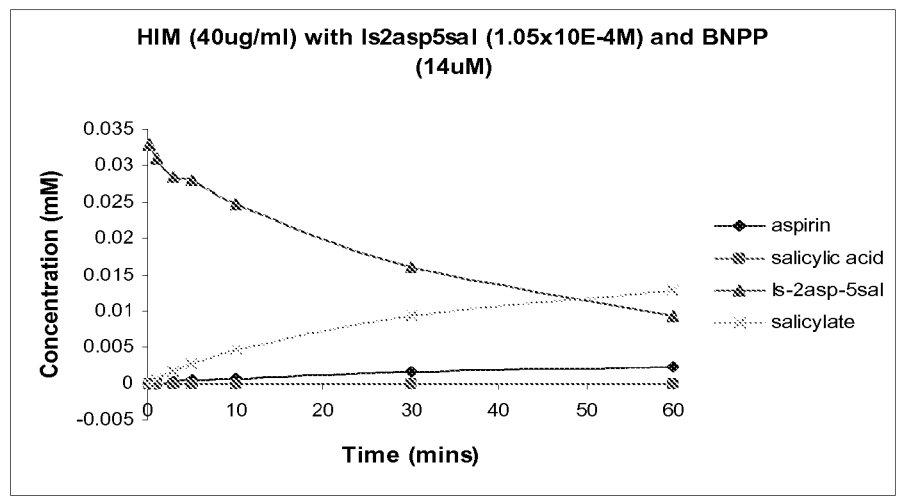
FIG. 19: Is-2-aspirinate-5-salicylate (ISAS, 2) ($1.04 \times 10^{-4}$ M) in HIM with BNPP (14 µM).
Figure 20:
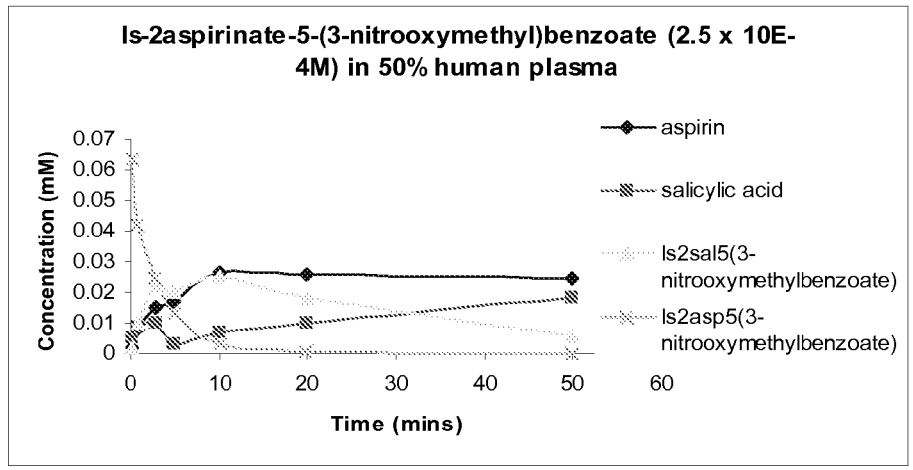
FIG. 20: Is-2-aspirinate-5-(3-nitrooxy-methyl)benzoate (21) ($2.5 \times 10^{-4}$ M) in 50% human plasma. 26 µM of aspirin produced.
Figure 21:
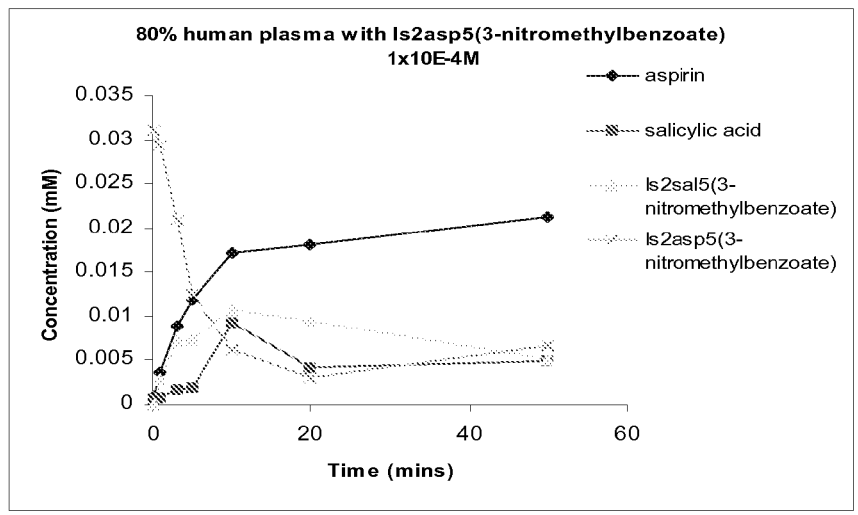
FIG. 21: Is-2-aspirinate-5-(3-nitrooxy-methyl)benzoate (21) ($1 \times 10^{-4}$ M) in 80% human plasma. 21 µM of aspirin produced.
Figure 22:
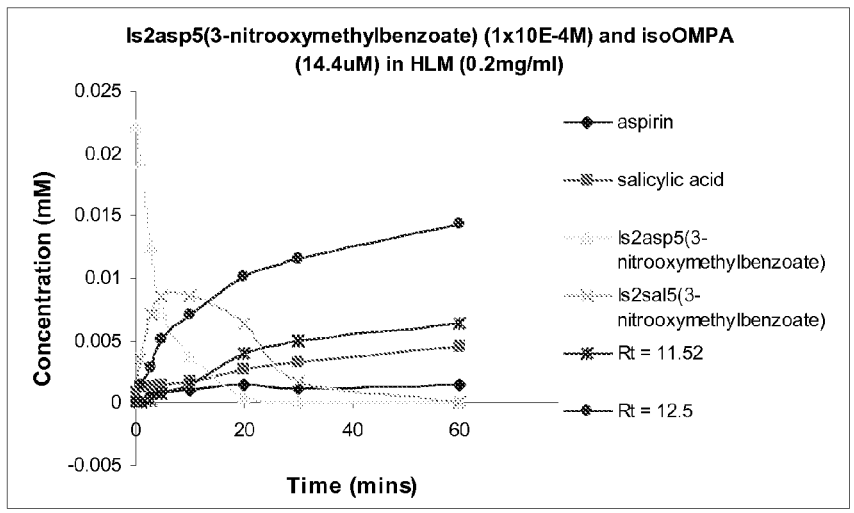
FIG. 22: Is-2-aspirinate-5-(3-nitrooxy-methyl)benzoate (21) ($1 \times 10^{-4}$ M) in HLM with iso-OMPA (14.4 µM). 1.4 µM of aspirin produced.
Figure 23:
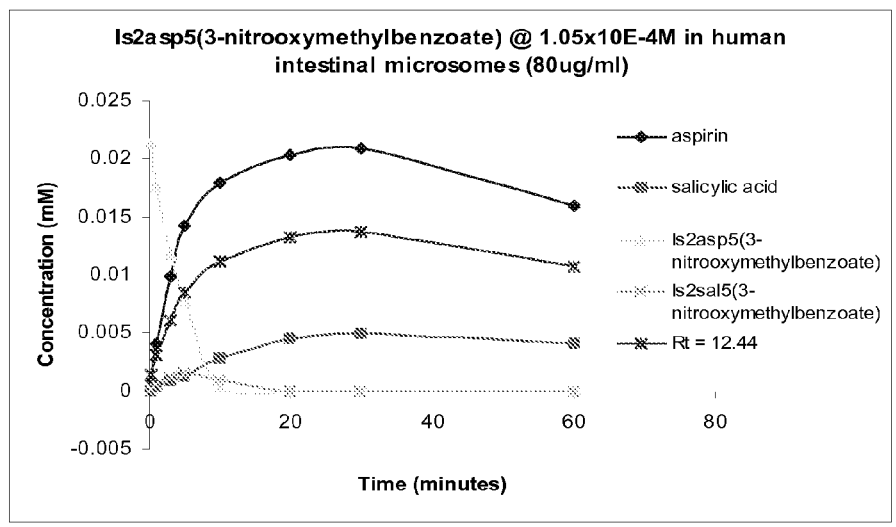
FIG. 23: Is-2-aspirinate-5-(3-nitrooxy-methyl)benzoate (21) ($1.05 \times 10^{-4}$ M) in HIM. 20 µM of aspirin produced.
Figure 24:
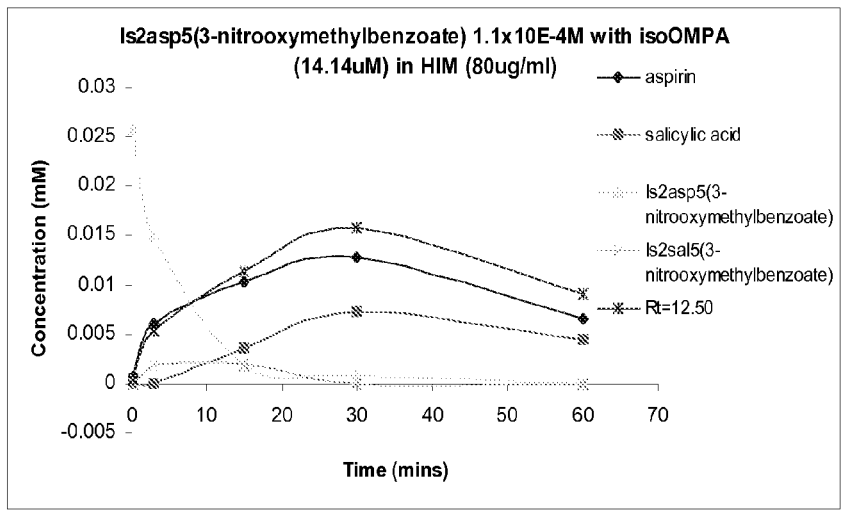
FIG. 24: Is-2-aspirinate-5-(3-nitrooxy-methyl)benzoate (21) ($1.1 \times 10^{-4}$ M) in HIM with iso-OMPA (14 µM). 12.7 µM of aspirin produced.
Figure 25:
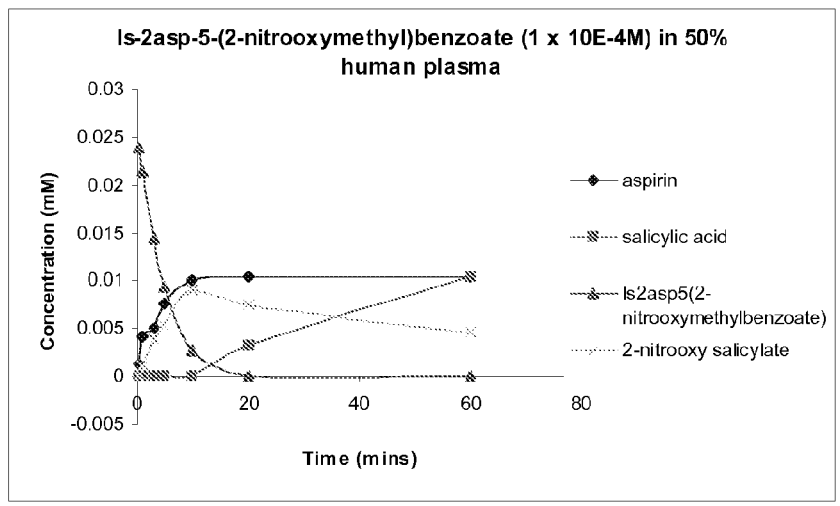
FIG. 25: Is-2-aspirinate-5-(2-nitrooxy-methyl)benzoate (20) ($1 \times 10^{-4}$ M) in 50% human plasma. 10.3 µM aspirin produced.
Figure 26:
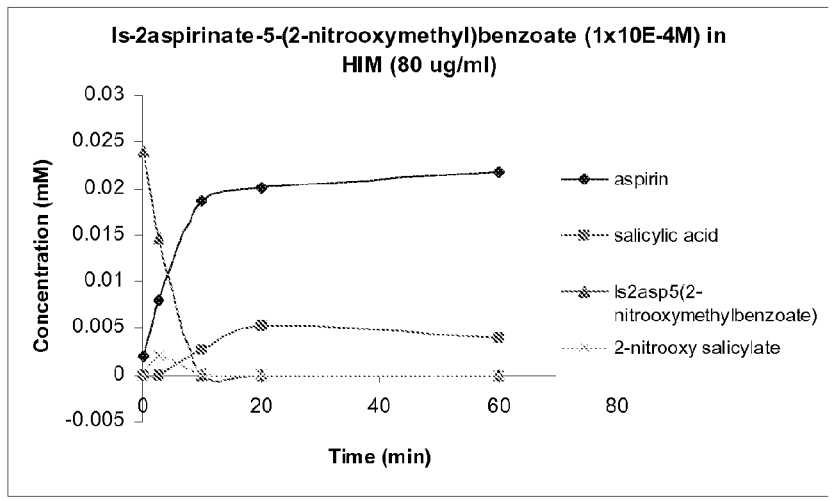
FIG. 26: Is-2-aspirinate-5-(2-nitrooxy-methyl)benzoate (20) ($1 \times 10^{-4}$ M) in HIM. 21.7 µM aspirin produced.
Figure 27:
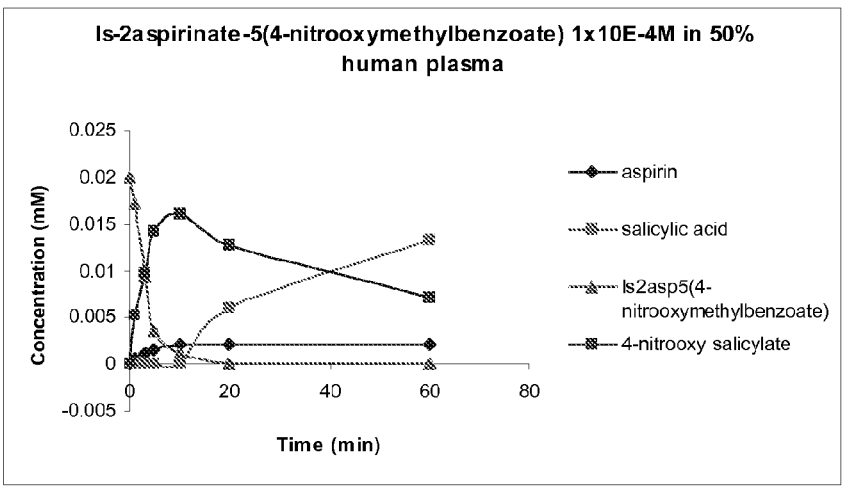
FIG. 27: Is-2-aspirinate-5-(4-nitrooxy-methyl)benzoate (22) ($1 \times 10^{-4}$ M) in 50% human plasma. 2 µM aspirin produced.
Figure 28:
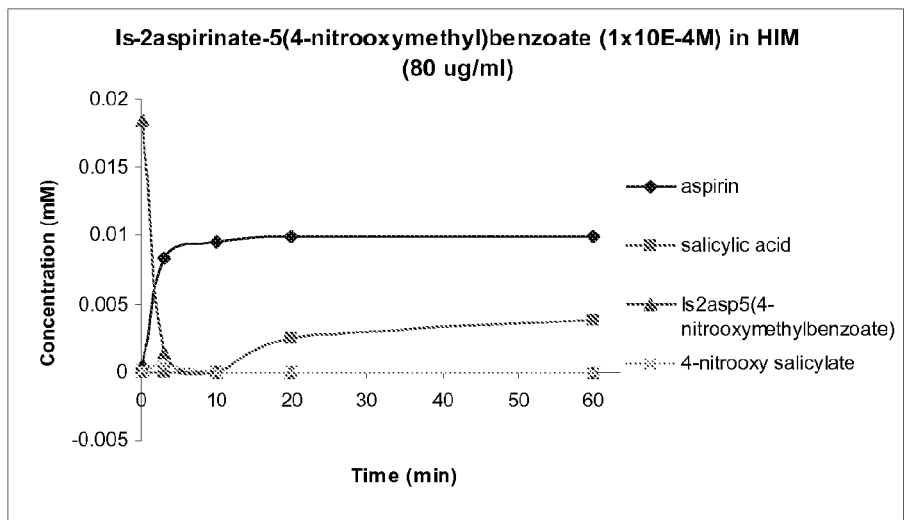
FIG. 28: Is-2-aspirinate-5-(4-nitrooxy-methyl)benzoate (22) ($1 \times 10^{-4}$ M) in HIM. 9.97 µM aspirin produced.
Figure 29:
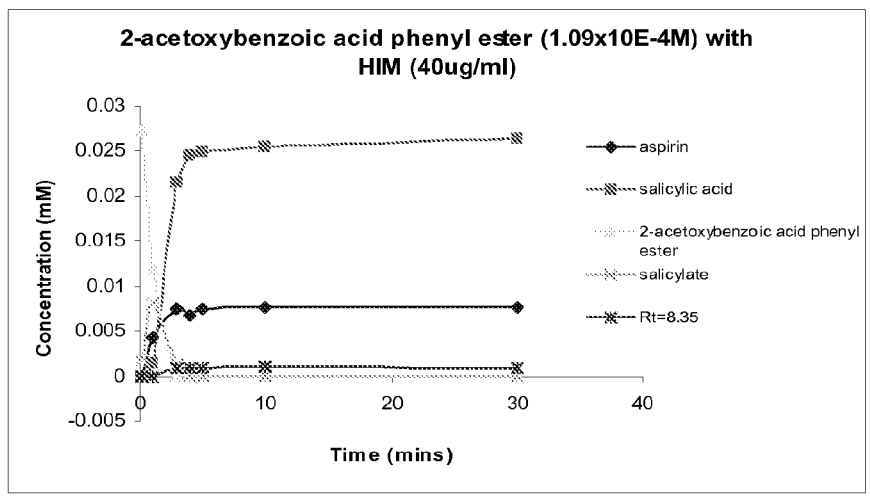
FIG. 29: 2-acetoxybenzoic acid phenyl ester (phenol ester of aspirin) ($1.09 \times 10^{-4}$ M) in HIM (40 µg/ml). 7.7 µM aspirin produced.
Figure 30:
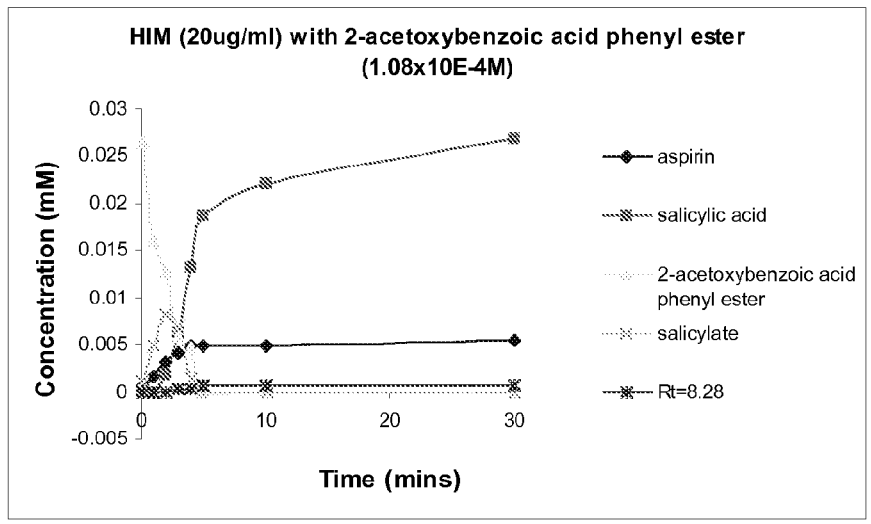
FIG. 30: 2-acetoxybenzoic acid phenyl ester ($1.09 \times 10^{-4}$ M) in HIM (20 µg/ml). 5.3 µM aspirin produced.
Figure 31:
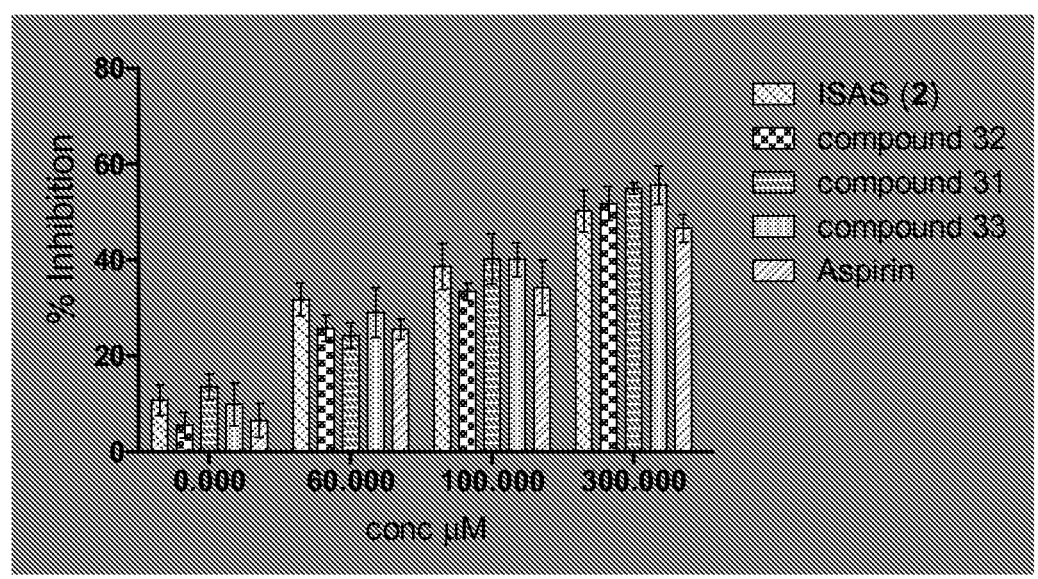
FIG. 31: Inhibition of platelet aggregation in response to ADP in vitro by the five test compounds at three different concentrations. The zero concentration is inhibition by the vehicle, DMSO.
Figure 32:
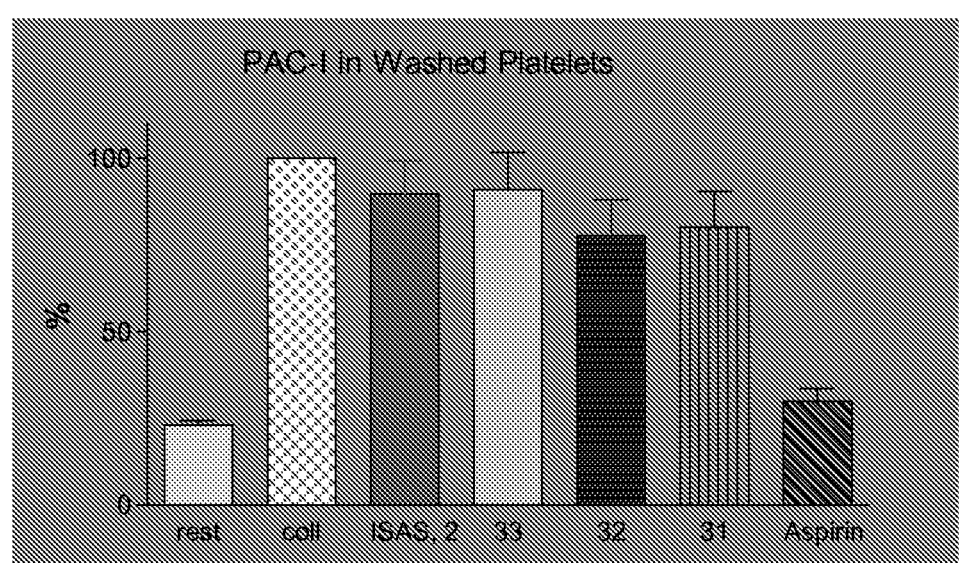
FIG. 32: PAC-1 expression in response to collagen in washed platelet treated with test compounds 2, 31-33, aspirin. This figure shows the percent PAC-1 glycoprotein expression in washed platelets. There is little esterase in this preparation so the data illustrates that esterase activation of the prodrugs of the invention is required before inhibition of platelet function in vitro.
Figure 33:
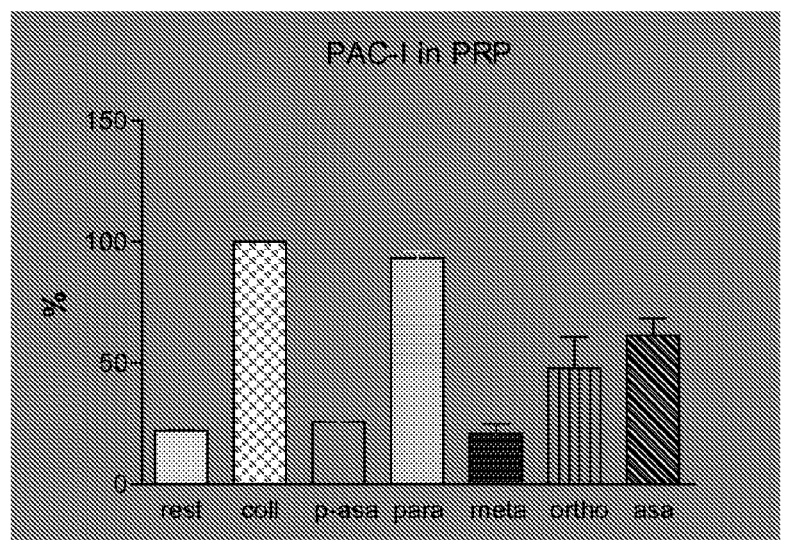
FIG. 33: PAC-1 expression in response to collagen in platelet rich plasma with test compounds 2, 31-33, aspirin. This figure shows the extent of glycoprotein expression in platelet rich plasma. Glycoprotein expression is required for cross linking of platelets in full aggregation and the data shows that the compounds of the invention are more potent than aspirin in suppressing this expression in plasma preparation.
Figure 34:
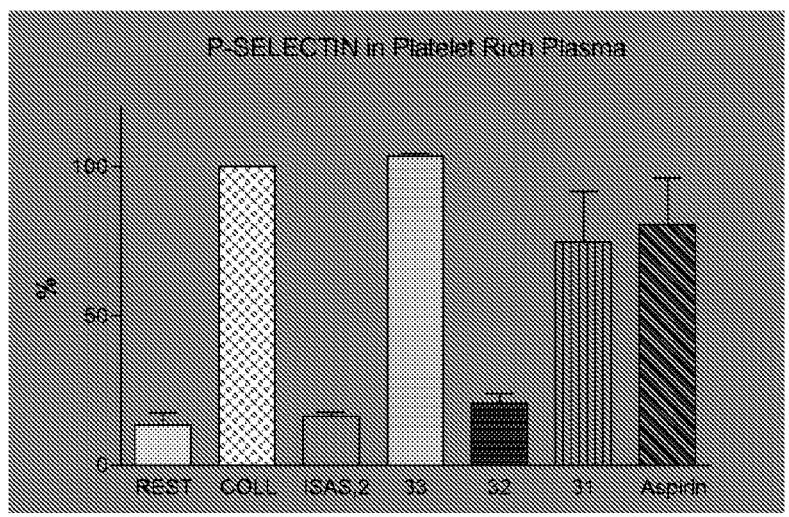
FIG. 34: P-selectin expression to collagen in platelet rich plasma with test compounds 2, 31-33, aspirin. P-selectin is another glycoprotein whose expression correlates with platelet activation. The compounds of the invention are far more potent than aspirin at inhibiting platelet activation in plasma preparations.
Figure 35:
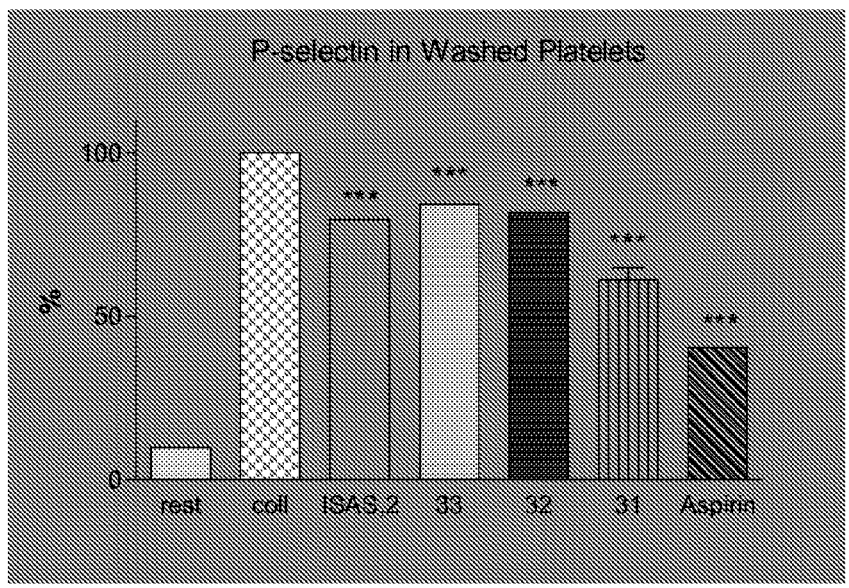
FIG. 35: P-selectin expression to collagen in washed platelets with test compounds 2, 31-33, aspirin. Here again in washed platelets there is some dampening of glycoprotein expression (significant difference with collagen (***P<0.001). However in washed platelet suspensions which lack esterases the compounds are not as effective as aspirin.

Using rabbit liver carboxylesterase, the hydrolysis of the drug was measured and 5.99 µM aspirin was produced (FIG. 18)—similar levels to HLM.

BNPP a know carboxylesterase inhibitor was incubated with HIM and HLM for 10 mins prior to addition of the drug so as to knock out carboxylesterase activity. A marked decrease in aspirin production was seen and after 60 mins the drug had not disappeared. It can be concluded that ISAS is a substrate for CE-1 and CE-2 as well as BuChE. These enzymes belong to the same family but have marked difference in substrate specificity. For example the CE enzymes are inefficient in the hydrolysis of positively charged substrates such as those favoured by BuChE, including choline esters. These enzymes are not normally grouped together. Surprisingly in the case of ISAS, CE-2 present in the HIM preparations exhibits the same specificity and efficiency as BuChE and is as good a vector for aspirin release. The result indicates that more than one enzyme is capable of releasing aspirin from the compounds.

TABLE 5

Comparison of aspirin production with different biological samples using ISAS

| Biological medium | Conc drug (mM) | Aspirin (µM) | Salicylic acid (µM) | Drug disappearance (min) |
|---|---|---|---|---|
| 50% Human Plasma (female) | 0.1 | 22 | 4 | 10 |
| 50% Rabbit Plasma | 0.1 | 2.6 | 25 | 20 |
| Carboxylesterase (16.4 u/ml) | 0.1 | 5.7 | 53 | 5 |
| HIM (80 µg/ml) | 0.1 | 27 | 9 | 5 |
| HIM (40 µg/ml)/ BNPP(14 µM) | 0.1 | 2.2 | 0 | 9.4 µM left |
| HLM(0.2 mg/ml)) | 0.1 | 9 | 34 | 10 |
| HLM/BNPP (11.6 uM) | 0.11 | 2.7 | 3.0 | 2.8 µM left |
| HLM/isoOMPA (10 uM) | 0.11 | 8.5 | 33 | 10 |

TABLE 6

Comparison of aspirin production using different biological samples with Is-2-aspirinate-5-(3-nitrooxy-methyl)benzoate 21.

| Biological medium | Conc drug (mM) | Aspirin (µM) | Salicylic acid (µM) | Drug disappearace (min) |
|---|---|---|---|---|
| 50% HP | 0.25 | 26 | 18 | 10 |
| 80% HP | 0.1 | 21 | 9 | 10 |
| Purified human serum (0.15 mg/ml) | 0.12 | 15 | 6 | 10 |
| HLM (0.2 mg/ml) | 0.13 | 5 | 6 | 10 |
| HLM/iso-OMPA (14.4 µM) | 0.1 | 1.4 | 4.5 | 20 |
| HLM/BNPP (10.6 µM) | 0.1 | 0.3 | 0.9 | 13 µM left |
| HIM (80 µg/ml) | 0.1 | 20 | 4 | 10 |
| HIM/BNPP (11.6 uM) | 0.11 | 0.22 | 1.3 | 11 µM left |
| HIM/isoOMPA (14.14 uM) | 0.11 | 12.7 | 7.2 | 30 |

Hydrolysis results for Is-2-aspirinate-5-(4-nitrooxy-methyl)benzoate 22

TABLE 7

Effect of NO position on aspirin production

| Biological source | 2-nitrooxy (5) (µM) | 3-nitrooxy (4) (µM) | 4-nitrooxy (6) (µM) |
|---|---|---|---|
| 50% human plasma | 10.3 | 26 | 2 |
| HIM (80 µg/ml) | 21.7 | 20 | 9.7 |

Hydrolysis results of non-isosorbide-based reference aspirin esters

The hydrolysis of two non-isosorbide based aspirin esters i.e., 2-methoxyphenyl-2-acetoxybenzoate (guaicol ester) and 2-acetoxybenzoic acid phenyl ester was evaluated in human intestinal microsomes (40 µg/ml). Neither of these esters acts as an aspirin prodrug in human plasma i.e. human plasma esterase action does not cause the release of aspirin from these esters.

TABLE 8

Aspirin production of non-isosorbide based aspirin esters in HIM

| Biological source | Guaicol aspirin ester (µM) | 2-acetoxybenzoic acid phenyl ester (µM) |
|---|---|---|
| HIM (40 µg/ml) | 0.5 (µM) | 7.7 (µM) |
| HIM (20 µg/ml) | — | 5.3 (µM) |

The phenyl aspirinates produced negligible amounts of aspirin in contact with human intestinal microsomes, illustrating that for these substrates the CE-2 preference is slightly different to BuChE, in the presence of which hydrolysis occurs without the evolution of aspirin. However, relative to ISAS and the nitroxymethyl analogues there was little aspirin production. In other words these compounds are not aspirin prodrugs in human plasma and are inefficient aspirin prodrugs in the presence of CE-2. The data illustrates that the interaction between CE-2 and the prodrugs of the invention is special in that effective aspirin production occurs.

TABLE 9

Comparison of amounts of aspirin produced from Is-2-aspirinate-5-salicylate and Is-2-aspirinate-5-(3-nitrooxymethyl)benzoate

| Biological medium | Is-2-asp-5-salicylate | Is-2-asp-5-(3-nitrooxymethyl)benzoate |
|---|---|---|
| 50% HP | 22 | 21 |
| HLM (0.2 mg/ml) | 9 | 5 |
| HLM/iso-OMPA (14.4 µM) | 8.5 | 1.4 |
| HLM/BNPP (10.6 µM) | 2.7 | 0.3 |
| HIM (80 µg/ml) | 27 | 20 |
| HIM/BNPP (11.6 uM) | 2.2 | 0.22 |
| HIM/isoOMPA (14.14 uM) | — | 12.7 |

REFERENCES

Albert, A. 1958. Chemical aspects of selective toxicity. Nature, 182, 421-422

Burton, D. J. and Koppes, W. M. 1975. Cleavage of carboxylic acid esters to acid chlorides with dichlorotriphenylphosphorane. J. Org. Chem 40, No 21, 3026-3032.

Carini M, Aldini G, Orioli M, Maffei Facino R. In vitro metabolism of a nitroderivative of acetylsalicylic acid (NCX4016) by rat liver: LC and LC-MS studies. J Pharm Biomed Anal. 2002 Aug. 1; 29(6):1061-71.

Cena C, Lolli M L, Lazzarato L, Guaita E, Morini G, Coruzzi G, McElroy S P, Megson I L, Fruttero R, Gasco A. 2003. Antiinflammatory, gastrosparing, and antiplatelet properties of new NO-donor esters of aspirin.

Cena C, Lolli M L, Lazzarato L, Guaita E, Morini G, Coruzzi G, McElroy S P, Megson I L, Fruttero R, Gasco A. Antiinflammatory, gastrosparing, and antiplatelet properties of new NO-donor esters of aspirin. 2003 J Med Chem. February 27; 46(5):747-54.

Chan A T, Giovannucci E L, Meyerhardt J A, Schernhammer E S, Curhan G C, Fuchs C S. 2005. Long-term use of aspirin and nonsteroidal anti-inflammatory drugs and risk of colorectal cancer. JAMA. August 24; 294(8):914-23.

Corazzi T, Leone M, Maucci R, Corazzi L, Gresele P. 2005 Direct and irreversible inhibition of cyclooxygenase-1 by nitroaspirin (NCX 4016). J Pharmacol Exp Ther. 315(3): 1331-7.

Cryer B. 2002 Gastrointestinal safety of low-dose aspirin. Am J Manag Care. December; 8(22 Suppl):S701-8.

Cryer B & Feldman M. Effects of very low dose daily, long-term aspirin therapy on gastric, duodenal, and rectal prostaglandin levels and on mucosal injury in healthy humans. Gastroenterology. 1999 July; 117(1):17-25.

Ellman, G L, Courtney, K D, Andres J R, V. and Featherstone, R. M. (1961) A new and rapid colorimetric determination of acetylcholinesterase activity. Biochemical Pharmacology 7, 88-95.

Etminan M, Gill S, Samii A. 2003. Effect of non-steroidal anti-inflammatory drugs on risk of Alzheimers disease: systematic review and meta-analysis of observational studies. BMJ. July 19; 327(7407):128.

Fiorucci S et al, Gastrointestinal safety of NO-aspirin (NCX-4016) in healthy human volunteers: a proof of concept endoscopic study. Gastroenterology. 2003 (3):600-7.

Fiorucci, S. and Del. Soldato, P. (2003) NO-aspirin:mechanism of action and gastrointestinal safety. Digestive and liver Disease 35 (suppl 2), 9-19.

Gilmer J. F. Gilmer J F, Murphy M A, Shannon J A, Breen C G, Ryder S A, Clancy J M. et al 2003, Single oral dose study of two isosorbide-based aspirin prodrugs in the dog. Pharm. Pharmacol. 55, 10, 1351-7.

Gilmer J. F., Moriarty L M, Lally M N, Clancy J M. 2002. Isosorbide-based aspirin prodrugs. II. Hydrolysis kinetics of isosorbide diaspirinate. European Journal of Pharmaceutical Sciences. 16(4-5). 297-304.

Gilmer J F, Moriarty L M, Clancy J M. 2007. Evaluation of nitrate-substituted pseudocholine esters of aspirin as potential nitro-aspirins. Bioorg. Med. Chem. Lett. 2007 Jun. 1; 17(11):3217-20. Epub 2007 Mar. 12.

Gilmer J F, Moriarty L M, McCafferty D F, Clancy J M. 2001. Synthesis, hydrolysis kinetics and anti-platelet effects of isosorbide mononitrate derivatives of aspirin. Eur J Pharm Sci. October; 14(3):221-7.

Jones G., 1985. Decreased toxicity and adverse reaction via prodrugs. In Bundgaard H., (Ed.) Design of Prodrugs, Elsevier, Amsterdam, 199-241.

Jurasz, P., Stewart, M. W., Radomski, A., Khadour, F., Duszyk, M. & Radomski, M. W. (2001). Role of von Willebrand factor in tumour cell-induced platelet aggregation: differential regulation by NO and prostacyclin. British Journal of Pharmacology, 134, 1104-12.

Kelly J P, Kaufman D W, Jurgelon J M, Sheehan J, Koff R S, Shapiro S. 1996. Risk of aspirin-associated major upper-gastrointestinal bleeding with enteric-coated or buffered product. Lancet. November 23; 348(9039):1413-6.

Laheij R J, 2001, *Helicobacter pylori* infection as a risk factor for gastrointestinal symptoms in patients using aspirin to prevent ischaemic heart disease. Aliment Pharmacol Ther, 15: 1055-9.

Levin R I. et al 2004 Theriac found Nitric oxide-aspirin and the search for the universal cure. J Am Coll Cardiol. 44, 642-3.

Li, B., Sedlacek, M., Manoharan, I., Boopathy, R., Duysen, E. G., Masson, P. and Lockridge, O. (2005) Butyrylcholinesterase, paraoxonase, and albumin esterase, but not carboxylesterase, are present in in human plasma. Biochemical Pharmacology 70, 1673-1684.

Mashita et al, Taniguchi M., Yokota A., Tanaka A., Takeuchi K., 2006 Oral but Not Parenteral Aspirin Upregulates COX-2 Expression in Rat Stomachs Digestion 73, (2-3), 143-132.

Morgan G., 2003, A quantitative illustration of the public health potential of aspirin. Med Hypotheses 60: 900-2.

Moriarty, L. M. (2002) Studies in the synthesis and in vitro hydrolysis of novel aspirin prodrugs. Ph.D thesis, Trinity College Dublin 2, Ireland.

Moriarty L M, Lally M N, Carolan C G, Jones M, Clancy J M, Gilmer J F. *Discovery of a true aspirin prodrug*. J Med Chem. 2008 Dec. 25; 51(24):7991-9.

Newton, J. L., Johns, C. E. May, F. E. B 2004. The ageing bowel and intolerance to aspirin. Alimentary pharmacology & therapeutics. 19(1):39-45.

Nielsen N M, Bundgaard, H. 1989. Evaluation of glycolamide esters and various other esters of aspirin as true aspirin prodrugs. J Med Chem. 32(3):727-34.

Pedersen A. K. & FitzGerald G. A. 1984 Dose-related kinetics of aspirin. Presystemic acetylation of platelet cyclooxygenase. N Engl J Med. 311, 1206-11.

Qu S Y, Li W, Chen Y L, Sun Y, hang Y Q, Hong T., 1990. The physiologic disposition and pharmacokinetics of guaiacol acetylsalicylate in rats. Yao Xue Xue Bao 25, 664-669.

Radomski, A., Stewart, M. W., Jurasz, P. & Radomski, M. W. (2001). Pharmacological characteristics of solid-phase von Willebrand factor in human platelets. British Journal of Pharmacology, 134, 1013-20.

Soars, M. G., Burchell, B. and Riley, R. J. (2002) In vitro analysis of human drug glucuronidation and prediction of in vivo metabolic clearance. Journal of Pharmacology and Experimental therapeutics 301, 382-390.

St Pierre T, Jencks W P. 1968 Intramolecular catalysis in the reactions of nucleophilic reagents with aspirin. J Am Chem Soc. July 3; 90(14):3817-27.

Tesei A, Ricotti L, Ulivi P, Medri L, Amadori D, oli W. Tesei A et al. 2003. NCX 4016, a nitric oxide-releasing aspirin derivative, exhibits a significant antiproliferative effect and alters cell cycle progression in human colon adenocarcinoma cell lines. 2003. Int J Oncol 22(6):1297-302. Gilmer J. F. et al 2003, Pharm. Pharmacol. 55, 10, 1351-7.

Velzquez C, Praveen Rao P N, Knaus E E. 2005. J Med Chem. 2005 Jun. 16; 48(12):4061-7. Novel nonsteroidal antiinflammatory drugs possessing a nitric oxide donor diazen-1-ium-1,2-diolate moiety: design, synthesis, biological evaluation, and nitric oxide release studies. J Med Chem. June 16; 48(12):4061-7.

Walker J, Robinson J, Stewart J, Jacob S. 2007 Does enteric-coated aspirin result in a lower incidence of gastrointestinal complications compared to normal aspirin Interact Cardiovasc Thorac Surg. August; 6(4):519-22.

Williams F. M, 1989. Williams F M, Moore U, Seymour R A, Mutch E M, Nicholson E, Wright P, Wynne H, Blain P G, Rawlins M D. 1989. Benorylate hydrolysis by human plasma and human liver. Br. J. Clin. Pharmacol. 28, 703-8.

The invention claimed is:

1. An isosorbide aspirinate compound having the structure:

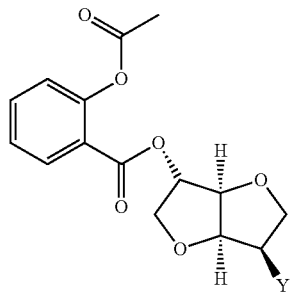

wherein Y is selected from the group consisting of:
(i) a $C_1$-$C_8$ alkyl ester, a $C_1$-$C_8$ alkoxy ester, a $C_3$-$C_{10}$ cycloalkyl ester, an arylester or a $C_1$-$C_8$ alkylaryl ester, which can be unsubstituted or substituted with at least one substituent selected from nitrate ester, $C_1$-$C_8$ alkyl nitrate ester or a $C_3$-$C_{10}$ cycloalkyl nitrate ester;
(ii) a $C_1$-$C_8$ alkyl ester or a $C_1$-$C_8$ alkoxy ester, which can be unsubstituted or substituted with $ONO_2$; or a $C_3$-$C_{10}$ cycloalkyl ester or a $C_1$-$C_8$ cycloalkoxy ester, which can be unsubstituted or substituted with $ONO_2$; or an unsubstituted or a substituted arylester, alkylaryl ester, benzoate, a nicotinate oxazoleoate, isoxazoleate, thiadiazoleoate group, which may be substituted by at least one of the group comprising hydroxide, —Cl, —Br, a $C_1$-$C_8$ alkyl, benzyl, a $C_1$-$C_8$ alkoxy, benzyloxy, —NHC(O)R, —$NH_2$, —$NO_2$, —$ONO_2$, —$(CH_2)_nONO_2$, —OC(O)[$(CH_2)_m]_{cyclic}ONO_2$, —$OCOArONO_2$, —OCOAr$(CH_2)_nONO_2$ or a $C_1$-$C_5$ haloalkyl ester, wherein R is a $C_1$-$C_8$ alkyl or a $C_1$-$C_8$ alkoxy group, n=1-8, m=3-10;
(iii) a $C_1$-$C_8$ alkyl ester or a $C_1$-$C_8$ alkoxy ester, which can be unsubstituted or substituted with $ONO_2$; or an unsubstituted or a substituted arylester, alkylaryl ester, benzoate, nicotinate, oxazoleoate, isoxazoleate, thiadiazoleoate group, which may be substituted by at least one of the group comprising hydroxide, —Cl, —Br, a $C_1$-$C_8$ alkyl, benzyl, a $C_1$-$C_8$ alkoxy, o-benzyloxy, —NHC(O)R, —$NH_2$, —$NO_2$, —$ONO_2$, —$(CH_2)_nONO_2$, —C(O)[$(CH_2)_m]_{cyclic}ONO_2$, —$OCOArONO_2$, —OCOAr$(CH_2)_nONO_2$ or a $C_1$-$C_5$ haloalkyl ester, wherein R is a $C_1$-$C_8$ alkyl or a $C_1$-$C_8$ alkoxy group, n=1-8, m=3-10;
(iv) a $C_1$-$C_8$ alkoxy ester, which can be unsubstituted or substituted with $ONO_2$; or an unsubstituted or a substituted benzoate or nicotinate group, which may be substituted by at least one of the group comprising hydroxide, —Cl, —Br, a $C_1$-$C_8$ alkyl, benzyl, a $C_1$-$C_8$ alkoxy, o-benzyloxy, —NHC(O)R, —$NH_2$, —$NO_2$, —$ONO_2$, —$(CH_2)_nONO_2$, —OC(O)[$(CH_2)_m]_{cyclic}ONO_2$, —$OCOArONO_2$, —OCOAr$(CH_2)_nONO_2$ or a $C_1$-$C_5$ haloalkyl ester, wherein R is a $C_1$-$C_8$ alkyl or a $C_1$-$C_8$ alkoxy group, n=1-8, m=3-10;

(v) an unsubstituted or a substituted benzoate or nicotinate group, which may be substituted by at least one of hydroxide, $C_1$-$C_8$ alkyl, $C_1$-$C_8$ alkyoxy, o-benzyloxy, —(CH$_2$)$_n$ONO$_2$ (n=1-8), $C_3$-$C_{10}$ cycloalkyl ester or haloalkyl ester; and (vi) an unsubstituted or a substituted benzoate or nicotinate group, which may be substituted by at least one of hydroxide, —Cl, methyl, o-benzyloxy, methoxy, —NHC(O)CH$_3$, —OC(O)CH$_2$Br, —NO$_2$, —CH$_2$ONO$_2$, wherein Y is an unsubstituted or a substituted benzoate or nicotinate group, which may be substituted by at least one of hydroxide, —Cl, methyl, o-benzyloxy, methoxy, —NHC(O)CH$_3$, —OC(O)CH$_2$Br, —NO$_2$, —CH$_2$ONO$_2$;

wherein the isosorbide aspirinate compound is not a compound having the structure:

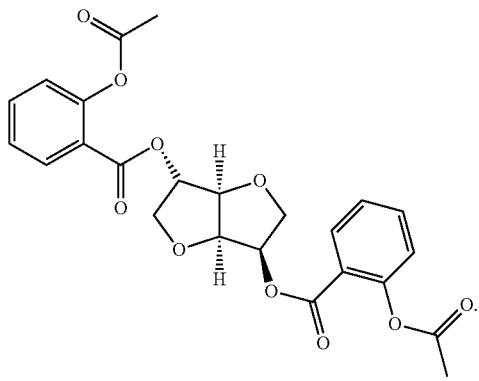

2. The isosorbide aspirinate compound of claim 1, wherein Y is a $C_1$-$C_8$ alkyl ester, a $C_1$-$C_8$ alkoxy ester, a $C_3$-$C_{10}$ cycloalkyl ester, an arylester, or a $C_1$-$C_8$ alkylaryl ester, which can be unsubstituted or substituted with at least one substituent selected from nitrate ester, $C_1$-$C_8$ alkyl nitrate ester or a $C_3$-$C_{10}$ cycloalkyl nitrate ester.

3. A compound according to claim 1 wherein the halo substituent on the haloalkyl ester is Cl, Br or F.

4. A compound according to claim 1, wherein Y is selected from the group consisting of:

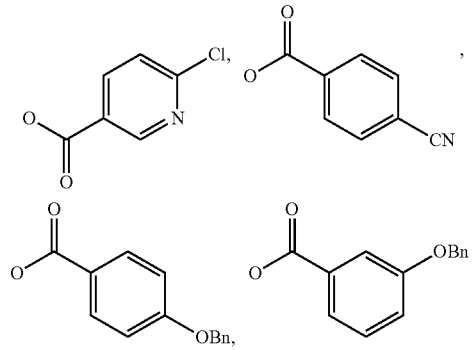

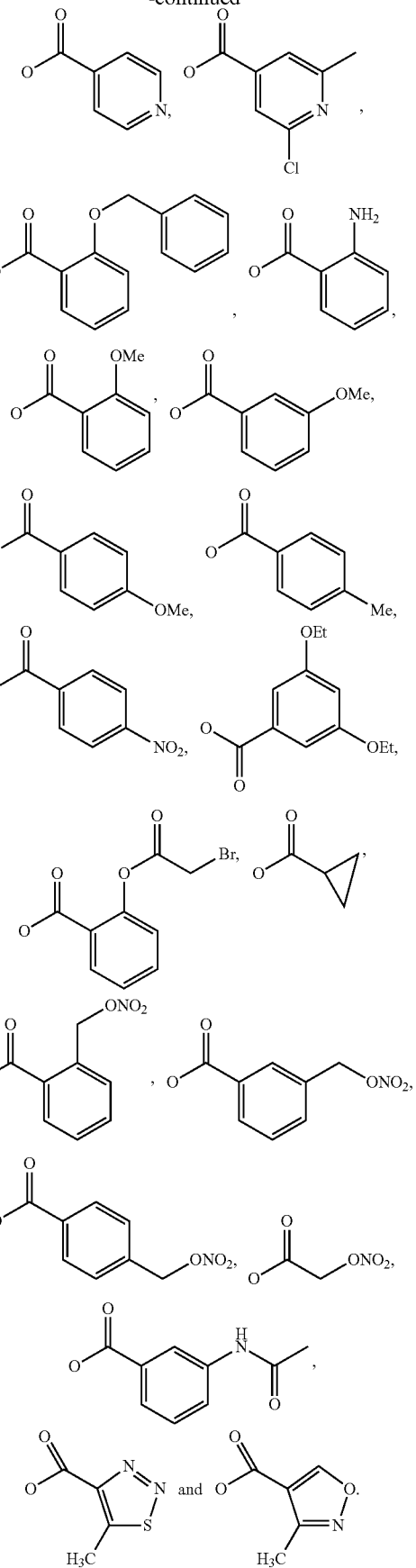

5. A compound according to claim 1 wherein Y is selected from the group consisting of:
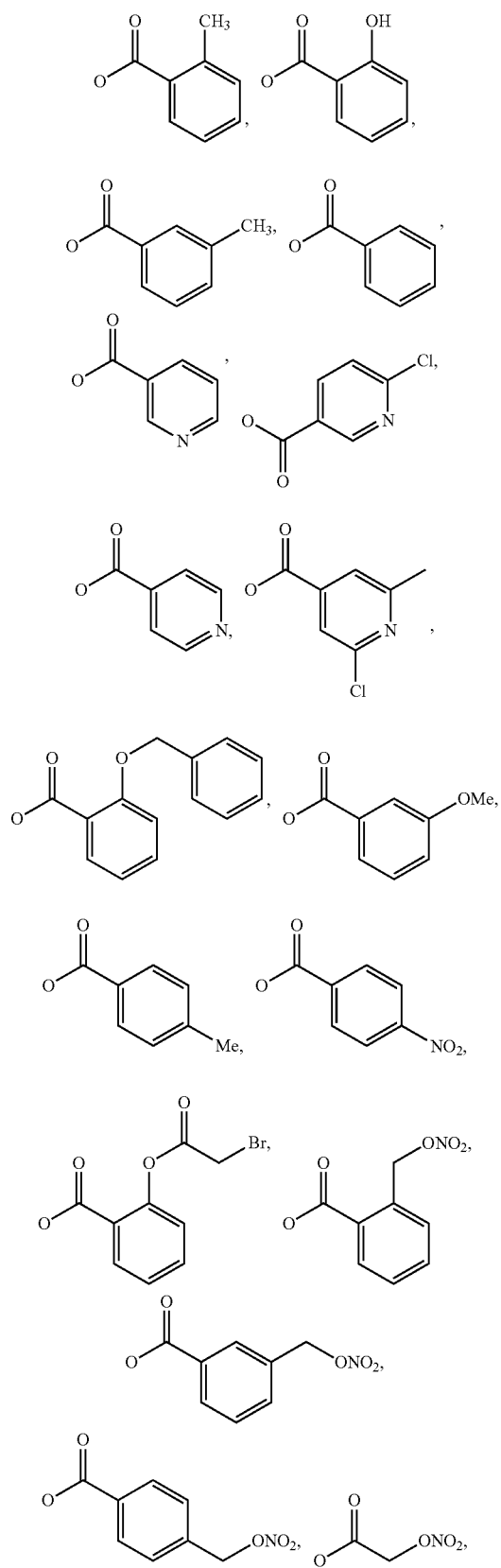
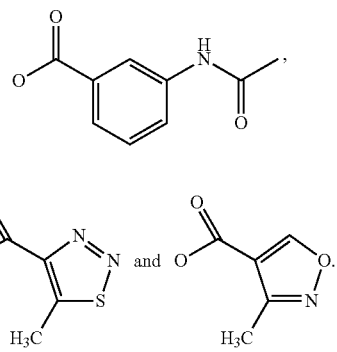
6. An isosorbide aspirinate compound according to claim 1 having the structure selected from the group consisting of:
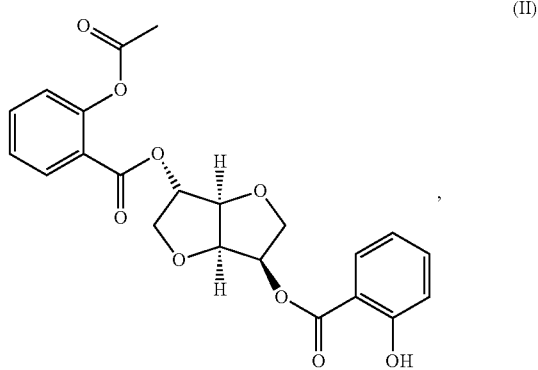
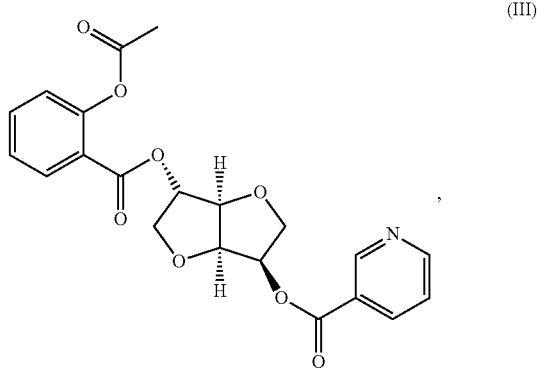
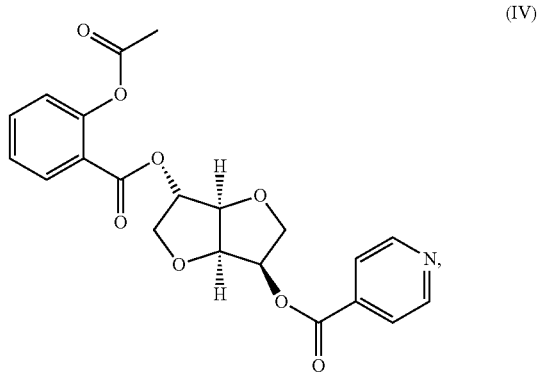

75
-continued (V)
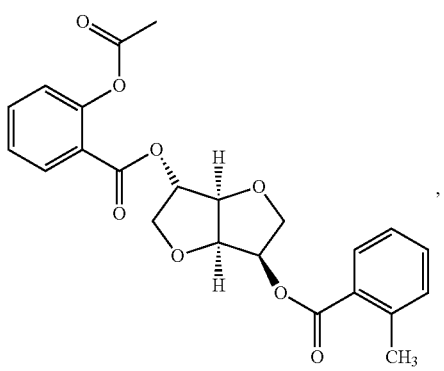, (VI)
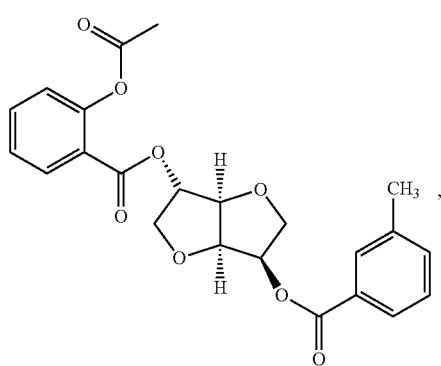, (VII)
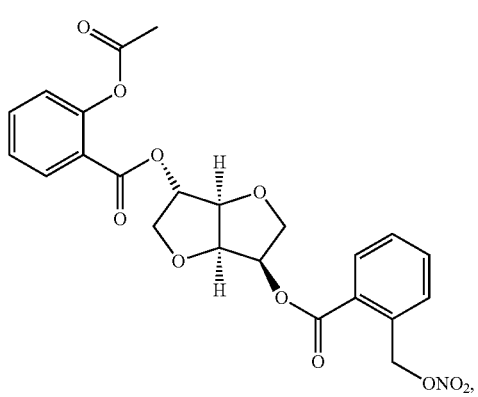, (VIII)
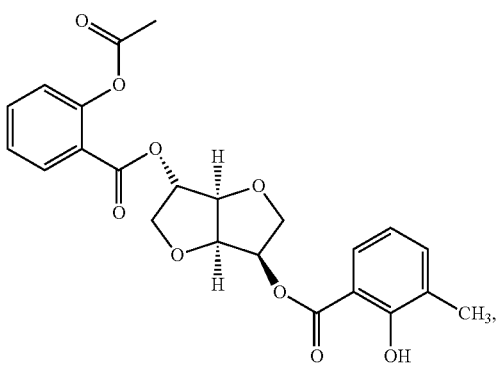

76
-continued (IX)
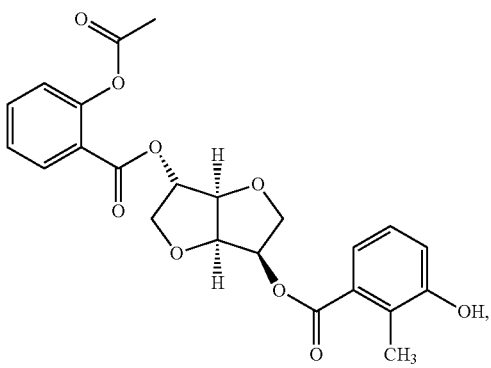

(X)
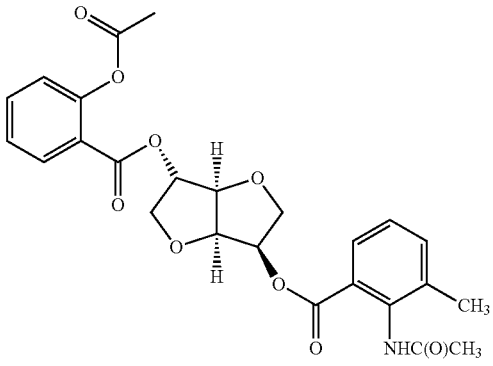 and (XI)
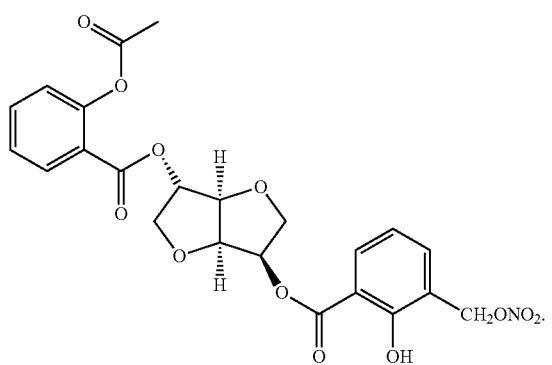

7. A carrier compound for a drug having the general structure:

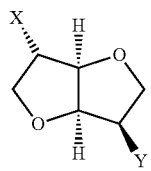

wherein Y is selected from the group consisting of:
(i) a $C_1$-$C_8$ alkyl ester, a $C_1$-$C_8$ alkoxy ester, a $C_3$-$C_{10}$ cycloalkyl ester, a $C_1$-$C_8$ cycloalkoxy ester, an aryl ester or a $C_1$-$C_8$ alkyl aryl ester, which can be unsubstituted or substituted with at least one substituent selected from nitrate ester, $C_1$-$C_8$ alkyl nitrate ester or a $C_3$-$C_{10}$ cycloalkyl nitrate ester, (ii) a $C_1$-$C_8$ alkyl ester or a $C_1$-$C_8$ alkoxy ester, which can be unsubstituted or substituted with $ONO_2$; or a $C_3$-$C_{10}$ cycloalkyl ester or a $C_1$-$C_8$ cyclo alkoxy ester, which can be unsubstituted or substituted with $ONO_2$; or an unsubstituted or a substituted aryl ester, alkyl aryl ester, benzoate or nicotinate group, which may be substituted by at least one of the group comprising hydroxide, a $C_1$-$C_8$ alkyl, benzyl, a $C_1$-$C_8$ alkoxy, benzyloxy, —NHC(O)R, —$NH_2$, —$NO_2$, —$ONO_2$, —$(CH_2)_nONO_2$, —OC(O)[$(CH_2)_m]_{cyclic}ONO_2$, —$OCOArONO_2$, —OCOAr$(CH_2)_nONO_2$ or a $C_1$-$C_5$ haloalkyl ester, wherein R is a $C_1$-$C_8$ alkyl or a $C_1$-$C_8$ alkoxy group, n=1-8, m=3-10; and (iii) a $C_1$-$C_8$ alkoxy ester, which can be unsubstituted or substituted with $ONO_2$; or a $C_3$-$C_{10}$ cycloalkyl ester or a $C_1$-$C_8$ cyclo alkoxy ester, which can be unsubstituted or substituted with $ONO_2$; or an unsubstituted or a substituted benzoate or nicotinate group, which may be substituted by at least one of the group comprising hydroxide, a $C_1$-$C_8$ alkyl, benzyl, a $C_1$-$C_8$ alkoxy, benzyloxy, —NHC(O)R, —$NH_2$, —$NO_2$, —$ONO_2$, —$(CH_2)_n$ $ONO_2$, —OC(O)[$(CH_2)_m]_{cyclic}ONO_2$, —OCOAr $ONO_2$, —OCOAr $(CH_2)_nONO_2$ or a $C_1$-$C_5$ haloalkyl ester, wherein R is a $C_1$-$C_8$ alkyl or a $C_1$-$C_8$ alkoxy group, n=1-8, m=3-10; and X is the drug molecule;

wherein the isosorbide aspirinate compounds is not a compound having the structure:

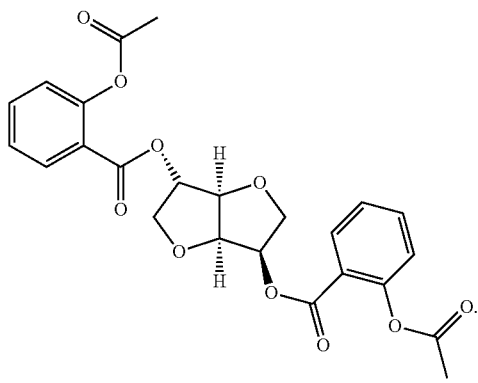

8. A carrier compound according to claim 7, wherein Y is a $C_1$-$C_8$ alkyl ester, a $C_1$-$C_8$ alkoxy ester, a $C_3$-$C_{10}$ cycloalkyl ester, an arylester, or a $C_1$-$C_8$ alkylaryl ester, which can be unsubstituted or substituted with at least one substituent selected from nitrate ester, $C_1$-$C_8$ alkyl nitrate ester or a $C_3$-$C_{10}$ cycloalkyl nitrate ester.

9. A pharmaceutical composition comprising a compound according to claim 1 and at least one pharmaceutically acceptable carrier or excipient.

10. A compound according to claim 1 wherein Y is an alkyl or aryl ester.

11. A composition comprising a carrier according to claim 7 and at least one pharmaceutically acceptable carrier or excipient.

12. A method of treating a cardiovascular or cerebrovascular disease comprising administering to a patient in need thereof a compound having the structure:

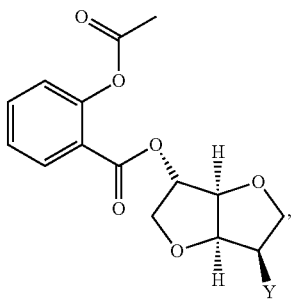

or a pharmaceutical composition thereof, wherein Y is selected from the group consisting of:

(i) a $C_1$-$C_8$ alkyl ester, a $C_1$-$C_8$ alkoxy ester, a $C_3$-$C_{10}$ cycloalkyl ester, an arylester or a $C_1$-$C_8$ alkylaryl ester, which can be unsubstituted or substituted with at least one substituent selected from nitrate ester, $C_1$-$C_8$ alkyl nitrate ester or a $C_3$-$C_{10}$ cycloalkyl nitrate ester;

(ii) a $C_1$-$C_8$ alkyl ester or a $C_1$-$C_8$ alkoxy ester, which can be unsubstituted or substituted with $ONO_2$; or a $C_3$-$C_{10}$ cycloalkyl ester or a $C_1$-$C_8$ cycloalkoxy ester, which can be unsubstituted or substituted with $ONO_2$; or an unsubstituted or a substituted arylester, alkylaryl ester, benzoate, a nicotinate oxazoleoate, isoxazoleate, thiadiazoleoate group, which may be substituted by at least one of the group comprising hydroxide, —Cl, —Br, a $C_1$-$C_8$ alkyl, benzyl, a $C_1$-$C_8$ alkoxy, benzyloxy, —NHC(O)R, —$NH_2$, —$NO_2$—$ONO_2$, —$(CH_2)_nONO_2$, —OC(O)[$(CH_2)_m]_{cyclic}ONO_2$, —$OCOArONO_2$—OCOAr$(CH_2)_nONO_2$ or a $C_1$-$C_5$ haloalkyl ester, wherein R is a $C_1$-$C_8$ alkyl or a $C_1$-$C_8$ alkoxy group, n=1-8, m=3-10;

(iii) a $C_1$-$C_8$ alkyl ester or a $C_1$-$C_8$ alkoxy ester, which can be unsubstituted or substituted with $ONO_2$; or an unsubstituted or a substituted arylester, alkylaryl ester, benzoate, nicotinate, oxazoleoate, isoxazoleate, thiadiazoleoate group, which may be substituted by at least one of the group comprising hydroxide, —Cl, —Br, a $C_1$-$C_8$ alkyl, benzyl, a $C_1$-$C_8$ alkoxy, o-benzyloxy, —NHC(O)R, —$NH_2$, —$NO_2$, —$ONO_2$, —$(CH_2)_nONO_2$, —C(O)[$(CH_2)_m]_{cyclic}ONO_2$, —$OCOArONO_2$, —OCOAr$(CH_2)_nONO_2$ or a $C_1$-$C_5$ haloalkyl ester, wherein R is a $C_1$-$C_8$ alkyl or a $C_1$-$C_8$ alkoxy group, n=1-8, m=3-10;

(iv) a $C_1$-$C_8$ alkoxy ester, which can be unsubstituted or substituted with $ONO_2$; or an unsubstituted or a substituted benzoate or nicotinate group, which may be substituted by at least one of the group comprising hydroxide, —Cl, —Br, a $C_1$-$C_8$ alkyl, benzyl, a $C_1$-$C_8$ alkoxy, o-benzyloxy, —NHC(O)R, —$NH_2$, —$NO_2$, —$ONO_2$, —$(CH_2)_nONO_2$, —OC(O)[$(CH_2)_m]_{cyclic}ONO_2$, —$OCOArONO_2$, —OCOAr$(CH_2)_nONO_2$ or a $C_1$-$C_5$ haloalkyl ester, wherein R is a $C_1$-$C_8$ alkyl or a $C_1$-$C_8$ alkoxy group, n=1-8, m=3-10;

(v) an unsubstituted or a substituted benzoate or nicotinate group, which may be substituted by at least one of hydroxide, $C_1$-$C_8$ alkyl, $C_1$-$C_8$ alkyoxy, o-benzyloxy, —$(CH_2)_nONO_2$ (n=1-8), $C_3$-$C_{10}$ cycloalkyl ester or haloalkyl ester; and an unsubstituted or a substituted benzoate or nicotinate group, which may be substituted by at least one of hydroxide, —Cl, methyl, o-benzyloxy, methoxy, —$NHC(O)CH_3$, —$OC(O)CH_2Br$, —$NO_2$, —$CH_2ONO_2$, wherein Y is an unsubstituted or a substituted benzoate or nicotinate group, which may be substituted by at least one of hydroxide, —Cl, methyl, o-benzyloxy, methoxy, —NHC(O)CH$_3$, —OC(O)CH$_2$Br, —NO$_2$, —CH$_2$ONO$_2$;

wherein Y is not nicotinate; and wherein the compound is not a compound having the structure:

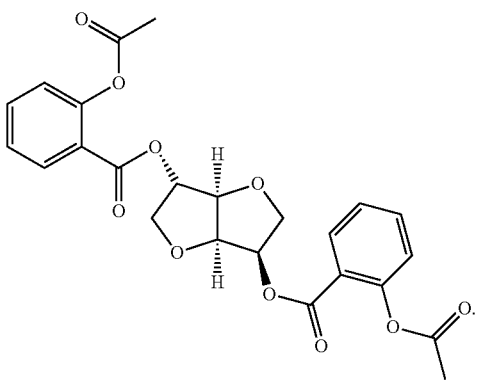

13. The method of claim 12, wherein the compound reduces constitutive platelet glycol-protein expression at a level where aspirin has no effect.

14. The method of claim 12, wherein the compound induces an aspirin like effect.

15. A method of treating a disease selected from pain, pyrexia, inflammation, cancer, Alzheimer's disease or dementia disease, comprising administering to a patient in need thereof a compound having the structure:

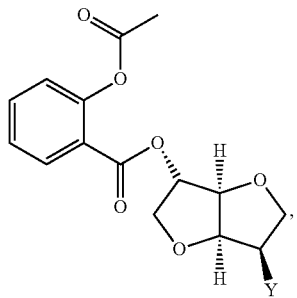

or a pharmaceutical composition thereof, wherein Y is selected from the group consisting of:
(i) a $C_1$-$C_8$ alkyl ester, a $C_1$-$C_8$ alkoxy ester, a $C_3$-$C_{10}$ cycloalkyl ester, an arylester or a $C_1$-$C_8$ alkylaryl ester, which can be unsubstituted or substituted with at least one substituent selected from nitrate ester, $C_1$-$C_8$ alkyl nitrate ester or a $C_3$-$C_{10}$ cycloalkyl nitrate ester;
(ii) a $C_1$-$C_8$ alkyl ester or a $C_1$-$C_8$ alkoxy ester, which can be unsubstituted or substituted with ONO$_2$; or a $C_3$-$C_{10}$ cycloalkyl ester or a $C_1$-$C_8$ cycloalkoxy ester, which can be unsubstituted or substituted with ONO$_2$; or an unsubstituted or a substituted arylester, alkylaryl ester, benzoate, a nicotinate oxazoleoate, isoxazoleate, thiadiazoleoate group, which may be substituted by at least one of the group comprising hydroxide, —Cl, —Br, a $C_1$-$C_8$ alkyl, benzyl, a $C_1$-$C_8$ alkoxy, benzyloxy, —NHC(O)R, —NH$_2$, —NO$_2$, —ONO$_2$, —(CH$_2$)$_n$ONO$_2$, —OC(O)[(CH$_2$)$_m$]$_{cyclic}$ONO$_2$, —OCOArONO$_2$, —OCOAr(CH$_2$)$_n$ONO$_2$ or a $C_1$-$C_5$ haloalkyl ester, wherein R is a $C_1$-$C_8$ alkyl or a $C_1$-$C_8$ alkoxy group, n=1-8, m=3-10;
(iii) a $C_1$-$C_8$ alkyl ester or a $C_1$-$C_8$ alkoxy ester, which can be unsubstituted or substituted with ONO$_2$; or an unsubstituted or a substituted arylester, alkylaryl ester, benzoate, nicotinate, oxazoleoate, isoxazoleate, thiadiazoleoate group, which may be substituted by at least one of the group comprising hydroxide, —Cl, —Br, a $C_1$-$C_8$ alkyl, benzyl, a $C_1$-$C_8$ alkoxy, o-benzyloxy, —NHC(O)R, —NH$_2$, —NO$_2$, —ONO$_2$, —(CH$_2$)$_n$ONO$_2$, —C(O)[(CH$_2$)$_m$]$_{cyclic}$ONO$_2$, —OCOArONO$_2$, —OCOAr(CH$_2$)$_n$ONO$_2$ or a $C_1$-$C_5$ haloalkyl ester, wherein R is a $C_1$-$C_8$ alkyl or a $C_1$-$C_8$ alkoxy group, n=1-8, m=3-10;
(iv) a $C_1$-$C_8$ alkoxy ester, which can be unsubstituted or substituted with ONO$_2$; or an unsubstituted or a substituted benzoate or nicotinate group, which may be substituted by at least one of the group comprising hydroxide, —Cl, —Br, a $C_1$-$C_8$ alkyl, benzyl, a $C_1$-$C_8$ alkoxy, o-benzyloxy, —NHC(O)R, —NH$_2$, —NO$_2$, —ONO$_2$, —(CH$_2$)$_n$ONO$_2$, —OC(O)[(CH$_2$)$_m$]$_{cyclic}$ONO$_2$, —OCOArONO$_2$, —OCOAr(CH$_2$)$_n$ONO$_2$ or a $C_1$-$C_5$ haloalkyl ester, wherein R is a $C_1$-$C_8$ alkyl or a $C_1$-$C_8$ alkoxy group, n=1-8, m=3-10;
(v) an unsubstituted or a substituted benzoate or nicotinate group, which may be substituted by at least one of hydroxide, $C_1$-$C_8$ alkyl, $C_1$-$C_8$ alkyoxy, o-benzyloxy, —(CH$_2$)$_n$ONO$_2$ (n=1-8), $C_3$-$C_{10}$ cycloalkyl ester or haloalkyl ester; and
(vi) an unsubstituted or a substituted benzoate or nicotinate group, which may be substituted by at least one of hydroxide, —Cl, methyl, o-benzyloxy, methoxy, —NHC(O)CH$_3$, —OC(O)CH$_2$Br, —NO$_2$, —CH$_2$ONO$_2$, wherein Y is an unsubstituted or a substituted benzoate or nicotinate group, which may be substituted by at least one of hydroxide, —Cl, methyl, o-benzyloxy, methoxy, —NHC(O)CH$_3$, —OC(O)CH$_2$Br, —NO$_2$, —CH$_2$ONO$_2$;

wherein the compound is not a compound having the structure:

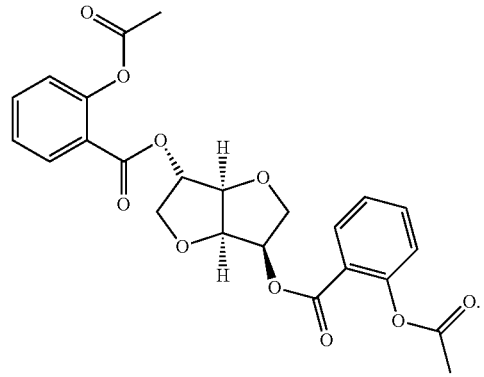

16. A method of treating a disease selected from cardiovascular and cerebrovascular disorders, comprising administering to a patient in need thereof a compound having the structure:

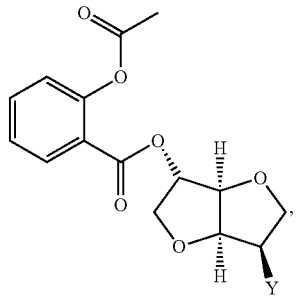

or a pharmaceutical composition thereof, wherein Y is selected from the group consisting of:
(i) a $C_1$-$C_8$ alkyl ester, a $C_1$-$C_8$ alkoxy ester, a $C_3$-$C_{10}$ cycloalkyl ester, an arylester or a $C_1$-$C_8$ alkylaryl ester, which can be unsubstituted or substituted with at least one substituent selected from nitrate ester, $C_1$-$C_8$ alkyl nitrate ester or a $C_3$-$C_{10}$ cycloalkyl nitrate ester;

(ii) a $C_1$-$C_8$ alkyl ester or a $C_1$-$C_8$ alkoxy ester, which can be unsubstituted or substituted with $ONO_2$; or a $C_3$-$C_{10}$ cycloalkyl ester or a $C_1$-$C_8$ cycloalkoxy ester, which can be unsubstituted or substituted with $ONO_2$; or an unsubstituted or a substituted arylester, alkylaryl ester, benzoate, a nicotinate oxazoleoate, isoxazoleate, thiadiazoleoate group, which may be substituted by at least one of the group comprising hydroxide, —Cl, —Br, a $C_1$-$C_8$ alkyl, benzyl, a $C_1$-$C_8$ alkoxy, benzyloxy, —NHC(O)R, —$NH_2$, —$NO_2$, —$ONO_2$, —$(CH_2)_nONO_2$, —OC(O)[$(CH_2)_m]_{cyclic}ONO_2$, —$OCOArONO_2$, —$OCOAr(CH_2)_nONO_2$ or a $C_1$-$C_5$ haloalkyl ester, wherein R is a $C_1$-$C_8$ alkyl or a $C_1$-$C_8$ alkoxy group, n=1-8, m=3-10;

(iii) a $C_1$-$C_8$ alkyl ester or a $C_1$-$C_8$ alkoxy ester, which can be unsubstituted or substituted with $ONO_2$; or an unsubstituted or a substituted arylester, alkylaryl ester, benzoate, nicotinate, oxazoleoate, isoxazoleate, thiadiazoleoate group, which may be substituted by at least one of the group comprising hydroxide, —Cl, —Br, a $C_1$-$C_8$ alkyl, benzyl, a $C_1$-$C_8$ alkoxy, o-benzyloxy, —NHC(O)R, —$NH_2$, —$NO_2$, —$ONO_2$, —$(CH_2)_nONO_2$, —C(O)[$(CH_2)_m]_{cyclic}ONO_2$, —$OCOArONO_2$, —$OCOAr(CH_2)_nONO_2$ or a $C_1$-$C_5$ haloalkyl ester, wherein R is a $C_1$-$C_8$ alkyl or a $C_1$-$C_8$ alkoxy group, n=1-8, m=3-10;

(iv) a $C_1$-$C_8$ alkoxy ester, which can be unsubstituted or substituted with $ONO_2$; or an unsubstituted or a substituted benzoate or nicotinate group, which may be substituted by at least one of the group comprising hydroxide, —Cl, —Br, a $C_1$-$C_8$ alkyl, benzyl, a $C_1$-$C_8$ alkoxy, o-benzyloxy, —NHC(O)R, —$NH_2$, —$NO_2$, —$ONO_2$, —$(CH_2)_nONO_2$, —OC(O)[$(CH_2)_m]_{cyclic}ONO_2$, —$OCOArONO_2$, —$OCOAr(CH_2)_nONO_2$ or a $C_1$-$C_5$ haloalkyl ester, wherein R is a $C_1$-$C_8$ alkyl or a $C_1$-$C_8$ alkoxy group, n=1-8, m=3-10;

(v) an unsubstituted or a substituted benzoate or nicotinate group, which may be substituted by at least one of hydroxide, $C_1$-$C_8$ alkyl, $C_1$-$C_8$ alkyoxy, o-benzyloxy, —$(CH_2)_nONO_2$ (n=1-8), $C_3$-$C_{10}$ cycloalkyl ester or haloalkyl ester; and (vi) an unsubstituted or a substituted benzoate or nicotinate group, which may be substituted by at least one of hydroxide, —Cl, methyl, o-benzyloxy, methoxy, —$NHC(O)CH_3$, —$OC(O)CH_2Br$, —$NO_2$, —$CH_2ONO_2$, wherein Y is an unsubstituted or a substituted benzoate or nicotinate group, which may be substituted by at least one of hydroxide, —Cl, methyl, o-benzyloxy, methoxy, —$NHC(O)CH_3$, —$OC(O)CH_2Br$, —$NO_2$, —$CH_2ONO_2$;

wherein the cardiovascular disease is not dyslipidemia or platelet aggregability/aggregation, and wherein the compound is not a compound having the structure:

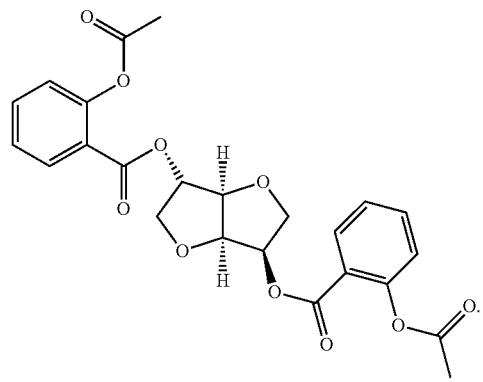

17. The method of claim 16, wherein the compound induces an aspirin like effect.

* * * * *

UNITED STATES PATENT AND TRADEMARK OFFICE
CERTIFICATE OF CORRECTION

| | |
|---|---|
| PATENT NO. | : 8,486,974 B2 |
| APPLICATION NO. | : 12/808693 |
| DATED | : July 16, 2013 |
| INVENTOR(S) | : Gilmer et al. |

Page 1 of 1

It is certified that error appears in the above-identified patent and that said Letters Patent is hereby corrected as shown below:

On the Title Page:

The first or sole Notice should read --

Subject to any disclaimer, the term of this patent is extended or adjusted under 35 U.S.C. 154(b) by 288 days.

Signed and Sealed this
Fourth Day of March, 2014

Michelle K. Lee
*Deputy Director of the United States Patent and Trademark Office*

UNITED STATES PATENT AND TRADEMARK OFFICE
CERTIFICATE OF CORRECTION

PATENT NO.       : 8,486,974 B2                                                        Page 1 of 1
APPLICATION NO.  : 12/808693
DATED            : July 16, 2013
INVENTOR(S)      : Gilmer et al.

It is certified that error appears in the above-identified patent and that said Letters Patent is hereby corrected as shown below:

On the Title Page:

The first or sole Notice should read --

Subject to any disclaimer, the term of this patent is extended or adjusted under 35 U.S.C. 154(b) by 269 days.

Signed and Sealed this
Eighth Day of September, 2015

Michelle K. Lee
*Director of the United States Patent and Trademark Office*